United States Patent
Hu

(10) Patent No.: US 7,314,630 B2
(45) Date of Patent: Jan. 1, 2008

(54) COMPOUNDS AND METHODS OF EARLY DIAGNOSIS OF CERVICAL CANCER AND GENITAL CONDYLOMA WITH HPV, CHSP60 TUMOR SUPPRESSOR H-RAS, K-RAS AND PTEN DERIVED PEPTIDES MODIFIED

(76) Inventor: Yao-Xiong Hu, 234 Escuela Ave. #47, Mountain View, CA (US) 94040

( * ) Notice: Subject to any disclaimer, the term of this patent is extended or adjusted under 35 U.S.C. 154(b) by 400 days.

(21) Appl. No.: 10/905,527

(22) Filed: Jan. 7, 2005

(65) Prior Publication Data

US 2006/0154238 A1 Jul. 13, 2006

(51) Int. Cl.
*A61K 39/12* (2006.01)

(52) U.S. Cl. ........................................ 424/204.1; 435/6

(58) Field of Classification Search ............. 424/204.1; 435/69.1, 6
See application file for complete search history.

(56) References Cited

U.S. PATENT DOCUMENTS

| | | | | |
|---|---|---|---|---|
| 5,855,891 | A * | 1/1999 | Lowy et al. | 424/192.1 |
| 6,228,368 | B1 * | 5/2001 | Gissmann et al. | 424/204.1 |
| 6,306,397 | B1 * | 10/2001 | Edwards et al. | 424/192.1 |
| 6,991,795 | B1 * | 1/2006 | Lowe et al. | 424/185.1 |
| 7,182,947 | B2 * | 2/2007 | Hallek et al. | 424/204.1 |

OTHER PUBLICATIONS

Anna S. Kadish, et al: Regression of cervical intraepithelial neoplasia and loss of human papillomavirus (HPV) infection is associated with cell-mediated immune responses to an HPV type 16 E7 peptide. Cancer Epidemiology, Biomarkers & Prevention 11: 483-488, 2002.

M.Y. Tjiong, et al: Antibodies against human papillomavirus type 16 and 18 E6 and E7 protein in cericovaginal washings and serum of patients with cervical neoplasia. Viral immunology. 14: 415-424, 2001.

Ricardo Rosales, et al: Antibodies against Human Papillomavirus (HPV) Type 16 and 18 E2, E6 and E7 proteins in Sera: Correlation With Presence of Papillomavirus DNA. J Med. Virol 65: 736-744, 2001.

A. Pedroza-Saavedra, et al: high prevalence of serum antibodies to ras and type 16 E4 proteins of human papillomavirus in patients with precancerous lesions of the uterine cervix. Arch Virol 145: 603-623, 2000.

Shixuan Huang, et al: Human Papillomavirus type 52 and 58 are prevalent in cervical cancers from Chinese women, Int. J. Cancer, 70: 408-411, 1997.

Koji Matsumoto, et al: Human Papillomavirus type 16 E6 variants and HLA class II Alleles among Japanese women with cervical cancer, Int. J. Cancer, 106: 919-922, 2003.

Huang-Cheng Lai, et al: Favorable clinic outcome of cervical cancers infected with human papillomavirus type 58 and related types, Int. J. cancer, 84: 553-557, 1999.

Alba-Lucia Combita, et al: Serologic response to human oncogenic papillomavirus types 16, 18, 31, 33, 58, and 59 virus-like particles in Columbian women with invasive cervical cancer, Int. J. Cancer, 97: 796-803, 2002.

Anna Di Lonardo, et al: HPV 16 E7 antibody levels in cervical cancer patients: Before and after treatment, Journal of Medical Virology, 54: 193-195, 1998.

Tarja Anttila, et al: Serotypes of Chlamydia trachomatis and risk for development of cervical squamous cell carcinoma, JAMA, 285 (1): 2001.

Arkadiusz Chil, et al: Alternations in expression of selected HMCX antigens in premalignant lesions and squamous carcinomas of the uterine cervix, Acta Obstetricia et Gynecologia Scandinavica, 82: 1146-1152, 2003.

Lora Hedrick Ellenson, et al: Focus on endometrial and cervical cancer, Cancer Cell, 533-538, 2004.

Takeo Minaguchi, et al: Association of PTEN mutation with HPV-negative adenocarcinoma of the uterine cervix, Cancer Letters, 210: 57-62 2004.

* cited by examiner

*Primary Examiner*—Ali R. Salimi
(74) *Attorney, Agent, or Firm*—Intellectual Property Law Group LLP; Otto O. Lee

(57) ABSTRACT

An isolated sequence or peptide isolated from an E2, E4, E6, E7 early or late coding region of human papillomavirus (HPV) that is soluble in aqueous medium, and characterized by a linkage to another protein sequence or peptide isolated from the E2, E4, E6, E7 early or late coding region of HPV by a spacer sequence, wherein the isolated protein sequence or peptide consists of more than 50% hydrophilic amino acids, and is recognized by a specific antibody of HPV. Also disclosed are isolated protein sequences or peptides from Harvey Ras (H-Ras), Kirsten Ras (K-Ras), and phosphatase and tensin homologue (PTEN) tumor suppressor proteins and Chlamydia trachomatis heat shock protein 60 (CHSP60 groEL1) and methods for detecting or diagnosing cancer or cellular abnormalities.

1 Claim, No Drawings

```
                              SEQUENCE LISTING

<160> NUMBER OF SEQ ID NOS: 182

<210> SEQ ID NO 1
<211> LENGTH: 26
<212> TYPE: PRT
<213> ORGANISM: Artificial Sequence
<220> FEATURE:
<223> OTHER INFORMATION: Derived from the E7 region of HPV 16. Includes
      GPG spacer sequence.
<220> FEATURE:
<221> NAME/KEY: misc_feature
<222> LOCATION: (18)..(18)
<223> OTHER INFORMATION: Xaa is preferably norleucine (NLE).

<400> SEQUENCE: 1

Lys Leu Asn Asp Ser Ser Glu Glu Glu Asp Glu Ile Asp Gly Pro Gly
1               5                   10                  15

Tyr Xaa Leu Asp Leu Gln Pro Glu Thr Asp
            20                  25

<210> SEQ ID NO 2
<211> LENGTH: 16
<212> TYPE: PRT
<213> ORGANISM: Artificial Sequence
<220> FEATURE:
<223> OTHER INFORMATION: Derived from the E7 region of HPV 16.  Met
      replaced with Nle and Cys replaced with Ser.
<220> FEATURE:
<221> NAME/KEY: misc_feature
<222> LOCATION: (4)..(4)
<223> OTHER INFORMATION: Xaa is preferably norleucine (NLE).

<400> SEQUENCE: 2

Lys Leu Leu Xaa Gly Thr Leu Gly Ile Val Ser Pro Ile Ser Ser Glu
1               5                   10                  15

<210> SEQ ID NO 3
<211> LENGTH: 31
<212> TYPE: PRT
<213> ORGANISM: Artificial Sequence
<220> FEATURE:
<223> OTHER INFORMATION: Derived from the E7 regions of HPV 16 and 18.
      GPG spacer sequence.
<220> FEATURE:
<221> NAME/KEY: misc_feature
<222> LOCATION: (11)..(11)
<223> OTHER INFORMATION: Xaa is preferably norleucine (NLE).

<400> SEQUENCE: 3

Arg Asp Ile Arg Thr Leu Glu Asp Leu Leu Xaa Gly Pro Gly Asp Ser
1               5                   10                  15

Glu Glu Glu Asn Asp Glu Ile Gly Asp Val Asn His Gln His Glu
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Derived from the E7 region of HPV 16 and 18.
      GPG spacer sequence.

<400> SEQUENCE: 4

Lys Leu Asn Asp Ser Ser Glu Glu Glu Asp Glu Ile Asp Gly Pro Gly
1               5                   10                  15
```

-continued

Asp Ser Glu Glu Glu Asn Asp Glu Ile Gly Val Asn His Gln His Glu
            20                  25                  30

<210> SEQ ID NO 5
<211> LENGTH: 36
<212> TYPE: PRT
<213> ORGANISM: Artificial Sequence
<220> FEATURE:
<223> OTHER INFORMATION: Derived from the E6 and E7 regions of HPV 16.
      GPG spacer sequence.

<400> SEQUENCE: 5

Lys Leu Asn Asp Ser Ser Glu Glu Asp Glu Ile Asp Gly Pro Gly
1               5                   10                  15

Glu Glu Lys Gln Arg His Leu Asp Lys Lys Gln Arg Phe His Asn Ile
            20                  25                  30

Arg Gly Arg Asp
        35

<210> SEQ ID NO 6
<211> LENGTH: 37
<212> TYPE: PRT
<213> ORGANISM: Artificial Sequence
<220> FEATURE:
<223> OTHER INFORMATION: Derived from the E6 and E7 regions of HPV 18.
      GPG spacer sequence.

<400> SEQUENCE: 6

Lys Ala Glu Lys Leu Arg His Leu Asn Glu Lys Arg Arg Phe His Asn
1               5                   10                  15

Ile Ala Gly Pro Gly Asp Ser Glu Glu Asn Asp Glu Ile Gly Asp Val
            20                  25                  30

Asn His Gln His Glu
        35

<210> SEQ ID NO 7
<211> LENGTH: 28
<212> TYPE: PRT
<213> ORGANISM: Artificial Sequence
<220> FEATURE:
<223> OTHER INFORMATION: Derived from the E6 region of HPV 16. Met
      replaced with Nle and Cys replaced with Ser.
<220> FEATURE:
<221> NAME/KEY: misc_feature
<222> LOCATION: (2)..(2)
<223> OTHER INFORMATION: Xaa is preferably norleucine (NLE).
<220> FEATURE:
<221> NAME/KEY: misc_feature
<222> LOCATION: (9)..(9)
<223> OTHER INFORMATION: Xaa is preferably norleucine (NLE).

<400> SEQUENCE: 7

Lys Xaa His Gln Lys Arg Thr Ala Xaa Phe Gln Asp Pro Gln Glu Arg
1               5                   10                  15

Pro Arg Lys Leu Pro Gln Leu Ser Thr Glu Leu Glu
            20                  25

<210> SEQ ID NO 8
<211> LENGTH: 29
<212> TYPE: PRT
<213> ORGANISM: Artificial Sequence
<220> FEATURE:
<223> OTHER INFORMATION: Derived from the E7 region of HPV 18.

<400> SEQUENCE: 8

Lys Ser Asp Ser Glu Glu Asn Asp Glu Ile Gly Asp Val Asn His Gln

-continued

```
1               5                   10                  15
His Leu Pro Ala Arg Arg Ala Glu Pro Gln Arg His Glu
            20                  25
```

```
<210> SEQ ID NO 9
<211> LENGTH: 34
<212> TYPE: PRT
<213> ORGANISM: Artificial Sequence
<220> FEATURE:
<223> OTHER INFORMATION: Derived from the E2 region of HPV 18 and the L1
      region of HPV 16/18. GPG spacer sequence.
<220> FEATURE:
<221> NAME/KEY: misc_feature
<222> LOCATION: (27)..(27)
<223> OTHER INFORMATION: Xaa is preferably norleucine (NLE).

<400> SEQUENCE: 9
```

```
Arg Glu Lys Thr Gly Ile Leu Thr Val Thr Tyr His Ser Glu Thr Gln
1               5                   10                  15
Arg Thr Lys Gly Pro Gly Tyr Ile His Ser Xaa Asn Ser Thr Ile Leu
            20                  25                  30
Glu Asp
```

```
<210> SEQ ID NO 10
<211> LENGTH: 33
<212> TYPE: PRT
<213> ORGANISM: Artificial Sequence
<220> FEATURE:
<223> OTHER INFORMATION: Derived from the E7 region of HPV 16. Cys
      replaced with Ser.

<400> SEQUENCE: 10
```

```
Lys Gly Gln Ala Glu Pro Asp Arg Ala His Tyr Asn Ile Val Thr Phe
1               5                   10                  15
Ser Ser Lys Ser Asp Ser Thr Leu Ser Ser Thr His Val Asp Ile Arg
            20                  25                  30
Glu
```

```
<210> SEQ ID NO 11
<211> LENGTH: 30
<212> TYPE: PRT
<213> ORGANISM: Artificial Sequence
<220> FEATURE:
<223> OTHER INFORMATION: Derived from the E7 region of HPV 16 and L1
      region of HPV 16/18. GPG spacer sequence.
<220> FEATURE:
<221> NAME/KEY: misc_feature
<222> LOCATION: (4)..(4)
<223> OTHER INFORMATION: Xaa is preferably norleucine (NLE).
<220> FEATURE:
<221> NAME/KEY: misc_feature
<222> LOCATION: (23)..(23)
<223> OTHER INFORMATION: Xaa is preferably norleucine (NLE).

<400> SEQUENCE: 11
```

```
Lys Leu Leu Xaa Gly Thr Leu Gly Ile Val Ser Pro Ile Ser Ser Gly
1               5                   10                  15
Pro Gly Tyr Ile His Ser Xaa Asn Ser Thr Ile Leu Glu Asp
            20                  25                  30
```

```
<210> SEQ ID NO 12
<211> LENGTH: 39
<212> TYPE: PRT
<213> ORGANISM: Artificial Sequence
<220> FEATURE:
<223> OTHER INFORMATION: Derived from the E7 regions of HPV 16 and HPV
```

18. GPG spacer sequence.

<400> SEQUENCE: 12

Arg Ala His Tyr Asn Ile Val Thr Phe Ser Gly Pro Gly Ser Glu Glu
1               5                   10                  15

Glu Asn Asp Glu Ile Asp Gly Val Asn His Gln His Leu Pro Ala Arg
            20                  25                  30

Arg Ala Glu Pro Gln Arg Glu
        35

<210> SEQ ID NO 13
<211> LENGTH: 35
<212> TYPE: PRT
<213> ORGANISM: Artificial Sequence
<220> FEATURE:
<223> OTHER INFORMATION: Derived from the E7 region of HPV 16. Met
      replaced with Nle.
<220> FEATURE:
<221> NAME/KEY: misc_feature
<222> LOCATION: (11)..(11)
<223> OTHER INFORMATION: Xaa is preferably norleucine (NLE).

<400> SEQUENCE: 13

Lys Gly Asp Thr Pro Thr Leu His Glu Tyr Xaa Leu Asp Leu Gln Pro
1               5                   10                  15

Glu Thr Thr Asp Leu Tyr Ser Tyr Glu Gln Leu Asn Asp Ser Ser Glu
            20                  25                  30

Glu Glu Asp
        35

<210> SEQ ID NO 14
<211> LENGTH: 31
<212> TYPE: PRT
<213> ORGANISM: Artificial Sequence
<220> FEATURE:
<223> OTHER INFORMATION: Derived from the L1 region of HPV 16/18 and E7
      region of HPV 58. GPG spacer sequence.
<220> FEATURE:
<221> NAME/KEY: misc_feature
<222> LOCATION: (6)..(6)
<223> OTHER INFORMATION: Xaa is preferably norleucine (NLE).
<220> FEATURE:
<221> NAME/KEY: misc_feature
<222> LOCATION: (23)..(23)
<223> OTHER INFORMATION: Xaa is preferably norleucine (NLE).

<400> SEQUENCE: 14

Asp Tyr Ile His Ser Xaa Asn Ser Thr Ile Leu Gly Pro Gly Val Arg
1               5                   10                  15

Thr Leu Gln Gln Leu Leu Xaa Gly Thr Ser Thr Ile Val Ser Asp
            20                  25                  30

<210> SEQ ID NO 15
<211> LENGTH: 28
<212> TYPE: PRT
<213> ORGANISM: Artificial Sequence
<220> FEATURE:
<223> OTHER INFORMATION: Derived from the E7 regions of HPV 58 and HPV
      16. GPG spacer sequence.
<220> FEATURE:
<221> NAME/KEY: misc_feature
<222> LOCATION: (16)..(16)
<223> OTHER INFORMATION: Xaa is preferably norleucine (NLE).

<400> SEQUENCE: 15

Lys Ile Gly Leu Asp Gly Pro Asp Gly Gln Gly Pro Gly Leu Leu Xaa
1               5                   10                  15

```
Gly Thr Leu Gly Ile Val Ser Pro Ile Ser Ser Asp
        20                  25

<210> SEQ ID NO 16
<211> LENGTH: 44
<212> TYPE: PRT
<213> ORGANISM: Artificial Sequence
<220> FEATURE:
<223> OTHER INFORMATION: Derived from the E6 region of HPV 58 and E7
      region of HPV 16. GPG spacer sequence.
<220> FEATURE:
<221> NAME/KEY: misc_feature
<222> LOCATION: (32)..(32)
<223> OTHER INFORMATION: Xaa is preferably norleucine (NLE).

<400> SEQUENCE: 16

Lys Leu Gln Arg Ser Glu Val Tyr Asp Phe Val Phe Ala Asp Leu Arg
1               5                   10                  15

Ile Val Tyr Arg Asp Gly Asn Pro Phe Ala Gly Pro Gly Leu Leu Xaa
            20                  25                  30

Gly Thr Leu Gly Ile Val Ser Pro Ile Ser Ser Glu
        35                  40

<210> SEQ ID NO 17
<211> LENGTH: 40
<212> TYPE: PRT
<213> ORGANISM: Artificial Sequence
<220> FEATURE:
<223> OTHER INFORMATION: Derived from the E6 regions of HPV 58 and HPV
      16. GPG spacer sequence.

<400> SEQUENCE: 17

Glu Leu Gln Arg Ser Glu Val Tyr Asp Phe Val Phe Ala Asp Leu Arg
1               5                   10                  15

Ile Val Tyr Arg Asp Gly Asn Pro Phe Ala Gly Pro Gly Lys Leu Pro
            20                  25                  30

Gln Leu Ser Thr Glu Leu Gln Asp
        35                  40

<210> SEQ ID NO 18
<211> LENGTH: 32
<212> TYPE: PRT
<213> ORGANISM: Artificial Sequence
<220> FEATURE:
<223> OTHER INFORMATION: Derived from the E7 region of HPV 16 and E6
      region of HPV 58. GPG spacer sequence.

<400> SEQUENCE: 18

Arg Glu Leu Gly Ile Val Ser Pro Ile Ser Ser Gly Pro Gly Leu Arg
1               5                   10                  15

Leu Leu Ser Lys Ile Ser Glu Tyr Arg His Tyr Asn Tyr Ser Leu Tyr
            20                  25                  30

<210> SEQ ID NO 19
<211> LENGTH: 36
<212> TYPE: PRT
<213> ORGANISM: Artificial Sequence
<220> FEATURE:
<223> OTHER INFORMATION: Derived from the E6 region of HPV 58 and E7
      region of HPV 16. GPG spacer sequence.
<220> FEATURE:
<221> NAME/KEY: misc_feature
<222> LOCATION: (24)..(24)
<223> OTHER INFORMATION: Xaa is preferably norleucine (NLE).

<400> SEQUENCE: 19
```

```
Lys Leu Arg Leu Leu Ser Lys Ile Ser Glu Tyr Arg His Asn Tyr Ser
1               5                   10                  15

Leu Tyr Gly Pro Gly Leu Leu Xaa Gly Thr Leu Gly Ile Val Ser Pro
            20                  25                  30

Ile Ser Ser Glu
        35

<210> SEQ ID NO 20
<211> LENGTH: 34
<212> TYPE: PRT
<213> ORGANISM: Artificial Sequence
<220> FEATURE:
<223> OTHER INFORMATION: Derived from the E7 regions of HPV 16 and HPV
      58/16. GPG spacer sequence.

<400> SEQUENCE: 20

Lys Glu Leu Asn Asp Ser Ser Glu Glu Glu Asp Glu Ile Asp Gly Pro
1               5                   10                  15

Gly Leu Arg Leu Leu Ser Lys Ile Ser Glu Tyr Arg His Asn Tyr Ser
            20                  25                  30

Leu Tyr

<210> SEQ ID NO 21
<211> LENGTH: 32
<212> TYPE: PRT
<213> ORGANISM: Artificial Sequence
<220> FEATURE:
<223> OTHER INFORMATION: Derived from the E6 regions of HPV 16 and HPV
      52. GPG spacer sequence.

<400> SEQUENCE: 21

Arg Lys Leu Pro Gln Leu Ser Thr Glu Leu Gly Pro Gly Val Tyr Lys
1               5                   10                  15

Phe Leu Phe Thr Asp Leu Arg Ile Val Tyr Arg Asp Asn Asn Pro Tyr
            20                  25                  30

<210> SEQ ID NO 22
<211> LENGTH: 42
<212> TYPE: PRT
<213> ORGANISM: Artificial Sequence
<220> FEATURE:
<223> OTHER INFORMATION: Derived from the E6 regions of HPV 16 and HPV
      52 and E7 regions of HPV 58. GPG spacer sequence.
<220> FEATURE:
<221> NAME/KEY: misc_feature
<222> LOCATION: (34)..(34)
<223> OTHER INFORMATION: Xaa is preferably norleucine (NLE).

<400> SEQUENCE: 22

Lys Leu Pro Gln Leu Ser Thr Glu Leu Gln Gly Pro Gly Ile Arg Leu
1               5                   10                  15

Gln Ser Val Gln Ser Lys Gly Pro Gly Val Arg Thr Leu Gln Gln Leu
            20                  25                  30

Leu Xaa Gly Thr Ser Thr Ile Val Ser Asp
        35                  40

<210> SEQ ID NO 23
<211> LENGTH: 35
<212> TYPE: PRT
<213> ORGANISM: Artificial Sequence
<220> FEATURE:
<223> OTHER INFORMATION: Derived from the E7 regions of HPV 16 and HPV
      58. GPG spacer sequence.
<220> FEATURE:
<221> NAME/KEY: misc_feature
```

```
<222> LOCATION: (4)..(4)
<223> OTHER INFORMATION: Xaa is preferably norleucine (NLE).
<220> FEATURE:
<221> NAME/KEY: misc_feature
<222> LOCATION: (27)..(27)
<223> OTHER INFORMATION: Xaa is preferably norleucine (NLE).

<400> SEQUENCE: 23

Lys Leu Leu Xaa Gly Thr Leu Gly Ile Val Ser Pro Ile Ser Ser Gly
1               5                   10                  15

Pro Gly Val Arg Thr Leu Gln Gln Leu Leu Xaa Gly Thr Ser Thr Ile
            20                  25                  30

Val Ser Glu
        35

<210> SEQ ID NO 24
<211> LENGTH: 25
<212> TYPE: PRT
<213> ORGANISM: Artificial Sequence
<220> FEATURE:
<223> OTHER INFORMATION: Derived from the E6 regions of HPV 16 and HPV
      52. GPG spacer sequence.

<400> SEQUENCE: 24

Lys Ile Val Tyr Arg Asp Gly Asn Pro Tyr Gly Gly Pro Gly Gly Ile
1               5                   10                  15

Arg Leu Gln Ser Val Gln Ser Lys Asp
            20                  25

<210> SEQ ID NO 25
<211> LENGTH: 30
<212> TYPE: PRT
<213> ORGANISM: Artificial Sequence
<220> FEATURE:
<223> OTHER INFORMATION: Derived from the E6 region of HPV 52 and E7
      region of HPV 58. GPG spacer sequence.
<220> FEATURE:
<221> NAME/KEY: misc_feature
<222> LOCATION: (22)..(22)
<223> OTHER INFORMATION: Xaa is preferably norleucine (NLE).

<400> SEQUENCE: 25

Lys Ile Arg Leu Gln Ser Val Gln Ser Lys Gly Pro Gly Val Arg Thr
1               5                   10                  15

Leu Gln Gln Leu Leu Xaa Gly Thr Ser Thr Ile Val Ser Glu
            20                  25                  30

<210> SEQ ID NO 26
<211> LENGTH: 38
<212> TYPE: PRT
<213> ORGANISM: Artificial Sequence
<220> FEATURE:
<223> OTHER INFORMATION: Derived from the E6 region of HPV 16 and E7
      region of HPV 52. GPG spacer sequence.
<220> FEATURE:
<221> NAME/KEY: misc_feature
<222> LOCATION: (15)..(15)
<223> OTHER INFORMATION: Xaa is preferably norleucine (NLE).

<400> SEQUENCE: 26

Lys Asn Val Tyr Arg Asp Gly Asn Pro Tyr Ala Gly Pro Gly Xaa Arg
1               5                   10                  15

Gly Asp Lys Ala Thr Ile Lys Asp Tyr Ile Leu Asp Leu Gln Pro Glu
            20                  25                  30

Thr Thr Asp Leu His Glu
        35
```

<210> SEQ ID NO 27
<211> LENGTH: 36
<212> TYPE: PRT
<213> ORGANISM: Artificial Sequence
<220> FEATURE:
<223> OTHER INFORMATION: Derived from the E7 regions of HPV 52 and HPV
     16. GPG spacer sequence.
<220> FEATURE:
<221> NAME/KEY: misc_feature
<222> LOCATION: (3)..(3)
<223> OTHER INFORMATION: Xaa is preferably norleucine (NLE).

<400> SEQUENCE: 27

Lys Glu Xaa Arg Gly Asp Lys Ala Thr Ile Lys Asp Tyr Ile Leu Asp
1               5                   10                  15

Leu Gln Pro Glu Thr Gly Pro Gly Leu Asn Asp Ser Ser Glu Glu Glu
            20                  25                  30

Asp Glu Ile Asp
        35

<210> SEQ ID NO 28
<211> LENGTH: 31
<212> TYPE: PRT
<213> ORGANISM: Artificial Sequence
<220> FEATURE:
<223> OTHER INFORMATION: Derived from the E7 regions of HPV 58 and HPV
     52. GPG spacer sequence.
<220> FEATURE:
<221> NAME/KEY: misc_feature
<222> LOCATION: (10)..(10)
<223> OTHER INFORMATION: Xaa is preferably norleucine (NLE).
<220> FEATURE:
<221> NAME/KEY: misc_feature
<222> LOCATION: (27)..(27)
<223> OTHER INFORMATION: Xaa is preferably norleucine (NLE).

<400> SEQUENCE: 28

Lys Val Arg Thr Leu Gln Gln Leu Leu Xaa Gly Thr Ser Thr Ile Val
1               5                   10                  15

Ser Gly Pro Gly Leu Arg Thr Leu Gln Gln Xaa Leu Leu Asn Glu
            20                  25                  30

<210> SEQ ID NO 29
<211> LENGTH: 23
<212> TYPE: PRT
<213> ORGANISM: Artificial Sequence
<220> FEATURE:
<223> OTHER INFORMATION: Derived from the E6 and E2 region of HPV 16.
     GPG spacer sequence.

<400> SEQUENCE: 29

Lys Tyr Arg His Tyr Ser Tyr Ser Leu Tyr Gly Pro Gly Thr Leu Gln
1               5                   10                  15

Asp Val Ser Leu Glu Val Asp
            20

<210> SEQ ID NO 30
<211> LENGTH: 25
<212> TYPE: PRT
<213> ORGANISM: Artificial Sequence
<220> FEATURE:
<223> OTHER INFORMATION: Derived from the E7 region of HPV 16. GGPGG
     spacer sequence.

<400> SEQUENCE: 30

His Leu Gly Ile Val Ser Pro Ile Ser Ser Gly Gly Pro Gly Gly Leu

```
                1               5                  10                 15
His Arg Asp Ser Val Asp Ser Ala Glu
            20                  25

<210> SEQ ID NO 31
<211> LENGTH: 12
<212> TYPE: PRT
<213> ORGANISM: Artificial Sequence
<220> FEATURE:
<223> OTHER INFORMATION: Derived from the E2 region of HPV 16.

<400> SEQUENCE: 31

His Thr Leu Thr Tyr Asp Ser Glu Trp Gln Arg Asp
1               5                  10

<210> SEQ ID NO 32
<211> LENGTH: 11
<212> TYPE: PRT
<213> ORGANISM: Artificial Sequence
<220> FEATURE:
<223> OTHER INFORMATION: Derived from the E2 region of HPV 16.

<400> SEQUENCE: 32

Lys Leu His Arg Asp Ser Val Asp Ser Ala Glu
1               5                  10

<210> SEQ ID NO 33
<211> LENGTH: 23
<212> TYPE: PRT
<213> ORGANISM: Artificial Sequence
<220> FEATURE:
<223> OTHER INFORMATION: Derived from the E2 region of HPV 16. GPG
      spacer sequence.
<220> FEATURE:
<221> NAME/KEY: misc_feature
<222> LOCATION: (14)..(14)
<223> OTHER INFORMATION: Xaa is preferably norleucine (NLE).

<400> SEQUENCE: 33

Lys Leu His Arg Asp Ser Val Asp Ser Ala Gly Pro Gly Xaa Arg Leu
1               5                  10                 15

Glu Cys Ala Ile Tyr Tyr Glu
            20

<210> SEQ ID NO 34
<211> LENGTH: 25
<212> TYPE: PRT
<213> ORGANISM: Artificial Sequence
<220> FEATURE:
<223> OTHER INFORMATION: Derived from the E2 region of HPV 16. GGPGG
      spacer sequence.

<400> SEQUENCE: 34

Lys Thr Leu Tyr Thr Ala Val Ser Ser Thr Gly Gly Pro Gly Gly Thr
1               5                  10                 15

Leu Gln Asp Val Ser Leu Glu Val Glu
            20                  25

<210> SEQ ID NO 35
<211> LENGTH: 25
<212> TYPE: PRT
<213> ORGANISM: Artificial Sequence
<220> FEATURE:
<223> OTHER INFORMATION: Derived from the E2 regions of HPV 16/18.
      GGPGG spacer sequence.

<400> SEQUENCE: 35
```

-continued

```
Lys Thr Leu Tyr Thr Ala Val Ser Ser Thr Gly Gly Pro Gly Gly Thr
1               5                   10                  15

Leu Ser Glu Arg Leu Ser Ser Val Glu
            20                  25

<210> SEQ ID NO 36
<211> LENGTH: 25
<212> TYPE: PRT
<213> ORGANISM: Artificial Sequence
<220> FEATURE:
<223> OTHER INFORMATION: Derived from the E2 region of HPV 16/18.
      GGPGG spacer sequence.

<400> SEQUENCE: 36

Lys Thr Leu Gln Asp Val Ser Leu Glu Val Gly Gly Pro Gly Gly Thr
1               5                   10                  15

Leu Ser Glu Arg Leu Ser Ser Val Glu
            20                  25

<210> SEQ ID NO 37
<211> LENGTH: 24
<212> TYPE: PRT
<213> ORGANISM: Artificial Sequence
<220> FEATURE:
<223> OTHER INFORMATION: Derived from the E2 and E7 region of HPV 16.
      GGPGG spacer sequence.
<220> FEATURE:
<221> NAME/KEY: misc_feature
<222> LOCATION: (16)..(16)
<223> OTHER INFORMATION: Xaa is preferably norleucine (NLE).

<400> SEQUENCE: 37

Lys Thr Leu Gln Asp Val Ser Leu Val Gly Gly Pro Gly Gly Tyr Xaa
1               5                   10                  15

Leu Asp Leu Gln Pro Glu Thr Asp
            20

<210> SEQ ID NO 38
<211> LENGTH: 25
<212> TYPE: PRT
<213> ORGANISM: Artificial Sequence
<220> FEATURE:
<223> OTHER INFORMATION: Derived from the E2 and E7 region of HPV 16.
      Met replaced with Nle.
<220> FEATURE:
<221> NAME/KEY: misc_feature
<222> LOCATION: (21)..(21)
<223> OTHER INFORMATION: Xaa is preferably norleucine (NLE).

<400> SEQUENCE: 38

Lys Thr Leu Tyr Thr Ala Val Ser Ser Thr Gly Gly Pro Gly Gly Thr
1               5                   10                  15

Leu His Glu Tyr Xaa Leu Asp Leu Arg
            20                  25

<210> SEQ ID NO 39
<211> LENGTH: 26
<212> TYPE: PRT
<213> ORGANISM: Artificial Sequence
<220> FEATURE:
<223> OTHER INFORMATION: Derived from the E2 and E7 region of HPV 16.
      GGPGG spacer sequence.
<220> FEATURE:
<221> NAME/KEY: misc_feature
<222> LOCATION: (21)..(21)
<223> OTHER INFORMATION: Xaa is preferably norleucine (NLE).
```

```
<400> SEQUENCE: 39

Lys Thr Leu Gln Asp Val Ser Leu Glu Val Gly Gly Pro Gly Gly Thr
1               5                   10                  15

Leu His Glu Tyr Xaa Leu Asp Leu Arg Glu
            20                  25

<210> SEQ ID NO 40
<211> LENGTH: 11
<212> TYPE: PRT
<213> ORGANISM: Artificial Sequence
<220> FEATURE:
<223> OTHER INFORMATION: Derived from the E2 region of HPV 18. Met
      replaced with Nle.
<220> FEATURE:
<221> NAME/KEY: misc_feature
<222> LOCATION: (10)..(10)
<223> OTHER INFORMATION: Xaa is preferably norleucine (NLE).

<400> SEQUENCE: 40

Lys Glu Val Ala Trp Ser Val Tyr Tyr Xaa Asp
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Derived from the E2 region of HPV 18. Met
      replaced with Nle.
<220> FEATURE:
<221> NAME/KEY: misc_feature
<222> LOCATION: (10)..(10)
<223> OTHER INFORMATION: Xaa is preferably norleucine (NLE).

<400> SEQUENCE: 41

Arg Val Gln Ile Leu Leu Val Gly Tyr Xaa Thr Asn Glu
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Derived from the E2 region of HPV 18.

<400> SEQUENCE: 42

Lys Thr Leu Ser Glu Arg Leu Ser Ser Val Arg Glu
1               5                   10

<210> SEQ ID NO 43
<211> LENGTH: 24
<212> TYPE: PRT
<213> ORGANISM: Artificial Sequence
<220> FEATURE:
<223> OTHER INFORMATION: Derived from the E7 and E2 region of HPV 18.
      GGPGG spacer sequence.

<400> SEQUENCE: 43

Lys Thr Leu Gln Asp Ile Val Leu His Gly Gly Pro Gly Gly Thr Leu
1               5                   10                  15

Ser Glu Arg Leu Ser Ser Val Glu
            20

<210> SEQ ID NO 44
<211> LENGTH: 25
<212> TYPE: PRT
<213> ORGANISM: Artificial Sequence
```

-continued

```
<220> FEATURE:
<223> OTHER INFORMATION: Derived from the E2 region of HPV 18/16. GGPGG
      spacer sequence.
<220> FEATURE:
<221> NAME/KEY: misc_feature
<222> LOCATION: (9)..(9)
<223> OTHER INFORMATION: Xaa is preferably norleucine (NLE).

<400> SEQUENCE: 44

Lys Val Gln Ile Leu Val Gly Tyr Xaa Thr Gly Gly Pro Gly Gly Leu
1               5                   10                  15

His Arg Asp Ser Val Asp Ser Gly Asp
            20                  25

<210> SEQ ID NO 45
<211> LENGTH: 27
<212> TYPE: PRT
<213> ORGANISM: Artificial Sequence
<220> FEATURE:
<223> OTHER INFORMATION: Derived from the E2 region of HPV 18/16. GGPGG
      spacer sequence.

<400> SEQUENCE: 45

Lys Thr Leu Ser Glu Arg Leu Ser Ser Val Gly Gly Pro Gly Gly Lys
1               5                   10                  15

Thr Leu Gln Asp Val Ser Leu Glu Val Arg Asp
            20                  25

<210> SEQ ID NO 46
<211> LENGTH: 25
<212> TYPE: PRT
<213> ORGANISM: Artificial Sequence
<220> FEATURE:
<223> OTHER INFORMATION: Derived from the E7 region of HPV 16/18. GGPGG
      spacer sequence.
<220> FEATURE:
<221> NAME/KEY: misc_feature
<222> LOCATION: (7)..(7)
<223> OTHER INFORMATION: Xaa is preferably norleucine (NLE).

<400> SEQUENCE: 46

Arg Thr Leu His Glu Tyr Xaa Leu Asp Leu Gly Gly Pro Gly Gly Thr
1               5                   10                  15

Leu Gln Asp Ile Val Leu His Leu Glu
            20                  25

<210> SEQ ID NO 47
<211> LENGTH: 25
<212> TYPE: PRT
<213> ORGANISM: Artificial Sequence
<220> FEATURE:
<223> OTHER INFORMATION: Derived from the E7 region of HPV 16/18. GGPGG
      spacer sequence.
<220> FEATURE:
<221> NAME/KEY: misc_feature
<222> LOCATION: (7)..(7)
<223> OTHER INFORMATION: Xaa is preferably norleucine (NLE).

<400> SEQUENCE: 47

Lys Thr Leu His Glu Tyr Xaa Leu Asp Leu Gly Gly Pro Gly Gly Phe
1               5                   10                  15

Gln Gln Leu Phe Leu Asn Thr Leu Glu
            20                  25

<210> SEQ ID NO 48
<211> LENGTH: 23
<212> TYPE: PRT
```

```
<213> ORGANISM: Artificial Sequence
<220> FEATURE:
<223> OTHER INFORMATION: Derived from the E6 region of HPV 16/18. GGPGG
      spacer sequence.

<400> SEQUENCE: 48

Lys Leu Pro Gln Ser Thr Glu Leu Gly Gly Pro Gly Gly Lys Leu Pro
1               5                   10                  15

Asp Leu Ser Thr Glu Leu Asp
            20

<210> SEQ ID NO 49
<211> LENGTH: 23
<212> TYPE: PRT
<213> ORGANISM: Artificial Sequence
<220> FEATURE:
<223> OTHER INFORMATION: Derived from the E6 region of the HPV 16/18.
      GGPGG spacer sequence.

<400> SEQUENCE: 49

Lys Ile Ser Glu Tyr Arg His Tyr Ser Gly Gly Pro Gly Gly Lys Pro
1               5                   10                  15

Asp Leu Ser Thr Glu Leu Glu
            20

<210> SEQ ID NO 50
<211> LENGTH: 24
<212> TYPE: PRT
<213> ORGANISM: Artificial Sequence
<220> FEATURE:
<223> OTHER INFORMATION: Derived from the E4 region of HPV 16/18. GGPGG
      spacer sequence.

<400> SEQUENCE: 50

Lys Leu Leu Gly Ser Thr Trp Pro Thr Gly Gly Pro Gly Gly Arg Leu
1               5                   10                  15

Leu His Asp Leu Asp Thr Val Glu
            20

<210> SEQ ID NO 51
<211> LENGTH: 25
<212> TYPE: PRT
<213> ORGANISM: Artificial Sequence
<220> FEATURE:
<223> OTHER INFORMATION: Derived from the E7 and E6 region of HPV 16.
      GGPGG spacer sequence.
<220> FEATURE:
<221> NAME/KEY: misc_feature
<222> LOCATION: (7)..(7)
<223> OTHER INFORMATION: Xaa is preferably norleucine (NLE).

<400> SEQUENCE: 51

Lys Thr Leu His Glu Tyr Xaa Leu Asp Leu Gly Gly Pro Gly Gly Lys
1               5                   10                  15

Leu Pro Gln Leu Ser Thr Glu Leu Glu
            20                  25

<210> SEQ ID NO 52
<211> LENGTH: 24
<212> TYPE: PRT
<213> ORGANISM: Artificial Sequence
<220> FEATURE:
<223> OTHER INFORMATION: Derived from the E6 and E2 region of HPV 16.
      GGPGG spacer sequence.

<400> SEQUENCE: 52
```

-continued

```
Lys Leu Pro Gln Leu Ser Thr Glu Leu Gly Gly Pro Gly Gly Thr Leu
1               5                   10                  15

Gln Asp Val Ser Leu Glu Val Glu
            20

<210> SEQ ID NO 53
<211> LENGTH: 24
<212> TYPE: PRT
<213> ORGANISM: Artificial Sequence
<220> FEATURE:
<223> OTHER INFORMATION: Derived from the E6 and E4 region of HPV 16.
      GGPGG spacer sequence.

<400> SEQUENCE: 53

Lys Leu Pro Gln Leu Ser Thr Glu Leu Gly Gly Pro Gly Gly Lys Leu
1               5                   10                  15

Leu Gly Ser Thr Trp Pro Thr Glu
            20

<210> SEQ ID NO 54
<211> LENGTH: 24
<212> TYPE: PRT
<213> ORGANISM: Artificial Sequence
<220> FEATURE:
<223> OTHER INFORMATION: Derived from the E6 and E4 region of HPV 16.
      GGPGG spacer sequence.

<400> SEQUENCE: 54

Lys Ile Ser Glu Tyr Arg His Tyr Ser Gly Gly Pro Gly Gly Lys Leu
1               5                   10                  15

Leu Gly Ser Thr Trp Pro Thr Glu
            20

<210> SEQ ID NO 55
<211> LENGTH: 25
<212> TYPE: PRT
<213> ORGANISM: Artificial Sequence
<220> FEATURE:
<223> OTHER INFORMATION: Derived from the E2 and E7 region of HPV 18.
      GGPGG spacer sequence.

<400> SEQUENCE: 55

Lys Thr Leu Ser Glu Arg Leu Ser Ser Val Gly Gly Pro Gly Gly Thr
1               5                   10                  15

Leu Gln Asp Ile Val Leu His Leu Asp
            20                  25

<210> SEQ ID NO 56
<211> LENGTH: 24
<212> TYPE: PRT
<213> ORGANISM: Artificial Sequence
<220> FEATURE:
<223> OTHER INFORMATION: Derived from the E6 and E4 region of HPV 18.
      GGPGG spacer sequence.

<400> SEQUENCE: 56

Lys Leu Pro Asp Leu Ser Thr Glu Leu Gly Gly Pro Gly Gly Arg Leu
1               5                   10                  15

Leu His Asp Leu Asp Thr Val Glu
            20

<210> SEQ ID NO 57
<211> LENGTH: 25
<212> TYPE: PRT
<213> ORGANISM: Artificial Sequence
```

```
<220> FEATURE:
<223> OTHER INFORMATION: Derived from the E7 and E6 region of HPV 18.
      GGPGG spacer sequence.

<400> SEQUENCE: 57

Lys Thr Leu Gln Asp Ile Val Leu His Leu Gly Gly Pro Gly Gly Lys
1               5                   10                  15

Leu Pro Asp Leu Ser Thr Glu Leu Asp
            20                  25

<210> SEQ ID NO 58
<211> LENGTH: 25
<212> TYPE: PRT
<213> ORGANISM: Artificial Sequence
<220> FEATURE:
<223> OTHER INFORMATION: Derived from the E2 and E6 region of HPV 18.
      GGPGG spacer sequence.

<400> SEQUENCE: 58

Lys Thr Leu Ser Glu Arg Leu Ser Ser Val Gly Gly Pro Gly Gly Lys
1               5                   10                  15

Leu Pro Asp Leu Ser Thr Glu Leu Asp
            20                  25

<210> SEQ ID NO 59
<211> LENGTH: 24
<212> TYPE: PRT
<213> ORGANISM: Artificial Sequence
<220> FEATURE:
<223> OTHER INFORMATION: Derived from the E6 and E2 region of HPV 31.
      GGPGG spacer sequence.

<400> SEQUENCE: 59

Lys Leu His Glu Leu Ser Ser Ala Leu Gly Gly Pro Gly Gly Gln Leu
1               5                   10                  15

Tyr Glu Gln Val Ser Ser Thr Glu
            20

<210> SEQ ID NO 60
<211> LENGTH: 24
<212> TYPE: PRT
<213> ORGANISM: Artificial Sequence
<220> FEATURE:
<223> OTHER INFORMATION: Derived from the E6 and E7 region of HPV 31.
      GGPGG spacer sequence.

<400> SEQUENCE: 60

Lys Leu His Glu Leu Ser Ser Ala Leu Gly Gly Pro Gly Gly Thr Leu
1               5                   10                  15

Gln Asp Tyr Val Leu Asp Leu Glu
            20

<210> SEQ ID NO 61
<211> LENGTH: 25
<212> TYPE: PRT
<213> ORGANISM: Artificial Sequence
<220> FEATURE:
<223> OTHER INFORMATION: Derived from the E2 and E4 region of HPV 31.
      GGPGG spacer sequence.

<400> SEQUENCE: 61

Lys Gln Leu Tyr Glu Gln Val Ser Ser Thr Gly Gly Pro Gly Gly Tyr
1               5                   10                  15

Leu Ala Val Thr Lys Tyr Pro Leu Glu
            20                  25
```

```
<210> SEQ ID NO 62
<211> LENGTH: 24
<212> TYPE: PRT
<213> ORGANISM: Artificial Sequence
<220> FEATURE:
<223> OTHER INFORMATION: Derived from the E2 and E4 region of HPV 31.
      GGPGG spacer sequence.

<400> SEQUENCE: 62

Arg Leu Leu Arg Gly Asp Ser Val Asp Ser Gly Gly Pro Gly Gly Leu
1               5                   10                  15

His Ala Gln Thr Lys Gln Gly Glu
            20

<210> SEQ ID NO 63
<211> LENGTH: 24
<212> TYPE: PRT
<213> ORGANISM: Artificial Sequence
<220> FEATURE:
<223> OTHER INFORMATION: Derived from the E2 and E4 region of HPV 31.
      GGPGG spacer sequence.

<400> SEQUENCE: 63

Arg Leu Leu Arg Gly Asp Ser Val Asp Ser Gly Gly Pro Gly Gly Leu
1               5                   10                  15

Arg Leu Tyr Leu Ala Thr Lys Tyr
            20

<210> SEQ ID NO 64
<211> LENGTH: 25
<212> TYPE: PRT
<213> ORGANISM: Artificial Sequence
<220> FEATURE:
<223> OTHER INFORMATION: Derived from the E6 and E7 region of HPV 33.
      GGPGG spacer sequence.
<220> FEATURE:
<221> NAME/KEY: misc_feature
<222> LOCATION: (18)..(18)
<223> OTHER INFORMATION: Xaa is preferably norleucine (NLE).

<400> SEQUENCE: 64

His Thr Leu His Asp Leu Ser Gln Ala Leu Gly Gly Pro Gly Gly Leu
1               5                   10                  15

Leu Xaa Gly Thr Val Asn Ile Val Glu
            20                  25

<210> SEQ ID NO 65
<211> LENGTH: 25
<212> TYPE: PRT
<213> ORGANISM: Artificial Sequence
<220> FEATURE:
<223> OTHER INFORMATION: Derived from the E2 and E7 region of HPV 33.
      GGPGG spacer sequence.
<220> FEATURE:
<221> NAME/KEY: misc_feature
<222> LOCATION: (19)..(19)
<223> OTHER INFORMATION: Xaa is preferably norleucine (NLE).

<400> SEQUENCE: 65

Arg Tyr Tyr Ile Val Thr Ser Ser His Thr Gly Gly Pro Gly Gly Leu
1               5                   10                  15

Ile Arg Xaa Glu Cys Ala Leu Leu Glu
            20                  25

<210> SEQ ID NO 66
```

```
<211> LENGTH: 24
<212> TYPE: PRT
<213> ORGANISM: Artificial Sequence
<220> FEATURE:
<223> OTHER INFORMATION: Derived from the E2 and E7 region of HPV 33.
      GGPGG spacer sequence.
<220> FEATURE:
<221> NAME/KEY: misc_feature
<222> LOCATION: (17)..(17)
<223> OTHER INFORMATION: Xaa is preferably norleucine (NLE).

<400> SEQUENCE: 66

Lys Leu Phe Ser Ala Asp Pro Ala Leu Gly Gly Pro Gly Gly Leu Leu
1               5                   10                  15

Xaa Gly Thr Val Ile Asn Val Glu
            20

<210> SEQ ID NO 67
<211> LENGTH: 24
<212> TYPE: PRT
<213> ORGANISM: Artificial Sequence
<220> FEATURE:
<223> OTHER INFORMATION: Derived from the E4 and E2 region of HPV 33.
      GGPGG spacer sequence.
<220> FEATURE:
<221> NAME/KEY: misc_feature
<222> LOCATION: (18)..(18)
<223> OTHER INFORMATION: Xaa is preferably norleucine (NLE).

<400> SEQUENCE: 67

Arg Leu Arg Leu Tyr Leu Ala Thr Lys Gly Gly Pro Gly Gly Leu Ile
1               5                   10                  15

Arg Xaa Glu Ser Ala Leu Leu Glu
            20

<210> SEQ ID NO 68
<211> LENGTH: 25
<212> TYPE: PRT
<213> ORGANISM: Artificial Sequence
<220> FEATURE:
<223> OTHER INFORMATION: Derived from the E4 and E2 region of HPV 33.
      GGPGG spacer sequence.

<400> SEQUENCE: 68

His Tyr Leu Ala Thr Lys Tyr Pro Leu Leu Gly Gly Pro Gly Gly Lys
1               5                   10                  15

Leu Phe Ser Ala Asp Pro Ala Leu Glu
            20                  25

<210> SEQ ID NO 69
<211> LENGTH: 25
<212> TYPE: PRT
<213> ORGANISM: Artificial Sequence
<220> FEATURE:
<223> OTHER INFORMATION: Derived from the E2 region of HPV 31/33. GGPGG
      spacer sequence.
<220> FEATURE:
<221> NAME/KEY: misc_feature
<222> LOCATION: (19)..(19)
<223> OTHER INFORMATION: Xaa is preferably norleucine (NLE).

<400> SEQUENCE: 69

His Leu Leu Arg Gly Asp Ser Val Asp Ser Gly Gly Pro Gly Gly Leu
1               5                   10                  15

Ile Arg Xaa Glu Ser Ala Leu Leu Glu
            20                  25
```

```
<210> SEQ ID NO 70
<211> LENGTH: 25
<212> TYPE: PRT
<213> ORGANISM: Artificial Sequence
<220> FEATURE:
<223> OTHER INFORMATION: Derived from the E2 region of HPV 31/33. GGPGG
      spacer sequence.

<400> SEQUENCE: 70

Lys Gln Leu Tyr Lys Gln Val Ser Ser Thr Gly Gly Pro Gly Gly Lys
1               5                   10                  15

Leu Phe Ser Ala Asp Pro Ala Leu Glu
            20                  25

<210> SEQ ID NO 71
<211> LENGTH: 24
<212> TYPE: PRT
<213> ORGANISM: Artificial Sequence
<220> FEATURE:
<223> OTHER INFORMATION: Derived from the E6 region of HPV 31/33. GGPGG
      spacer sequence

<400> SEQUENCE: 71

Lys Leu Arg Leu Asn Ser Val Tyr Ser Lys Gly Gly Pro Gly Gly Leu
1               5                   10                  15

Arg Phe Leu Ser Lys Ile Ser Glu
            20

<210> SEQ ID NO 72
<211> LENGTH: 23
<212> TYPE: PRT
<213> ORGANISM: Artificial Sequence
<220> FEATURE:
<223> OTHER INFORMATION: Derived from the E6 region of HPV 31/33. GGPGG
      spacer sequence.

<400> SEQUENCE: 72

Lys Leu His Glu Leu Ser Ser Ala Leu Gly Gly Pro Gly Gly Thr Leu
1               5                   10                  15

His Asp Leu Ser Gln Ala Leu
            20

<210> SEQ ID NO 73
<211> LENGTH: 25
<212> TYPE: PRT
<213> ORGANISM: Artificial Sequence
<220> FEATURE:
<223> OTHER INFORMATION: Derived from the E7 region of HPV 31/33. GGPGG
      spacer sequence.
<220> FEATURE:
<221> NAME/KEY: misc_feature
<222> LOCATION: (10)..(10)
<223> OTHER INFORMATION: Xaa is preferably norleucine (NLE).

<400> SEQUENCE: 73

His Ile Arg Ile Leu Gln Glu Leu Leu Xaa Gly Gly Pro Gly Gly Tyr
1               5                   10                  15

Tyr Ile Val Thr Ser Ser His Thr Asp
            20                  25

<210> SEQ ID NO 74
<211> LENGTH: 25
<212> TYPE: PRT
<213> ORGANISM: Artificial Sequence
<220> FEATURE:
<223> OTHER INFORMATION: Derived from the E7 region of HPV 31/33. GGPGG
      spacer sequence.
```

```
<220> FEATURE:
<221> NAME/KEY: misc_feature
<222> LOCATION: (24)..(24)
<223> OTHER INFORMATION: Xaa is preferably norleucine (NLE).

<400> SEQUENCE: 74

His Tyr Val Leu Asp Leu Gln Pro Glu Ala Gly Gly Pro Gly Gly Leu
1               5                   10                  15

Arg Thr Ile Gln Gln Leu Leu Xaa Glu
            20                  25

<210> SEQ ID NO 75
<211> LENGTH: 25
<212> TYPE: PRT
<213> ORGANISM: Artificial Sequence
<220> FEATURE:
<223> OTHER INFORMATION: Derived from the E7 region of HPV 31/33. GGPGG
      spacer sequence.
<220> FEATURE:
<221> NAME/KEY: misc_feature
<222> LOCATION: (18)..(18)
<223> OTHER INFORMATION: Xaa is preferably norleucine (NLE).

<400> SEQUENCE: 75

Arg Thr Leu Gln Asp Tyr Val Leu Asp Leu Gly Gly Pro Gly Gly Leu
1               5                   10                  15

Leu Xaa Gly Thr Val Asn Ile Val Glu
            20                  25

<210> SEQ ID NO 76
<211> LENGTH: 25
<212> TYPE: PRT
<213> ORGANISM: Artificial Sequence
<220> FEATURE:
<223> OTHER INFORMATION: Derived from the E4 region of HPV 31/33. GGPGG
      spacer sequence.

<400> SEQUENCE: 76

Lys Trp Thr Val Ser Thr Val Gly Leu Ser Gly Gly Pro Gly Gly Val
1               5                   10                  15

Leu Gln Leu Thr Ala Gln Thr Ser Glu
            20                  25

<210> SEQ ID NO 77
<211> LENGTH: 24
<212> TYPE: PRT
<213> ORGANISM: Artificial Sequence
<220> FEATURE:
<223> OTHER INFORMATION: Derived from the E4 region of HPV 31/33. GGPGG
      spacer sequence.

<400> SEQUENCE: 77

Lys Leu Leu Ser Asp Gln Glu Gln Ser Gln Gly Gly Pro Gly Gly Leu
1               5                   10                  15

Arg Leu Tyr Leu Ala Thr Lys Asp
            20

<210> SEQ ID NO 78
<211> LENGTH: 25
<212> TYPE: PRT
<213> ORGANISM: Artificial Sequence
<220> FEATURE:
<223> OTHER INFORMATION: Derived from the E4 region of HPV 31/33. GGPGG
      spacer sequence.

<400> SEQUENCE: 78
```

```
Lys Tyr Leu Ala Val Thr Lys Tyr Pro Leu Gly Gly Pro Gly Gly Tyr
1               5                   10                  15

Leu Ala Thr Lys Tyr Pro Leu Leu Asp
            20                  25
```

<210> SEQ ID NO 79
<211> LENGTH: 23
<212> TYPE: PRT
<213> ORGANISM: Artificial Sequence
<220> FEATURE:
<223> OTHER INFORMATION: Derived from the E7 and E6 region of HPV 52.
      GGPGG spacer sequence.
<220> FEATURE:
<221> NAME/KEY: misc_feature
<222> LOCATION: (2)..(2)
<223> OTHER INFORMATION: Xaa is preferably norleucine (NLE).

<400> SEQUENCE: 79

```
Gln Xaa Leu Leu Gly Thr Leu Gln Val Gly Gly Pro Gly Gly Leu Phe
1               5                   10                  15

Thr Asp Leu Arg Ile Val Tyr
            20
```

<210> SEQ ID NO 80
<211> LENGTH: 24
<212> TYPE: PRT
<213> ORGANISM: Artificial Sequence
<220> FEATURE:
<223> OTHER INFORMATION: Derived from the E7 and E6 region of HPV 52.
      GGPGG spacer sequence.
<220> FEATURE:
<221> NAME/KEY: misc_feature
<222> LOCATION: (2)..(2)
<223> OTHER INFORMATION: Xaa is preferably norleucine (NLE).

<400> SEQUENCE: 80

```
Lys Xaa Leu Leu Gly Thr Leu Gln Val Val Gly Gly Pro Gly Gly Leu
1               5                   10                  15

Phe Thr Asp Leu Arg Ile Val Tyr
                20
```

<210> SEQ ID NO 81
<211> LENGTH: 25
<212> TYPE: PRT
<213> ORGANISM: Artificial Sequence
<220> FEATURE:
<223> OTHER INFORMATION: Derived from the E6 region of HPV 52/58. GGPGG
      spacer sequence.

<400> SEQUENCE: 81

```
Lys Leu Phe Thr Asp Leu Arg Ile Val Tyr Gly Gly Pro Gly Gly Thr
1               5                   10                  15

Leu His Asp Leu Ser Gln Ala Leu Glu
            20                  25
```

<210> SEQ ID NO 82
<211> LENGTH: 25
<212> TYPE: PRT
<213> ORGANISM: Artificial Sequence
<220> FEATURE:
<223> OTHER INFORMATION: Derived from the E6 region of HPV 52/58. GGPGG
      spacer sequence.

<400> SEQUENCE: 82

```
Lys Leu Phe Thr Asp Leu Arg Ile Val Tyr Gly Gly Pro Gly Gly Ser
1               5                   10                  15
```

-continued

```
Leu Asn Glu Ile Leu Ile Arg Ser Asp
            20                  25

<210> SEQ ID NO 83
<211> LENGTH: 24
<212> TYPE: PRT
<213> ORGANISM: Artificial Sequence
<220> FEATURE:
<223> OTHER INFORMATION: Derived from the E7 region of HPV 52. GGPGG
      spacer sequence.
<220> FEATURE:
<221> NAME/KEY: misc_feature
<222> LOCATION: (16)..(16)
<223> OTHER INFORMATION: Xaa is preferably norleucine (NLE).

<400> SEQUENCE: 83

His Tyr Ile Leu Asp Leu Gln Pro Glu Thr Gly Gly Pro Gly Gly Xaa
1               5                   10                  15

Arg Glu Asp Lys Ala Thr Ile Lys
            20

<210> SEQ ID NO 84
<211> LENGTH: 24
<212> TYPE: PRT
<213> ORGANISM: Artificial Sequence
<220> FEATURE:
<223> OTHER INFORMATION: Derived from the E7 region of HPV 52. GGPGG
      spacer sequence.
<220> FEATURE:
<221> NAME/KEY: misc_feature
<222> LOCATION: (16)..(16)
<223> OTHER INFORMATION: Xaa is preferably norleucine (NLE).

<400> SEQUENCE: 84

His Leu Arg Leu Ser Ile His Ser Thr Ala Gly Gly Pro Gly Gly Xaa
1               5                   10                  15

Arg Gly Asp Lys Ala Thr Ile Lys
            20

<210> SEQ ID NO 85
<211> LENGTH: 24
<212> TYPE: PRT
<213> ORGANISM: Artificial Sequence
<220> FEATURE:
<223> OTHER INFORMATION: Derived from the E7 region of HPV 52/58. GGPGG
      spacer sequence.
<220> FEATURE:
<221> NAME/KEY: misc_feature
<222> LOCATION: (16)..(16)
<223> OTHER INFORMATION: Xaa is preferably norleucine (NLE).

<400> SEQUENCE: 85

Lys Ile Gly Leu Asp Gly Pro Asp Gly Gln Gly Gly Pro Gly Gly Xaa
1               5                   10                  15

Arg Gly Asp Lys Ala Thr Ile Lys
            20

<210> SEQ ID NO 86
<211> LENGTH: 33
<212> TYPE: PRT
<213> ORGANISM: Artificial Sequence
<220> FEATURE:
<223> OTHER INFORMATION: Derived from the E7 region of HPV 52/58. GGPGG
      spacer sequence.
<220> FEATURE:
<221> NAME/KEY: misc_feature
<222> LOCATION: (2)..(2)
<223> OTHER INFORMATION: Xaa is preferably norleucine (NLE).
<220> FEATURE:
```

```
<221> NAME/KEY: misc_feature
<222> LOCATION: (10)..(10)
<223> OTHER INFORMATION: Xaa is preferably norleucine (NLE).

<400> SEQUENCE: 86

Lys Xaa Arg Gly Asp Lys Ala Thr Lys Xaa Arg Gly Asp Lys Ala Thr
1               5                   10                  15

Ile Lys Gly Gly Pro Gly Gly Ile Gly Leu Asp Gly Pro Asp Gly Gln
            20                  25                  30

Glu

<210> SEQ ID NO 87
<211> LENGTH: 25
<212> TYPE: PRT
<213> ORGANISM: Artificial Sequence
<220> FEATURE:
<223> OTHER INFORMATION: Derived from the E7 region of hPV 52/58. GGPGG
      spacer sequence.
<220> FEATURE:
<221> NAME/KEY: misc_feature
<222> LOCATION: (2)..(2)
<223> OTHER INFORMATION: Xaa is preferably norleucine (NLE).
<220> FEATURE:
<221> NAME/KEY: misc_feature
<222> LOCATION: (18)..(18)
<223> OTHER INFORMATION: Xaa is preferably norleucine (NLE).

<400> SEQUENCE: 87

Lys Xaa Arg Gly Asp Lys Ala Thr Ile Lys Gly Gly Pro Gly Gly Leu
1               5                   10                  15

Leu Xaa Gly Thr Ser Thr Ile Val Glu
            20                  25

<210> SEQ ID NO 88
<211> LENGTH: 25
<212> TYPE: PRT
<213> ORGANISM: Artificial Sequence
<220> FEATURE:
<223> OTHER INFORMATION: Derived from the E7 region of HPV 52/58. GGPGG
      spacer sequence.
<220> FEATURE:
<221> NAME/KEY: misc_feature
<222> LOCATION: (2)..(2)
<223> OTHER INFORMATION: Xaa is preferably norleucine (NLE).
<220> FEATURE:
<221> NAME/KEY: misc_feature
<222> LOCATION: (18)..(18)
<223> OTHER INFORMATION: Xaa is preferably norleucine (NLE).

<400> SEQUENCE: 88

His Xaa Leu Leu Gly Thr Leu Gln Val Val Gly Gly Pro Gly Gly Leu
1               5                   10                  15

Leu Xaa Gly Thr Ser Thr Ile Val Glu
            20                  25

<210> SEQ ID NO 89
<211> LENGTH: 25
<212> TYPE: PRT
<213> ORGANISM: Artificial Sequence
<220> FEATURE:
<223> OTHER INFORMATION: Derived from the E2 region of HPV 52. Met
      replaced with Nle.
<220> FEATURE:
<221> NAME/KEY: misc_feature
<222> LOCATION: (9)..(9)
<223> OTHER INFORMATION: Xaa is preferably norleucine (NLE).

<400> SEQUENCE: 89
```

Arg Val Gln Val Ile Gln Gly Val Xaa Ser Gly Gly Pro Gly Gly Leu
1               5                   10                  15

Gly Ile Val Thr Ile Thr Tyr Ser Glu
            20                  25

<210> SEQ ID NO 90
<211> LENGTH: 25
<212> TYPE: PRT
<213> ORGANISM: Artificial Sequence
<220> FEATURE:
<223> OTHER INFORMATION: Derived from the E2 region of HPV 52. GGPGG
      spacer sequence.
<220> FEATURE:
<221> NAME/KEY: misc_feature
<222> LOCATION: (9)..(9)
<223> OTHER INFORMATION: Xaa is preferably norleucine (NLE).

<400> SEQUENCE: 90

Arg Val Gln Val Ile Gln Gly Val Xaa Ser Gly Gly Pro Gly Gly Phe
1               5                   10                  15

Ser Asn Asp Ala Lys Gln Tyr Ser Asp
            20                  25

<210> SEQ ID NO 91
<211> LENGTH: 25
<212> TYPE: PRT
<213> ORGANISM: Artificial Sequence
<220> FEATURE:
<223> OTHER INFORMATION: Derived from the E2 region of HPV 52. GGPGG
      spacer sequence.

<400> SEQUENCE: 91

Lys Leu Arg Gly Gln Gln Ser Val Asp Ser Gly Gly Pro Gly Gly Leu
1               5                   10                  15

Gly Ile Val Thr Ile Thr Tyr Ser Asp
            20                  25

<210> SEQ ID NO 92
<211> LENGTH: 25
<212> TYPE: PRT
<213> ORGANISM: Artificial Sequence
<220> FEATURE:
<223> OTHER INFORMATION: Derived from the E2 region of HPV 52/58. GGPGG
      spacer sequence.

<400> SEQUENCE: 92

Lys Asn Leu Leu Arg Gly Gln Gln Ser Val Gly Gly Pro Gly Gly Val
1               5                   10                  15

Leu Phe Tyr Lys Ala Lys Glu Leu Glu
            20                  25

<210> SEQ ID NO 93
<211> LENGTH: 25
<212> TYPE: PRT
<213> ORGANISM: Artificial Sequence
<220> FEATURE:
<223> OTHER INFORMATION: Derived from the E2 regions of HPV 52 and 58.
      GGPGG spacer sequence.
<220> FEATURE:
<221> NAME/KEY: misc_feature
<222> LOCATION: (23)..(23)
<223> OTHER INFORMATION: Xaa is preferably norleucine (NLE).

<400> SEQUENCE: 93

Lys Leu Arg Gly Gln Gln Ser Val Asp Ser Gly Gly Pro Gly Gly Val
1               5                   10                  15

```
Gln Ile Ser Thr Gly Val Xaa Ser Glu
            20                  25

<210> SEQ ID NO 94
<211> LENGTH: 25
<212> TYPE: PRT
<213> ORGANISM: Artificial Sequence
<220> FEATURE:
<223> OTHER INFORMATION: Derived from the E2 regions of HPV 52 and 58.
      GGPGG spacer sequence.

<400> SEQUENCE: 94

Lys Asn Leu Leu Arg Gly Gln Gln Ser Val Gly Gly Pro Gly Gly Thr
1               5                   10                  15

Leu Gln Gln Thr Ser Leu Glu Val Glu
            20                  25

<210> SEQ ID NO 95
<211> LENGTH: 25
<212> TYPE: PRT
<213> ORGANISM: Artificial Sequence
<220> FEATURE:
<223> OTHER INFORMATION: Derived from the E4 region of HPV 58. GGPGG
      spacer sequence.

<400> SEQUENCE: 95

Lys Leu Val Ile Lys Tyr Pro Leu Leu Lys Gly Gly Pro Gly Gly Leu
1               5                   10                  15

Tyr Leu Val Ile Lys Tyr Pro Leu Glu
            20                  25

<210> SEQ ID NO 96
<211> LENGTH: 26
<212> TYPE: PRT
<213> ORGANISM: Artificial Sequence
<220> FEATURE:
<223> OTHER INFORMATION: Derived from the E4 region of HPV 58. GGPGG
      spacer sequence.

<400> SEQUENCE: 96

Lys Leu Val Ile Lys Tyr Pro Leu Leu Lys Gly Gly Pro Gly Gly Ser
1               5                   10                  15

Ile Gln Thr Ala Pro Trp Thr Thr Val Glu
            20                  25

<210> SEQ ID NO 97
<211> LENGTH: 24
<212> TYPE: PRT
<213> ORGANISM: Artificial Sequence
<220> FEATURE:
<223> OTHER INFORMATION: Derived from the E7 region of HPV 58. GGPGG
      spacer sequence.

<400> SEQUENCE: 97

His Tyr Tyr Ile Val Thr Ser Ser Tyr Thr Gly Gly Pro Gly Gly Ile
1               5                   10                  15

Gly Leu Asp Gly Pro Asp Gly Gln
            20

<210> SEQ ID NO 98
<211> LENGTH: 25
<212> TYPE: PRT
<213> ORGANISM: Artificial Sequence
<220> FEATURE:
<223> OTHER INFORMATION: Derived from the E7 region of HPV 58. GGPGG
      spacer sequence.
```

```
<220> FEATURE:
<221> NAME/KEY: misc_feature
<222> LOCATION: (4)..(4)
<223> OTHER INFORMATION: Xaa is preferably norleucine (NLE).

<400> SEQUENCE: 98

Lys Leu Leu Xaa Gly Thr Ser Thr Ile Val Gly Gly Pro Gly Gly Tyr
1               5                   10                  15

Leu Leu Asp Leu His Pro Glu Pro Asp
            20                  25

<210> SEQ ID NO 99
<211> LENGTH: 25
<212> TYPE: PRT
<213> ORGANISM: Artificial Sequence
<220> FEATURE:
<223> OTHER INFORMATION: Derived from the E6 region of HPV 58. GGPGG
      spacer sequence.

<400> SEQUENCE: 99

Lys Leu Arg Ile Val Tyr Arg Asp Gly Asn Gly Gly Pro Gly Gly Ile
1               5                   10                  15

Arg Ser Ile Ile Ser Gln Arg Pro Glu
            20                  25

<210> SEQ ID NO 100
<211> LENGTH: 25
<212> TYPE: PRT
<213> ORGANISM: Artificial Sequence
<220> FEATURE:
<223> OTHER INFORMATION: Derived from the E6 region of HPV 58. GGPGG
      spacer sequence.

<400> SEQUENCE: 100

Arg Ile Arg Ser Ile Ile Ser Gln Arg Pro Glu Gly Gly Pro Gly Gly
1               5                   10                  15

Leu Arg Leu Leu Ser Lys Ile Ser Glu
            20                  25

<210> SEQ ID NO 101
<211> LENGTH: 24
<212> TYPE: PRT
<213> ORGANISM: Artificial Sequence
<220> FEATURE:
<223> OTHER INFORMATION: Derived from the E6 region of HPV 58. GGPGG
      spacer sequence.

<400> SEQUENCE: 101

Lys Leu Arg Ile Val Tyr Arg Asp Gly Asn Gly Gly Pro Gly Gly Leu
1               5                   10                  15

Arg Leu Leu Ser Lys Ile Ser Glu
            20

<210> SEQ ID NO 102
<211> LENGTH: 24
<212> TYPE: PRT
<213> ORGANISM: Artificial Sequence
<220> FEATURE:
<223> OTHER INFORMATION: Derived from the E2 region of HPV 58. GGPGG
      spacer sequence.
<220> FEATURE:
<221> NAME/KEY: misc_feature
<222> LOCATION: (9)..(9)
<223> OTHER INFORMATION: Xaa is preferably norleucine (NLE).
<220> FEATURE:
<221> NAME/KEY: misc_feature
<222> LOCATION: (18)..(18)
```

```
<223> OTHER INFORMATION: Xaa is preferably norleucine (NLE).
<220> FEATURE:
<221> NAME/KEY: misc_feature
<222> LOCATION: (23)..(23)
<223> OTHER INFORMATION: Xaa is preferably norleucine (NLE).

<400> SEQUENCE: 102

Lys Val Gln Ile Ser Thr Gly Val Xaa Ser Gly Gly Pro Gly Gly Ile
1               5                   10                  15

Arg Xaa Glu Ser Ala Ile Xaa Tyr
            20

<210> SEQ ID NO 103
<211> LENGTH: 24
<212> TYPE: PRT
<213> ORGANISM: Artificial Sequence
<220> FEATURE:
<223> OTHER INFORMATION: Derived from the E2 region of HPV 58. GGPGG
      spacer sequence.
<220> FEATURE:
<221> NAME/KEY: misc_feature
<222> LOCATION: (9)..(9)
<223> OTHER INFORMATION: Xaa is preferably norleucine (NLE).
<220> FEATURE:
<221> NAME/KEY: misc_feature
<222> LOCATION: (16)..(16)
<223> OTHER INFORMATION: Xaa is preferably norleucine (NLE).

<400> SEQUENCE: 103

Arg Val Gln Ile Ser Thr Gly Val Xaa Ser Gly Gly Pro Gly Gly Xaa
1               5                   10                  15

Gly Ile Ser His Leu Ser His Gln
            20

<210> SEQ ID NO 104
<211> LENGTH: 25
<212> TYPE: PRT
<213> ORGANISM: Artificial Sequence
<220> FEATURE:
<223> OTHER INFORMATION: Derived from the E6 region of HPV 45. GGPGG
      spacer sequence.

<400> SEQUENCE: 104

Lys Ile Arg Ser Leu Arg Ser Gln Lys Pro Gly Gly Pro Gly Gly Val
1               5                   10                  15

Tyr Arg Asp Ser Ile Ala Tyr Ala Asp
            20                  25

<210> SEQ ID NO 105
<211> LENGTH: 24
<212> TYPE: PRT
<213> ORGANISM: Artificial Sequence
<220> FEATURE:
<223> OTHER INFORMATION: Derived from the E6 region of HPV 45. GGPGG
      spacer sequence.

<400> SEQUENCE: 105

Lys Leu Pro Asp Leu Ser Thr Glu Leu Gly Gly Pro Gly Gly Ser Leu
1               5                   10                  15

Gln Asp Val Ser Ile Ala Ser Glu
            20

<210> SEQ ID NO 106
<211> LENGTH: 25
<212> TYPE: PRT
<213> ORGANISM: Artificial Sequence
<220> FEATURE:
```

<223> OTHER INFORMATION: Derived from the E7 region of HPV 45. GGPGG
      spacer sequence.

<400> SEQUENCE: 106

Lys Leu Phe Leu Ser Thr Leu Ser Phe Val Gly Gly Pro Gly Gly Leu
1               5                   10                  15

Arg Thr Leu Gln Gln Leu Phe Leu Glu
            20                  25

<210> SEQ ID NO 107
<211> LENGTH: 24
<212> TYPE: PRT
<213> ORGANISM: Artificial Sequence
<220> FEATURE:
<223> OTHER INFORMATION: Derived from the E7 region of HPV 45. GGPGG
      spacer sequence.

<400> SEQUENCE: 107

Arg Thr Leu Gln Glu Ile Val Leu His Leu Gly Gly Pro Gly Gly Phe
1               5                   10                  15

Leu Ser Thr Leu Ser Phe Val Ser
            20

<210> SEQ ID NO 108
<211> LENGTH: 25
<212> TYPE: PRT
<213> ORGANISM: Artificial Sequence
<220> FEATURE:
<223> OTHER INFORMATION: Derived from the E6 and E7 regions of HPV 45.
      GGPGG spacer sequence.

<400> SEQUENCE: 108

Lys Leu Arg Thr Leu Gln Gln Leu Phe Leu Gly Gly Pro Gly Gly Val
1               5                   10                  15

Tyr Arg Asp Ser Ile Ala Tyr Ala Asp
            20                  25

<210> SEQ ID NO 109
<211> LENGTH: 23
<212> TYPE: PRT
<213> ORGANISM: Artificial Sequence
<220> FEATURE:
<223> OTHER INFORMATION: Derived from the E6 and E7 regions of HPV 45.
      GGPGG spacer sequence.

<400> SEQUENCE: 109

Thr Leu Gln Glu Ile Val Leu His Leu Gly Gly Pro Gly Gly Ser Leu
1               5                   10                  15

Gln Asp Val Ser Ile Ala Ser
            20

<210> SEQ ID NO 110
<211> LENGTH: 25
<212> TYPE: PRT
<213> ORGANISM: Artificial Sequence
<220> FEATURE:
<223> OTHER INFORMATION: Derived from the E2 region of HPV 45. GGPGG
      spacer sequence.

<400> SEQUENCE: 110

Lys Ile Val Arg Gln Leu Gln His Ala Ser Gly Gly Pro Gly Gly Val
1               5                   10                  15

Val Trp Asp Ser Ile Tyr Tyr Ile Glu
            20                  25

```
<210> SEQ ID NO 111
<211> LENGTH: 25
<212> TYPE: PRT
<213> ORGANISM: Artificial Sequence
<220> FEATURE:
<223> OTHER INFORMATION: Derived from the E2 region of HPV 45. GGPGG
      spacer sequence.

<400> SEQUENCE: 111

Lys Val Val Trp Asp Ser Ile Tyr Tyr Ile Gly Gly Pro Gly Gly Ser
1               5                   10                  15

Leu Ser Glu Arg Leu Ser Ala Arg Glu
            20                  25

<210> SEQ ID NO 112
<211> LENGTH: 26
<212> TYPE: PRT
<213> ORGANISM: Artificial Sequence
<220> FEATURE:
<223> OTHER INFORMATION: Derived from the E2 and E4 regions of HPV 45.
      GGPGG spacer sequence.

<400> SEQUENCE: 112

Arg Leu Arg Leu Leu Asp Ser Tyr Asn Thr Gly Gly Pro Gly Gly Lys
1               5                   10                  15

Ile Val Arg Gln Leu Gln His Ala Ser Asp
            20                  25

<210> SEQ ID NO 113
<211> LENGTH: 25
<212> TYPE: PRT
<213> ORGANISM: Artificial Sequence
<220> FEATURE:
<223> OTHER INFORMATION: Derived from the E2 and E4 regions of HPV 45.
      GGPGG spacer sequence.

<400> SEQUENCE: 113

Lys Val Val Trp Asp Ser Ile Tyr Tyr Ile Gly Gly Pro Gly Gly Arg
1               5                   10                  15

Leu Leu Ser Asp Leu Asp Ser Val Glu
            20                  25

<210> SEQ ID NO 114
<211> LENGTH: 25
<212> TYPE: PRT
<213> ORGANISM: Artificial Sequence
<220> FEATURE:
<223> OTHER INFORMATION: Derived from the E6 regions of HPV 31 and 45.
      GGPGG spacer sequence.

<400> SEQUENCE: 114

Lys Leu Arg Leu Asn Ser Val Tyr Ser Lys Gly Gly Pro Gly Gly Val
1               5                   10                  15

Tyr Arg Asp Ser Ile Ala Tyr Ala Glu
            20                  25

<210> SEQ ID NO 115
<211> LENGTH: 23
<212> TYPE: PRT
<213> ORGANISM: Artificial Sequence
<220> FEATURE:
<223> OTHER INFORMATION: Derived from the E6 regions of HPV 31 and 45.
      GGPGG spacer sequence.

<400> SEQUENCE: 115
```

-continued

Lys Leu His Glu Ser Ser Ala Leu Gly Gly Pro Gly Gly Ser Leu Gln
1               5                   10                  15

Asp Val Ser Ile Ala Ser Glu
            20

<210> SEQ ID NO 116
<211> LENGTH: 24
<212> TYPE: PRT
<213> ORGANISM: Artificial Sequence
<220> FEATURE:
<223> OTHER INFORMATION: Derived from the E7 regions of HPV 31 and 45.
      GGPGG spacer sequence.

<400> SEQUENCE: 116

His Leu Arg Leu Asn Ser Val Ser Lys Gly Gly Pro Gly Gly Val Tyr
1               5                   10                  15

Arg Asp Ser Ile Ala Tyr Ala Asp
            20

<210> SEQ ID NO 117
<211> LENGTH: 25
<212> TYPE: PRT
<213> ORGANISM: Artificial Sequence
<220> FEATURE:
<223> OTHER INFORMATION: Derived from the E7 regions of HPV 31 and 45.
      GGPGG spacer sequence.

<400> SEQUENCE: 117

His Thr Leu Gln Asp Tyr Val Leu Asp Leu Gly Gly Pro Gly Gly Thr
1               5                   10                  15

Leu Gln Glu Ile Val Leu His Leu Asp
            20                  25

<210> SEQ ID NO 118
<211> LENGTH: 25
<212> TYPE: PRT
<213> ORGANISM: Artificial Sequence
<220> FEATURE:
<223> OTHER INFORMATION: Derived from the E6 regions of HPV 16 and 58.
      GGPGG spacer sequence.

<400> SEQUENCE: 118

Lys Leu Leu Ile Arg Ser Ile Asn Ser Gln Gly Gly Pro Gly Gly Leu
1               5                   10                  15

Arg Ile Val Tyr Arg Asp Gly Asn Glu
            20                  25

<210> SEQ ID NO 119
<211> LENGTH: 25
<212> TYPE: PRT
<213> ORGANISM: Artificial Sequence
<220> FEATURE:
<223> OTHER INFORMATION: Derived from the E6 regions of HPV 16 and 58.
      GGPGG spacer sequence.

<400> SEQUENCE: 119

Lys Ile Arg Ser Ile Asn Ser Gln Lys Pro Gly Gly Pro Gly Gly Ile
1               5                   10                  15

Arg Ser Ile Ile Ser Gln Arg Pro Glu
            20                  25

<210> SEQ ID NO 120
<211> LENGTH: 24
<212> TYPE: PRT
<213> ORGANISM: Artificial Sequence

```
<220> FEATURE:
<223> OTHER INFORMATION: Derived from the E6 regions of HPV 16 and 58.
      GGPGG spacer sequence.

<400> SEQUENCE: 120

Lys Val Tyr Arg Asp Gly Asn Pro Tyr Ala Gly Gly Pro Gly Gly Leu
1               5                   10                  15

Arg Leu Leu Ser Lys Ile Ser Glu
            20

<210> SEQ ID NO 121
<211> LENGTH: 25
<212> TYPE: PRT
<213> ORGANISM: Artificial Sequence
<220> FEATURE:
<223> OTHER INFORMATION: Derived from the E6 regions of HPV 16 and 58.
      GGPGG spacer sequence.

<400> SEQUENCE: 121

Lys Val Tyr Arg Asp Gly Asn Pro Tyr Ala Gln Gly Gly Pro Gly Gly
1               5                   10                  15

Leu Arg Ile Val Tyr Arg Asp Gly Asn
            20                  25

<210> SEQ ID NO 122
<211> LENGTH: 24
<212> TYPE: PRT
<213> ORGANISM: Artificial Sequence
<220> FEATURE:
<223> OTHER INFORMATION: Derived from the E6 regions of HPV 16 and 58.
      GGPGG spacer sequence.

<400> SEQUENCE: 122

Lys Ile Ser Glu Tyr Arg His Tyr Ser Gly Gly Pro Gly Gly Thr Leu
1               5                   10                  15

His Asp Leu Ser Gln Ala Leu Glu
            20

<210> SEQ ID NO 123
<211> LENGTH: 25
<212> TYPE: PRT
<213> ORGANISM: Artificial Sequence
<220> FEATURE:
<223> OTHER INFORMATION: Derived from the E6 region of HPV 6. GGPGG
      spacer sequence.

<400> SEQUENCE: 123

His Leu Gln Ile Asn Ser Val Phe Ser Lys Gly Gly Pro Gly Gly Phe
1               5                   10                  15

Arg Gly Gly Tyr Pro Tyr Ala Ala Glu
            20                  25

<210> SEQ ID NO 124
<211> LENGTH: 25
<212> TYPE: PRT
<213> ORGANISM: Artificial Sequence
<220> FEATURE:
<223> OTHER INFORMATION: Derived from the E6 region of HPV 6. GGPGG
      spacer sequence.
<220> FEATURE:
<221> NAME/KEY: misc_feature
<222> LOCATION: (19)..(19)
<223> OTHER INFORMATION: Xaa is preferably norleucine (NLE).

<400> SEQUENCE: 124

Arg Leu Gln Ile Asn Ser Val Phe Ser Lys Gly Gly Pro Gly Gly Asn
```

```
                1               5                  10                 15
Leu Ser Xaa His Thr Leu Gln Ile Glu
                20                 25

<210> SEQ ID NO 125
<211> LENGTH: 25
<212> TYPE: PRT
<213> ORGANISM: Artificial Sequence
<220> FEATURE:
<223> OTHER INFORMATION: Derived from the E7 region of HPV 6. GGPGG
      spacer sequence.

<400> SEQUENCE: 125

Arg Ile Val Leu Asp Leu Gln Pro Pro Asp Gly Gly Pro Gly Gly Leu
1               5                  10                 15
Asn Ile Val Ser Pro Ile Ser Ala Glu
                20                 25

<210> SEQ ID NO 126
<211> LENGTH: 25
<212> TYPE: PRT
<213> ORGANISM: Artificial Sequence
<220> FEATURE:
<223> OTHER INFORMATION: Derived from the E7 region of HPV 6. GGPGG
      spacer sequence.

<400> SEQUENCE: 126

Arg Leu Asn Ile Val Ser Pro Ile Ser Ala Gly Gly Pro Gly Gly Leu
1               5                  10                 15
Leu Leu Gly Thr Leu Asn Ile Val Glu
                20                 25

<210> SEQ ID NO 127
<211> LENGTH: 24
<212> TYPE: PRT
<213> ORGANISM: Artificial Sequence
<220> FEATURE:
<223> OTHER INFORMATION: Derived from the E7 region of HPV 6. GGPGG
      spacer sequence.

<400> SEQUENCE: 127

Lys Leu Leu Leu Gly Thr Leu Asn Ile Val Gly Gly Pro Gly Gly Leu
1               5                  10                 15
His Ser Tyr Glu Gln Leu Val Glu
                20

<210> SEQ ID NO 128
<211> LENGTH: 25
<212> TYPE: PRT
<213> ORGANISM: Artificial Sequence
<220> FEATURE:
<223> OTHER INFORMATION: Derived from the E2 region of HPV 6. GGPGG
      spacer sequence.

<400> SEQUENCE: 128

Arg Tyr Arg Leu Asn Asp Lys His Arg His Gly Gly Pro Gly Gly Ile
1               5                  10                 15
Arg His Glu Ser Val Leu Leu Tyr Asp
                20                 25

<210> SEQ ID NO 129
<211> LENGTH: 24
<212> TYPE: PRT
<213> ORGANISM: Artificial Sequence
<220> FEATURE:
```

```
<223> OTHER INFORMATION: Derived from the E2 region of HPV 6. GGPGG
      spacer sequence.

<400> SEQUENCE: 129

His Val Gln Gln Ser Pro Ser Asn Ala Leu Gly Gly Pro Gly Gly Val
1               5                   10                  15

Lys Phe Asp Gly Ser Ala Asn Asn
            20

<210> SEQ ID NO 130
<211> LENGTH: 25
<212> TYPE: PRT
<213> ORGANISM: Artificial Sequence
<220> FEATURE:
<223> OTHER INFORMATION: Derived from the E2 region of HPV 6. GGPGG
      spacer sequence.

<400> SEQUENCE: 130

Lys Tyr Val Gln Asp Thr Asp Ser Trp Val Gly Gly Pro Gly Gly Tyr
1               5                   10                  15

Val Val Trp Thr Asp Val Tyr Val Glu
            20                  25

<210> SEQ ID NO 131
<211> LENGTH: 25
<212> TYPE: PRT
<213> ORGANISM: Artificial Sequence
<220> FEATURE:
<223> OTHER INFORMATION: Derived from the E4 region of HPV 6. GGPGG
      spacer sequence.

<400> SEQUENCE: 131

Lys Tyr Val Leu Leu His Leu Tyr Leu Ala Gly Gly Pro Gly Gly Leu
1               5                   10                  15

Ala Leu His Lys Lys Tyr Pro Phe Glu
            20                  25

<210> SEQ ID NO 132
<211> LENGTH: 25
<212> TYPE: PRT
<213> ORGANISM: Artificial Sequence
<220> FEATURE:
<223> OTHER INFORMATION: Derived from the E4 region of HPV 6. GGPGG
      spacer sequence.
<220> FEATURE:
<221> NAME/KEY: misc_feature
<222> LOCATION: (4)..(4)
<223> OTHER INFORMATION: Xaa is preferably norleucine (NLE).

<400> SEQUENCE: 132

Lys Tyr Val Xaa Ala Ala Gln Leu Tyr Val Gly Gly Pro Gly Gly Val
1               5                   10                  15

Leu Leu His Leu Tyr Leu Ala Leu Asp
            20                  25

<210> SEQ ID NO 133
<211> LENGTH: 25
<212> TYPE: PRT
<213> ORGANISM: Artificial Sequence
<220> FEATURE:
<223> OTHER INFORMATION: Derived from the E6 region of HPV 11. GPGPG
      spacer sequence.

<400> SEQUENCE: 133

Lys Leu Gln Ile Asn Ser Val Phe Ser Arg Gly Pro Gly Pro Gly Ile
1               5                   10                  15
```

```
Gln Ser Val Phe Ser Arg Asn Ala Glu
            20                  25

<210> SEQ ID NO 134
<211> LENGTH: 26
<212> TYPE: PRT
<213> ORGANISM: Artificial Sequence
<220> FEATURE:
<223> OTHER INFORMATION: Derived from the E6 region of HPV 11. GPGPG
      spacer sequence.

<400> SEQUENCE: 134

Lys Thr Leu Gln Ile Gln Ser Val Phe Ser Arg Gly Pro Gly Pro Gly
1               5                   10                  15

Asn Gln Tyr Arg His Phe Asn Tyr Ala Asp
            20                  25

<210> SEQ ID NO 135
<211> LENGTH: 25
<212> TYPE: PRT
<213> ORGANISM: Artificial Sequence
<220> FEATURE:
<223> OTHER INFORMATION: Derived from the E6 regions of HPV 6 and 11.
      GPGPG spacer sequence.

<400> SEQUENCE: 135

Lys Leu Gln Ile Asn Ser Val Phe Ser Arg Gly Pro Gly Pro Gly Leu
1               5                   10                  15

Gln Ile Gln Ser Val Phe Ser Lys Asp
            20                  25

<210> SEQ ID NO 136
<211> LENGTH: 26
<212> TYPE: PRT
<213> ORGANISM: Artificial Sequence
<220> FEATURE:
<223> OTHER INFORMATION: Derived from the E7 region of HPV 11. GPGPG
      spacer sequence.

<400> SEQUENCE: 136

His Leu Asn Ile Val Ser Pro Ile Ser Ala Gly Pro Gly Pro Gly Tyr
1               5                   10                  15

Gln Ile Leu Thr Ser Ser Ser Gly Ser Asp
            20                  25

<210> SEQ ID NO 137
<211> LENGTH: 25
<212> TYPE: PRT
<213> ORGANISM: Artificial Sequence
<220> FEATURE:
<223> OTHER INFORMATION: Derived from the E7 region of HPV 11. GPGPG
      spacer sequence.

<400> SEQUENCE: 137

Arg Leu Leu Leu Gly Thr Leu Asn Ile Val Gly Pro Gly Pro Gly Gln
1               5                   10                  15

Leu Gln Asp Leu Leu Leu Gly Thr Glu
            20                  25

<210> SEQ ID NO 138
<211> LENGTH: 25
<212> TYPE: PRT
<213> ORGANISM: Artificial Sequence
<220> FEATURE:
<223> OTHER INFORMATION: Derived from the E7 regions of HPV 6 and 11.
```

GPGPG spacer sequence.

<400> SEQUENCE: 138

His Ile Val Leu Asp Leu Gln Pro Pro Asp Gly Pro Gly Pro Gly Leu
1               5                   10                  15

Asn Ile Val Ser Pro Ile Ser Ala Glu
            20                  25

<210> SEQ ID NO 139
<211> LENGTH: 24
<212> TYPE: PRT
<213> ORGANISM: Artificial Sequence
<220> FEATURE:
<223> OTHER INFORMATION: Derived from the E7 regions of HPV 6 and 11.
      GGPGG spacer sequence.

<400> SEQUENCE: 139

Lys Leu Asn Ile Val Ser Pro Ile Ser Ala Gly Gly Pro Gly Gly Ile
1               5                   10                  15

Val Leu Asp Leu Gln Pro Pro Asp
            20

<210> SEQ ID NO 140
<211> LENGTH: 24
<212> TYPE: PRT
<213> ORGANISM: Artificial Sequence
<220> FEATURE:
<223> OTHER INFORMATION: Derived from the E7 regions of HPV 6 and 11.
      GGPGG spacer sequence.

<400> SEQUENCE: 140

His Leu Leu Leu Gly Thr Leu Asn Ile Val Gly Gly Pro Gly Gly Leu
1               5                   10                  15

His Ser Tyr Glu Gln Leu Glu Asp
            20

<210> SEQ ID NO 141
<211> LENGTH: 25
<212> TYPE: PRT
<213> ORGANISM: Artificial Sequence
<220> FEATURE:
<223> OTHER INFORMATION: Derived from the E2 region of HPV 11. GGPGG
      spacer sequence.

<400> SEQUENCE: 141

Lys Tyr Arg Leu Asn Asp Lys Tyr Lys His Gly Gly Pro Gly Gly Ile
1               5                   10                  15

Arg Leu Glu Ser Val Leu Leu His Glu
            20                  25

<210> SEQ ID NO 142
<211> LENGTH: 25
<212> TYPE: PRT
<213> ORGANISM: Artificial Sequence
<220> FEATURE:
<223> OTHER INFORMATION: Derived from the E2 region of HPV 11. GGPGG
      spacer sequence.

<400> SEQUENCE: 142

Arg Val Lys Phe Asp Gly Ser Glu Asp Asn Gly Gly Pro Gly Gly Lys
1               5                   10                  15

Tyr Arg Leu Asn Asp Lys Tyr Lys Glu
            20                  25

```
<210> SEQ ID NO 143
<211> LENGTH: 25
<212> TYPE: PRT
<213> ORGANISM: Artificial Sequence
<220> FEATURE:
<223> OTHER INFORMATION: Derived from the E2 region of HPV 11. GGPGG
      spacer sequence.

<400> SEQUENCE: 143

Lys Ile Arg Leu Glu Ser Val Leu Leu His Gly Gly Pro Gly Gly Tyr
1               5                   10                  15

Val Asn Phe Asn Lys Glu Ala Gln Asp
            20                  25

<210> SEQ ID NO 144
<211> LENGTH: 25
<212> TYPE: PRT
<213> ORGANISM: Artificial Sequence
<220> FEATURE:
<223> OTHER INFORMATION: Derived from the E2 region of HPV 11. GGPGG
      spacer sequence.
<220> FEATURE:
<221> NAME/KEY: misc_feature
<222> LOCATION: (20)..(20)
<223> OTHER INFORMATION: Xaa is preferably norleucine (NLE).
<220> FEATURE:
<221> NAME/KEY: misc_feature
<222> LOCATION: (22)..(22)
<223> OTHER INFORMATION: Xaa is preferably norleucine (NLE).

<400> SEQUENCE: 144

His Tyr Val Gln Asp Thr Asp Ser Trp Val Gly Gly Pro Gly Gly Lys
1               5                   10                  15

Leu Gly Phe Xaa Ser Xaa His Leu Glu
            20                  25

<210> SEQ ID NO 145
<211> LENGTH: 25
<212> TYPE: PRT
<213> ORGANISM: Artificial Sequence
<220> FEATURE:
<223> OTHER INFORMATION: Derived from the E2 region of HPV 6 and 11.
      GGPGG spacer sequence.

<400> SEQUENCE: 145

Arg Val Lys Phe Asp Gly Ser Glu Asp Asn Gly Gly Pro Gly Gly Val
1               5                   10                  15

Lys Phe Asp Gly Ser Ala Asn Asn Asp
            20                  25

<210> SEQ ID NO 146
<211> LENGTH: 26
<212> TYPE: PRT
<213> ORGANISM: Artificial Sequence
<220> FEATURE:
<223> OTHER INFORMATION: Derived from the E2 region of HPV 6 and 11.
      GGPGG spacer sequence.

<400> SEQUENCE: 146

His Tyr Leu Asp Asn Asp Ser Trp Val Gly Gly Pro Gly Gly Lys Leu
1               5                   10                  15

Gly Tyr Val Gln Asp Thr Asp Ser Trp Glu
            20                  25

<210> SEQ ID NO 147
<211> LENGTH: 25
<212> TYPE: PRT
```

```
<213> ORGANISM: Artificial Sequence
<220> FEATURE:
<223> OTHER INFORMATION: Derived from the E4 region of HPV 11. GGPGG
      spacer sequence.

<400> SEQUENCE: 147

His Tyr Val Leu Leu His Leu Tyr Leu Ala Gly Gly Pro Gly Gly Val
1               5                   10                  15

Val Pro Ile Ile Gly Lys Tyr Val Asp
            20                  25

<210> SEQ ID NO 148
<211> LENGTH: 25
<212> TYPE: PRT
<213> ORGANISM: Artificial Sequence
<220> FEATURE:
<223> OTHER INFORMATION: Derived from the E4 region of HPV 11. GGPGG
      spacer sequence.

<400> SEQUENCE: 148

His Val Val Pro Ile Ile Gly Lys Tyr Val Gly Gly Pro Gly Gly Leu
1               5                   10                  15

Asn Leu Leu His Thr Pro Pro His Asp
            20                  25

<210> SEQ ID NO 149
<211> LENGTH: 25
<212> TYPE: PRT
<213> ORGANISM: Artificial Sequence
<220> FEATURE:
<223> OTHER INFORMATION: Derived from the E4 region of HPV 11. GGPGG
      spacer sequence.

<400> SEQUENCE: 149

Lys Ala Leu Tyr Glu Lys Tyr Pro Leu Leu Gly Gly Pro Gly Gly Val
1               5                   10                  15

Leu Leu His Leu Tyr Leu Ala Leu Glu
            20                  25

<210> SEQ ID NO 150
<211> LENGTH: 25
<212> TYPE: PRT
<213> ORGANISM: Artificial Sequence
<220> FEATURE:
<223> OTHER INFORMATION: Derived from the E4 regions of HPV 6 and 11.
      GGPGG spacer sequence.

<400> SEQUENCE: 150

Lys Tyr Val Leu Leu His Leu Tyr Leu Ala Gly Gly Pro Gly Gly Leu
1               5                   10                  15

Ala Leu His Lys Lys Tyr Pro Phe Asp
            20                  25

<210> SEQ ID NO 151
<211> LENGTH: 25
<212> TYPE: PRT
<213> ORGANISM: Artificial Sequence
<220> FEATURE:
<223> OTHER INFORMATION: Derived from the E4 regions of HPV 6 and 11.
      GGPGG spacer sequence.
<220> FEATURE:
<221> NAME/KEY: misc_feature
<222> LOCATION: (18)..(18)
<223> OTHER INFORMATION: Xaa is preferably norleucine (NLE).

<400> SEQUENCE: 151
```

```
Lys Ala Leu Tyr Glu Lys Tyr Pro Leu Leu Gly Gly Pro Gly Gly Tyr
1               5                   10                  15

Val Xaa Ala Ala Gln Leu Tyr Val Glu
            20                  25
```

<210> SEQ ID NO 152
<211> LENGTH: 25
<212> TYPE: PRT
<213> ORGANISM: Artificial Sequence
<220> FEATURE:
<223> OTHER INFORMATION: Derived from the H-Ras protein and the E4 region of HPV 16. GGPGG spacer sequence.

<400> SEQUENCE: 152

```
Lys Val Val Ile Asp Gly Glu Thr Ser Leu Gly Gly Pro Gly Gly Leu
1               5                   10                  15

Gln Ser Ser Leu His Leu Thr Ala Glu
            20                  25
```

<210> SEQ ID NO 153
<211> LENGTH: 25
<212> TYPE: PRT
<213> ORGANISM: Artificial Sequence
<220> FEATURE:
<223> OTHER INFORMATION: Derived from the H-Ras protein and the E4 region of HPV 16. GGPGG spacer sequence.

<400> SEQUENCE: 153

```
Lys Phe Ala Ile Asn Asn Thr Lys Ser Phe Gly Gly Pro Gly Gly Tyr
1               5                   10                  15

Val Leu His Leu Ser Leu Ala Ala Asp
            20                  25
```

<210> SEQ ID NO 154
<211> LENGTH: 26
<212> TYPE: PRT
<213> ORGANISM: Artificial Sequence
<220> FEATURE:
<223> OTHER INFORMATION: Derived from the H-Ras protein and the E4 region of HPV 16. GGPGG spacer sequence.

<400> SEQUENCE: 154

```
Lys Ile Gln Leu Ile Gln Asn His Phe Val Gly Gly Pro Gly Gly Lys
1               5                   10                  15

Ile Ser Glu Tyr Arg His Tyr Ser Arg Glu
            20                  25
```

<210> SEQ ID NO 155
<211> LENGTH: 27
<212> TYPE: PRT
<213> ORGANISM: Artificial Sequence
<220> FEATURE:
<223> OTHER INFORMATION: Derived from the H-Ras protein and the E4 region of HPV 33. GGPGG spacer sequence.

<400> SEQUENCE: 155

```
Lys Val Val Ile Asp Gly Glu Thr Ser Leu Gly Gln Gly Gly Pro Gly
1               5                   10                  15

Gly Val Leu Gln Leu Thr Ala Gln Thr Ser Glu
            20                  25
```

<210> SEQ ID NO 156
<211> LENGTH: 25
<212> TYPE: PRT
<213> ORGANISM: Artificial Sequence

```
<220> FEATURE:
<223> OTHER INFORMATION: Derived from the H-Ras protein and the E4
      region of HPV 33. GGPGG spacer sequence.

<400> SEQUENCE: 156

Lys Val Val Ile Asp Gly Glu Thr Ser Leu Gly Gly Pro Gly Gly Tyr
1               5                   10                  15

Leu Ala Thr Lys Tyr Pro Leu Leu Glu
            20                  25

<210> SEQ ID NO 157
<211> LENGTH: 23
<212> TYPE: PRT
<213> ORGANISM: Artificial Sequence
<220> FEATURE:
<223> OTHER INFORMATION: Derived from the H-Ras protein and the E4
      region of HPV 33. GGPGG spacer sequence.

<400> SEQUENCE: 157

His Ile Gln Leu Ile Asn His Phe Val Gly Gly Pro Gly Gly Leu Ala
1               5                   10                  15

Thr Lys Tyr Pro Leu Leu Asp
            20

<210> SEQ ID NO 158
<211> LENGTH: 25
<212> TYPE: PRT
<213> ORGANISM: Artificial Sequence
<220> FEATURE:
<223> OTHER INFORMATION: Derived from the H-Ras protein and the E4
      region of HPV 58. GGPGG spacer sequence.

<400> SEQUENCE: 158

Lys Phe Leu Ser His Asp Thr Asp Leu Ser Gly Gly Pro Gly Gly Leu
1               5                   10                  15

Val Ile Lys Tyr Pro Leu Leu Lys Asp
            20                  25

<210> SEQ ID NO 159
<211> LENGTH: 25
<212> TYPE: PRT
<213> ORGANISM: Artificial Sequence
<220> FEATURE:
<223> OTHER INFORMATION: Derived from the H-Ras protein and the E4
      region of HPV 45. GGPGG spacer sequence.

<400> SEQUENCE: 159

Lys Val Val Ile Asp Gly Glu Thr Ser Leu Gly Gly Pro Gly Gly Ile
1               5                   10                  15

Val Arg Gln Leu Gln His Ala Ser Glu
            20                  25

<210> SEQ ID NO 160
<211> LENGTH: 25
<212> TYPE: PRT
<213> ORGANISM: Artificial Sequence
<220> FEATURE:
<223> OTHER INFORMATION: Derived from the H-Ras protein and the E4
      region of HPV 45. GGPGG spacer sequence.

<400> SEQUENCE: 160

Lys Phe Ala Ile Asn Asn Thr Lys Ser Phe Gly Gly Pro Gly Gly Arg
1               5                   10                  15

Leu Leu Ser Asp Leu Asp Ser Val Glu
            20                  25
```

<210> SEQ ID NO 161
<211> LENGTH: 25
<212> TYPE: PRT
<213> ORGANISM: Artificial Sequence
<220> FEATURE:
<223> OTHER INFORMATION: Derived from the H-Ras protein and the E4
      region of HPV 45. GGPGG spacer sequence.

<400> SEQUENCE: 161

Lys Val Gly Ala Gly Gly Val Gly Lys Ser Gly Gly Pro Gly Gly Leu
1               5                   10                  15

Arg Leu Leu Asp Ser Tyr Asn Thr Glu
            20                  25

<210> SEQ ID NO 162
<211> LENGTH: 25
<212> TYPE: PRT
<213> ORGANISM: Artificial Sequence
<220> FEATURE:
<223> OTHER INFORMATION: Derived from the H-Ras protein and the E4
      region of HPV 45. GGPGG spacer sequence.

<400> SEQUENCE: 162

Arg Ile Gln Leu Ile Gln Asn His Phe Val Gly Gly Pro Gly Gly Arg
1               5                   10                  15

Leu Leu Ser Asp Leu Asp Ser Val Glu
            20                  25

<210> SEQ ID NO 163
<211> LENGTH: 25
<212> TYPE: PRT
<213> ORGANISM: Artificial Sequence
<220> FEATURE:
<223> OTHER INFORMATION: Derived from the H-Ras protein and the E2
      region of HPV 31. GGPGG spacer sequence.

<400> SEQUENCE: 163

Lys Leu Asp Ile Leu Asp Thr Ala Gly Gln Gly Gly Pro Gly Gly Leu
1               5                   10                  15

Leu Arg Gly Asp Ser Val Asp Ser Glu
            20                  25

<210> SEQ ID NO 164
<211> LENGTH: 25
<212> TYPE: PRT
<213> ORGANISM: Artificial Sequence
<220> FEATURE:
<223> OTHER INFORMATION: Derived from the K-Ras protein and the E2
      region of HPV 16. GGPGG spacer sequence.
<220> FEATURE:
<221> NAME/KEY: misc_feature
<222> LOCATION: (16)..(16)
<223> OTHER INFORMATION: Xaa is preferably norleucine (NLE).

<400> SEQUENCE: 164

Lys Phe Leu Ser His Asp Thr Asp Leu Ser Gly Gly Pro Gly Gly Xaa
1               5                   10                  15

Arg Leu Glu Ser Ala Ile Tyr Tyr Glu
            20                  25

<210> SEQ ID NO 165
<211> LENGTH: 25
<212> TYPE: PRT
<213> ORGANISM: Artificial Sequence
<220> FEATURE:

```
<223> OTHER INFORMATION: Derived from the K-Ras protein and the E2
      region of HPV 16. GGPGG spacer sequence.

<400> SEQUENCE: 165

His Ile Gln Leu Ile Gln Asn His Phe Val Gly Gly Pro Gly Gly Thr
1               5                   10                  15

Leu Gln Asp Val Ser Leu Glu Val Glu
            20                  25

<210> SEQ ID NO 166
<211> LENGTH: 25
<212> TYPE: PRT
<213> ORGANISM: Artificial Sequence
<220> FEATURE:
<223> OTHER INFORMATION: Derived from the K-Ras protein and the E5
      region of HPV 16. GGPGG spacer sequence.

<400> SEQUENCE: 166

Lys Phe Leu Ser His Asp Thr Asp Leu Ser Gly Gly Pro Gly Gly Phe
1               5                   10                  15

Val Tyr Ile Pro Leu Phe Leu Ile Glu
            20                  25

<210> SEQ ID NO 167
<211> LENGTH: 25
<212> TYPE: PRT
<213> ORGANISM: Artificial Sequence
<220> FEATURE:
<223> OTHER INFORMATION: Derived from the K-Ras protein and the E5
      region of HPV 16. GGPGG spacer sequence.

<400> SEQUENCE: 167

Arg Ser Leu Ala Ser Thr Ala Asp Thr Ile Gly Gly Pro Gly Gly Phe
1               5                   10                  15

Val Tyr Ile Pro Leu Phe Leu Ile Glu
            20                  25

<210> SEQ ID NO 168
<211> LENGTH: 25
<212> TYPE: PRT
<213> ORGANISM: Artificial Sequence
<220> FEATURE:
<223> OTHER INFORMATION: Derived from the K-Ras protein and the E4
      region of HPV 18. GGPGG spacer sequence.

<400> SEQUENCE: 168

Lys Leu Pro Gly Asp Thr Asp Leu Phe Leu Gly Gly Pro Gly Gly Leu
1               5                   10                  15

Ser Leu Leu Asn Ser Tyr Ser Thr Asp
            20                  25

<210> SEQ ID NO 169
<211> LENGTH: 25
<212> TYPE: PRT
<213> ORGANISM: Artificial Sequence
<220> FEATURE:
<223> OTHER INFORMATION: Derived from the K-Ras protein and the E4
      region of HPV 18. GGPGG spacer sequence.

<400> SEQUENCE: 169

Lys Thr Leu Gly Asp Thr Asp Ser Asn Thr Gly Gly Pro Gly Gly Arg
1               5                   10                  15

Leu Leu His Asp Leu Asp Thr Val Glu
            20                  25
```

```
<210> SEQ ID NO 170
<211> LENGTH: 25
<212> TYPE: PRT
<213> ORGANISM: Artificial Sequence
<220> FEATURE:
<223> OTHER INFORMATION: Derived from the CHSP60 protein. GGPGG
      spacer sequence.

<400> SEQUENCE: 170

Lys Leu Gln Glu Arg Leu Ala Lys Leu Glu Gly Gly Pro Gly Gly Ile
1               5                   10                  15

Arg Ser Ile Pro Thr Leu Glu Ala Asp
            20                  25

<210> SEQ ID NO 171
<211> LENGTH: 23
<212> TYPE: PRT
<213> ORGANISM: Artificial Sequence
<220> FEATURE:
<223> OTHER INFORMATION: Derived from the CHSP60 protein. GPG
      spacer sequence.

<400> SEQUENCE: 171

Lys Val Val Ile Asp Lys Ser Phe Gly Ser Gly Pro Gly Val Leu Ile
1               5                   10                  15

Tyr Asp Lys Lys Ile Ser Glu
            20

<210> SEQ ID NO 172
<211> LENGTH: 24
<212> TYPE: PRT
<213> ORGANISM: Artificial Sequence
<220> FEATURE:
<223> OTHER INFORMATION: Derived from the CHSP60 protein. GGPGG
      spacer sequence.

<400> SEQUENCE: 172

Lys Leu Gln Glu Arg Leu Ala Lys Leu Gly Gly Pro Gly Gly Leu Ile
1               5                   10                  15

Tyr Asp Lys Lys Ile Ser Gly Asp
            20

<210> SEQ ID NO 173
<211> LENGTH: 25
<212> TYPE: PRT
<213> ORGANISM: Artificial Sequence
<220> FEATURE:
<223> OTHER INFORMATION: Derived from the CHSP60 protein. GGPGG spacer
      sequence.
<220> FEATURE:
<221> NAME/KEY: misc_feature
<222> LOCATION: (8)..(8)
<223> OTHER INFORMATION: Xaa is preferably norleucine (NLE).

<400> SEQUENCE: 173

Lys Ile Ile Phe Gln Gln Val Xaa Ser Arg Gly Gly Pro Gly Gly Asn
1               5                   10                  15

Ile Lys Tyr Asn Glu Glu Ala Arg Asp
            20                  25

<210> SEQ ID NO 174
<211> LENGTH: 25
<212> TYPE: PRT
<213> ORGANISM: Artificial Sequence
<220> FEATURE:
<223> OTHER INFORMATION: Derived from the PTEN protein. GPGPG spacer
``` sequence.

<400> SEQUENCE: 174

Arg Tyr Leu Leu His Arg Gly Lys Phe Leu Gly Pro Gly Pro Gly Tyr
1               5                   10                  15

Arg Tyr Ser Asp Thr Thr Asp Ser Glu
            20                  25

<210> SEQ ID NO 175
<211> LENGTH: 23
<212> TYPE: PRT
<213> ORGANISM: Artificial Sequence
<220> FEATURE:
<223> OTHER INFORMATION: Derived from the PTEN protein. GPG spacer
      sequence.

<400> SEQUENCE: 175

Asp Ile Val Ser Arg Asn Lys Arg Arg Tyr Gly Pro Gly Tyr Val Tyr
1               5                   10                  15

Tyr Tyr Ser Tyr Leu Leu Glu
            20

<210> SEQ ID NO 176
<211> LENGTH: 22
<212> TYPE: PRT
<213> ORGANISM: Artificial Sequence
<220> FEATURE:
<223> OTHER INFORMATION: Derived from the PTEN protein. GPG spacer
      sequence.

<400> SEQUENCE: 176

Lys Trp Leu Ser Glu Asp Asp Asn His Val Gly Pro Gly Tyr Arg Pro
1               5                   10                  15

Val Ala Leu Leu Arg Asp
            20

<210> SEQ ID NO 177
<211> LENGTH: 31
<212> TYPE: PRT
<213> ORGANISM: Artificial Sequence
<220> FEATURE:
<223> OTHER INFORMATION: Derived from the CHSP60 protein and the E7
      region of HPV 18. GGPGG spacer sequence.

<400> SEQUENCE: 177

Lys Leu Gln Glu Arg Leu Ala Lys Leu Gly Gly Pro Gly Gly Asp Ser
1               5                   10                  15

Glu Glu Glu Asn Asp Glu Ile Gly Asp Val Asn His Gln His Asp
            20                  25                  30

<210> SEQ ID NO 178
<211> LENGTH: 29
<212> TYPE: PRT
<213> ORGANISM: Artificial Sequence
<220> FEATURE:
<223> OTHER INFORMATION: Derived from the CHSP60 protein and the E7
      region of HPV 16. GGPGG spacer sequence.
<220> FEATURE:
<221> NAME/KEY: misc_feature
<222> LOCATION: (17)..(17)
<223> OTHER INFORMATION: Xaa is preferably norleucine (NLE).

<400> SEQUENCE: 178

Lys Leu Gln Glu Arg Leu Ala Lys Leu Gly Gly Pro Gly Gly Leu Leu
1               5                   10                  15

Xaa Gly Thr Leu Gly Ile Val Ser Pro Ile Ser Ser Glu
            20                  25

<210> SEQ ID NO 179
<211> LENGTH: 40
<212> TYPE: PRT
<213> ORGANISM: Artificial Sequence
<220> FEATURE:
<223> OTHER INFORMATION: Derived from the CHSP60 protein and the E6
      region of HPV 16. GPG spacer sequence.
<220> FEATURE:
<221> NAME/KEY: misc_feature
<222> LOCATION: (14)..(14)
<223> OTHER INFORMATION: Xaa is preferably norleucine (NLE).
<220> FEATURE:
<221> NAME/KEY: misc_feature
<222> LOCATION: (21)..(21)
<223> OTHER INFORMATION: Xaa is preferably norleucine (NLE).

<400> SEQUENCE: 179

Lys Leu Gln Glu Arg Leu Ala Lys Leu Gly Pro Gly Lys Xaa His Gln
1               5                   10                  15

Lys Arg Thr Ala Xaa Phe Gln Asp Pro Gln Glu Arg Pro Arg Lys Leu
            20                  25                  30

Pro Gln Leu Ser Thr Glu Leu Asp
        35                  40

<210> SEQ ID NO 180
<211> LENGTH: 25
<212> TYPE: PRT
<213> ORGANISM: Artificial Sequence
<220> FEATURE:
<223> OTHER INFORMATION: Derived from the CHSP60 protein and the E7
      region of HPV 16. GGPGG spacer sequence.

<400> SEQUENCE: 180

Lys Leu Gln Glu Arg Leu Ala Lys Gly Gly Pro Gly Gly Leu Asn Asp
1               5                   10                  15

Ser Ser Glu Glu Glu Asp Glu Ile Asp
            20                  25

<210> SEQ ID NO 181
<211> LENGTH: 40
<212> TYPE: PRT
<213> ORGANISM: Artificial Sequence
<220> FEATURE:
<223> OTHER INFORMATION: Derived from the CHSP60 protein and the E7
      region of HPV 58/16. GPG spacer sequence.
<220> FEATURE:
<221> NAME/KEY: misc_feature
<222> LOCATION: (8)..(8)
<223> OTHER INFORMATION: Xaa is preferably norleucine (NLE).
<220> FEATURE:
<221> NAME/KEY: misc_feature
<222> LOCATION: (28)..(28)
<223> OTHER INFORMATION: Xaa is preferably norleucine (NLE).

<400> SEQUENCE: 181

Lys Ile Ile Phe Gln Gln Val Xaa Ser Arg Gly Pro Gly Ile Gly Leu
1               5                   10                  15

Asp Gly Pro Asp Gly Gln Gly Pro Gly Leu Leu Xaa Gly Thr Leu Gly
            20                  25                  30

Ile Val Ser Pro Ile Ser Ser Glu
        35                  40

<210> SEQ ID NO 182
<211> LENGTH: 30

-continued

```
<212> TYPE: PRT
<213> ORGANISM: Artificial Sequence
<220> FEATURE:
<223> OTHER INFORMATION: Derived from the CHSP60 protein and the E7
      region of HPV 58. GPG spacer sequence.
<220> FEATURE:
<221> NAME/KEY: misc_feature
<222> LOCATION: (22)..(22)
<223> OTHER INFORMATION: Xaa is preferably norleucine (NLE).

<400> SEQUENCE: 182

Lys Ile Arg Ser Ile Pro Thr Leu Glu Ala Gly Pro Gly Val Arg Thr
1               5                   10                  15

Leu Gln Gln Leu Leu Xaa Gly Thr Ser Thr Ile Val Ser Asp
            20                  25                  30
```

COMPOUNDS AND METHODS OF EARLY DIAGNOSIS OF CERVICAL CANCER AND GENITAL CONDYLOMA WITH HPV, CHSP60 TUMOR SUPPRESSOR H-RAS, K-RAS AND PTEN DERIVED PEPTIDES MODIFIED

BACKGROUND OF THE INVENTION

1. Field of Invention

The present invention relates to the field of the specific peptides reactive with antibodies formed against oncoproteins of the human papillomavirus (HPV). More particularly, the invention relates to peptides isolated, purified or derived from the sequences of the early coding regions of the E2, E4, E6, and E7 oncoproteins and late coding regions (L1 capsid proteins) of HPV; Harvey Ras (H-Ras), Kirsten Ras (K-Ras), and phosphatase and tensin homologue (PTEN) tumor suppressor proteins; and Chlamydia trachomatis heat shock protein 60 (CHSP60 groEL1), and the method for use for the detection and/or diagnosis of cervical epithelia cell abnormalities, precancerous clinical conditions and cervical carcinomas associated with HPV, tumor suppressor H-Ras, K-Ras, and PTEN, and CHSP60 groEL1, mutated or deleted peptides, via an immunoassay.

2. Background of the Invention

Cervical cancer is second only to breast cancer as the most frequent female malignancy and cause of death worldwide. International Agency for Research on Cancer (IARC) has estimated that in the year 2000 there was approximately 500,000 cases of cervical cancer worldwide. In the United States there are about 130,000 new cases of invasive cervical cancer each year and >4,000 deaths. Almost 80% of new cases occur among women in developing countries, with 80-85% of them appearing at late, incurable stages making incidence equivalent to mortality. Comparable worldwide figures are approximately 10 million cases of high grade dysplasia, 30 million cases of low grade dysplasia, and 300 million cases of cervical infection without cytologic abnormalities. This disease is due to infections by certain human papillomaviruses (HPV), as are many head and neck cancers as well as penile, urethral, anal and possibly some bladder cancers. On the basis of the strength of their association with cervical cancer, genital HPVs are placed into different risk categories as follows, high risk: HPV-16, 18, 31, 45 (each found in at least 5% of invasive cancers); intermediate risk: HPV-33, 35, 39, 51, 52, 56, 58, 59, 68 (each found in between 1% and 5% of invasive cancer); low risk: HPV-6, 11 and many others (rarely found in invasive cancer, but associated with genital condyloma). Another consequence is laryngeal papillomatosis in babies born to HPV-infected women, a pathology that kills 25,000 children per year. Such dire consequences of unmonitored HPV infections are a priority issue of major medical entities with a worldwide perspective like the World Health Organization, the Program for Applied Technology in Health, and the Johns Hopkins Program for International Education in Reproductive Health (JHPIEGO).

Cervical cancer is relatively common in the People's Republic of China, but little research has been published in the West about the relationship of these cancers to HPV infection in Chinese women. Cancers overwhelmingly stem from HPV 16 and 18, but may also be associated with HPV 31, 33, 35, 45, 51, 52, 56 and 58. One study of women from the Sichuan province in China demonstrated a significantly altered risk of cervical cancer associated with HPV 16 or HPV 33 infection at 95% confidence interval. Another study found evidence of HPV infection in 57% of women with invasive cervical cancer who live in Shanxi province, where the incidence of cervical cancer is extremely high at 1,026 per 100,000. A hospital-based study of women from Shanghai, P.R.C. revealed the prevalence of HPV infection and types of HPVs found in cervical cancer patients. This study provides new information about the occurrence of infection with HPV type 52, 58, two HPV types that are relatively uncommon in cervical cancer patients in the Americas, Europe, Africa and South Asia.

Human Papillomavirus (HPV) infection has been strongly associated with development of cervical cancer neoplasia. The virus is detected in almost 100% of women with invasive cervical cancer. Also the cancer itself may increase susceptibility to HPV infection. Routing cervical cancer screening in asymptomatic women has proven successful. The presence of HPV in cytologically normal Papanicolaou (Pap) smears is associated with a significantly increased risk of developing invasive cervical cancer. In particular, infection with high risk or multiple HPV genotypes result in a strongly increased risk of developing cervical cancer.

Although HPV infections are extremely prevalent in young populations, most HPV infections spontaneously clear. Only a small minority of individuals who are exposed to HPV have cervical cancer neoplasia. Thus, microbe-or host-specific cofactors *Chlamydia trachomatis* (*C trachomatis*) must be involved in the pathogenesis. *Chlamydia trachomatis* infection is an independent risk factor for the development of invasive cervical sequamous cell carcinoma (SCC). Chlamydial trachomatis infection is one of the most common sexually transmitted diseases (STDs) in the United States, with between 3 and 4 million new infections each year. Females with a chlamydial infection may have vaginal redness and discomfort accompanied by a vaginal discharge. Males may have a discharge from the urethra (the opening where urine comes out) and burning upon urination. Depending on the extent of the infection, there may occasionally be a low-grade fever. People with chlamydial infections often have no symptoms at all. Although an infected person may have no symptoms, he can still spread the infection to other sexual partners. *Chlamydia trachomatis* causes infections that can affect the eyes, lungs, or urogenital (urinary-genital) area, depending on the age of the person infected and how the infection is transmitted. *Chlamydia trachomatis* infections may spread to the upper reproductive tract, including the uterus, fallopian tubes, and ovaries and may cause pelvic inflammatory disease. Scarring of the fallopian tubes after chlamydial infection may cause permanent damage to the reproductive system, resulting in infertility. Chlamydial infections also increase the risk that bacteria will cause secondary infections in the pelvic organs, genitals, or rectum. Most females with chlamydial infections will be asymptomatic (they will not have any symptoms).

In industrialized countries *Chlamydia trachomatis* infections are more common than gonorrhea, another STD, but many people contract both infections simultaneously. Doctors estimate that among patients with gonorrhea, approximately 25% of men and up to 50% of women also have chlamydial infections. Experts believe that 5% to 25% of all pregnant women in the United States currently have chlamydial infections, and 50% of these mothers who deliver vaginally will infect their infants with *Chlamydia* at birth. Almost half of the infected children will develop a chlamydial conjunctivitis, and close to 20% will develop chlamydial pneumonia.

Heat shock proteins (HSP60) are recognized as immunodominant clamydial antigens, and several immunoepidemiologic studies have found an association with immune responses to *Chlamydia trachomatis*. Antibody to Chlamydial Heat shock proteins (HSP60) are associated with cervical squamous cell carcinoma. Antibodies to Heat shock proteins (CHSP60) appear to reflect persistent Chlamydia infection. (Jorma Paavonen., et al: Am J Obst; Gynecol 2003; 189; 1287-92; Tarja Anttila., et al: JAMA, 285(1): (47-51), 2001.

Mutational activation of K-Ras gene is implicated in the development of premalignant cervical lesions and HPV infection may be an important step in the development of premalignant cervical lesion. (Prokopakis P. Sourvinos G., et al: Oncol Rep, 9(1): 129-33, 2002.) K-Ras gene mutations were detected in 15% of cases while HPV genome was found in 36% of HPV type related cases and HPV 18 at a higher rate than HPV 16, 71% and 29% respectively. High-risk HPV infections coexist with K-Ras gene alterations in a subset of moderately differentiated carcinomas of the cervix uteri. (Stenzel A., et al: Pathol Res Pract, 9: 597-603, 2001.)

Harvey (H-Ras), Kirsten (K-Ras), and Neuroblastoma (N-Ras) genes have been localized to chromosomes 11, 12 and 1 respectively, in humans. All the ras oncogenes (H, K and N-Ras) encode for a 21-KDa (P21) protein, 189 amino acids long. Ras mutations in cervical carcinomas are low and preferentially occur at codon 12 of the K-ras gene. The point mutations at codon 12 of the K-Ras gene in premalignant and malignant cervical lesions range from 17% to 24%. This data suggests that the mutational activation of the K-Ras gene may be involved in the initial stages of cervical carcinogenesis. Although the presence of HPV is detected in over 90% of cervical carcinomas, it is insufficient to conclude that carcinogenesis has occurred. In vitro studies have demonstrated that an activated H-Ras gene can induce tumorrigenetic conversion of HPV-immortalized cervical kerationlcytes, indicating a cooperative effect between the ras and E6/E7 genes in cellular transformation. (Ioannis N. Mammas., et al: Gynecologic Oncology 92: 941-948, 2004.)

Studies have demonstrated an early immune recognition of E4 protein and mutated ras gene. Patients with condyloma and cervical intraepithelial neoplasia (CIN) also showed a higher prevalence of Ras antibodies (~40%) than cervical cancer patients (10%). The high prevalence of antibodies against Ras and E4 proteins in premalignant lesions opens the possibility of using both antibodies as early markers for potential cervical cancer patients. The levels of anti-Ras antibodies were relatively high in sera from patients with condyloma and CIN lesions. The presence of anti-Ras antibodies in early lesions of the cervix could be used as an early marker in cervical cancer patients.

Normal human cellular H-Ras, K-Ras and N-Ras genes have the potential for activation to oncogenes by mutations occurring in codons 12, 13 and 61; such mutated, activated and transforming K-Ras genes have been identified and isolated from human tumors and cultured tumor cells. Although the expression patterns of K-Ras proto-oncogene proteins in normal human tissues are known, similar information for activated K-Ras oncogene encoded p21's and its relevance to human disease diagnosis and prognosis remains to be determined. (A. Pedroza-Saavedra., et al: Arch Virol 145: 603-623, 2000.)

Phosphatase and tensin homologue (PTEN) tumor suppressor protein has been demonstrated in the role of epigenetic and genetic changes of PTEN in the development of sequamous cell carcinoma (SCC) of the uterine cervix and their value as prognostic factor. Tumor suppressor gene, PTEN (also known as MMAC-1 and PTEN-1) located at chromosome 10q23.3 has an important role in controlling cell growth, inducing cell cycle arrest, promoting apoptosis, down regulating adhesion and suppressing cell migration. Deletion and/or mutation of the PTEN gene has been found in a variety of human cancers, including brain, prostate, breast, thyroid, lung and endometrium. More specifically, deletion and/or mutation of the PTEN gene has been found in 30-50% of endometrial cancer cases, 40% in cases where hyper-methylation of the promoter region of PTEN occurs, and 36% in a CIN-H and cervical carcinoma immunostaining study. The detection of PTEN and related specific PTEN antibodies is an early event in the development of cervical cancer carcinoma and is effective in silencing PTEN expression. Loss of PTEN function subsequent to HPV infection therefore might contribute to progression into carcinoma after deletion and/or mutation and methylation of the PTEN gene. (Tak-Hong Cheung., et al: Gynecologic Oncology, 93: 621-627, 2004; Takeo Minaguchi., et al: Cancer Letters 210: 57-62, 2004.)

The key of the molecular basis of immune responses is that immunogens are degraded, through a complex series of cellular processing events, into small peptide fragments. There are two pathways, endogenous and exogenous for degradation of proteins that share several similarities, but are also associated with fundamental differences. Small peptides of HPV oncoprotein fragments, tumor suppressor Ras and CHSP60 protein are bound by specific cellular receptors called Major Histocompatibility Complex (MHC) molecules. In the case of human cells MHC molecules are known as Human Leukocyte Antigen (HLA) molecules. The major biological function of the HLA molecules is to bind peptides. HLA class I molecules mostly bind peptides derived from the endogenous processing pathway and thus from proteins derived from inside cells. HLA class I molecules are most important for antiviral and anticancer immunity. Peptides derived from the extracellular milieu tend to bind to HLA class II molecules. These molecules are important for helper T-cell responses, which regulate antibody and cytotoxic responses.

T cells are key players in regulating a specific immune response. Activation of cytotoxic T-cells requires recognition of specific peptides bound to Major Histocompatibility Complex (MHC) class I molecules or HLA class I molecules in the case of human cells. The critical role of the human leukocyte antigen (HLA) system in presenting peptides to antigen-specific T cell receptors is that T cell responses that clear viral infections can be induced when the major histocompatibility gene products are complexed with peptides derived from HPV viral antigens and present on the surface of antigen-presenting cells. MHC-peptide complexes are potential tools for diagnosis and treatment of pathogens and cancer, as well as for the development of peptide vaccines. Only one in 100 to 200 potential binders actually binds to a certain MHC molecule, as the activation of cytotoxic T-cells requires recognition of specific peptides bound to MHC class I molecules. The complex between peptides and HLA receptors is transported to the cell surface where it can be recognized by T cells expressing a specific T-cell receptor (TCR) for that particular peptide-HLA combination. The peptides bound by HLA molecules and recognized by these specific T cells are called epitopes. A good prediction method for MHC class I binding peptides can reduce the number of candidate binders that need to be synthesized and tested. (Arkadium Chil, et al: Acta Obstet Scand, 82: 1146-1152), 2003.

Major Histocompatibility Complex (MHC) Class I, II and an oligopeptide (>90%) are 8-11 amino acids in length and encoded by a viral gene, tumor suppressor and CHSP60.

Peptides are pre-dominantly generated from the hyproducts of proteasomal degration. The molecules are cell surface glycoproteins, which take an active part in host immune reactions. Here, the MHC class I molecule is folded through the concentrated chaperone (tapasin). The oncogenetic HPV E2, E4, E5, E6, E7 oncoproteins, tumor suppressor Ras proteins and CHSP60 are coded by three classes of genes. Class I and Class II gene products are directly associated with immune reactions with Class II gene products playing an indirect role.

Class I genes encode the principle subunits of MHC I glycoprotein called H2-K, H2-d, H2-l in mice and HLA-A, B, C in humans. Proteins encoded by these genes are present virtually on all nucleated cells. Class I molecules interact with the amino (N-) and carboxyl (C-) terminals of the bound peptide, leaving a bulge in the middle. These N- & C-terminal interactions together with closed peptide binding groove restrict the length of interacting peptide to 8-10 amino acids. However peptide-binding groove of Class II molecules is open at both ends and the interactions of peptide are more diffuse thereby a more variable length is allowed (generally 10-28 amino acids). The involvement of MHC class-II with HPV early proteins is in response to almost all antigens. (A. Sette, et al: Tissue Antigens, 59: 443-451, 2002; Margaret M. Madeleine, et al: JID, 186(1) 1565-1574, 2002.)

For the Chinese population based on HLA, microsatellites and other gene loci have divided the Chinese population into two groups, the Southern and the Northern. Dai and Buyi were two representative Southern Chinese population with Jing also belonging to the Southern group. The most frequent DPB1 allele was DPB1 *0501, DPB1 *1301, DPB1 *0401, and DPB1 *020102. Frequent DRB1 alleles are DRB1 *150201, 030101, DRB1 *090102. The most predominant DQB1 alleles was DQB1 *030101/0309, DQB1 *050201, and DQB1 *0201/0202. The high affinity binding prediction of peptides by HMCPred program runs as a GCI server and covers a range of different human HMC allele peptide specificity models, which include: class I (HLA-A *0101, HLA-A *0102, HLA-A *0202, HLA-A *0203, HLA-A *0206, HLA-A *0301, HLA-A *1101, HLA-A *3301, HLA-A 6801, HLA-A 6802, HLA-A 3501) and class II (HLA-A-DRB1 *0101, HLA-A-DRB1 *0401 and HLA-A-DRB1 *0701) alleles. All their alleles exist at a high frequency within human populations and have significant literature binding dates.

The first reported association between HLA class II gene and cervical cancer were DQw3, a serologic designation that has subsequently been subdivided into 3 other serologic designations: DQ7, DQ8, and DQ9. The specificities include DQB1 0301, *0303 and 0304 for DQ7, DQB1 *0302 and 0305, DQB1 0302 and 0305 for DQ8 and DQB1 0303 for DQ9. Other allele groups that have been reported with increased risk include DRB1 *11, DRB1 *15, DQB1 *06, and related haplotypes DRB1 *0401, DRB1 *0301, DRB1 * 1101, DRB1 *1501, and DQB1 *0602. In contrast to an increased risk of invasive disease associated with DRB1 *1501-DQB1 *0602 according to Hispanic American and British studies, Hildesheim et al. reported a decreased risk of HPV-16 containing high grade aquamous intraepithelial cervical lesions associated with DRB1 *1501-DQB1 *0602 based on a U.S. study of white women in Portland, Oreg. area. (Jin-Hia Lin, et al: Human Immunology 2003: 64: 830-834; Pingping Guan, et al: Nucleic Acid Research 2003 Vol. 31 No.13 3621-3624; Harpresst Singh, et al: Bioinformatics 2003: Vo. 19 No.8 1009-1014).

While the prior art provides diagnosis and early prediction of cancer or cellular abnormalities based on Papanicolaou (Pap) smear screening, these tests do not provide HPV type, sensitive, rapid, simple, and economical detection of genital condyloma, squamous cell carcinoma (SCC), squamous interaepithelial lesion (SIL), low-grade squamous interaepithelial lesion (LSIL), high-grade squamous interaepithelial lesion (HSIL), cervical intraepithelial neoplasia (CIN) and invasive cervical cancer.

There is a need in the art, therefore, for an early diagnosis and better treatment of cervical cancer utilizing diagnosis kits and specific HPV peptide vaccines. The prior approaches are primarily focused on detection of immunoassays of HPV, tumor suppressors and heat shock proteins of immunodominant clamydial antigens.

Accordingly, it is a principal object of the present invention to provide a method of detecting specific antibodies against the E2, E4, E6, E7 oncoproteins, tumor suppressor proteins and *Chlamydia trachomatis* heat shock protein antigens, utilizing novel protein and peptide sequences for the early detection of genital condyloma, squamous cell carcinoma (SCC), squamous interaepithelial lesion (SIL), low-grade squamous interaepithelial lesion (LSIL), high-grade squamous interaepithelial lesion (HSIL), cervical intraepithelial neoplasia (CIN) and invasive cervical cancer.

A primary object of the present invention is to provide novel antibody reactive protein sequences or peptides isolated, purified or derived from the HPV proteins, tumor suppressor proteins (H-Ras, K-Ras and PTEN), and *Chlamydia trachomatis* heat shock protein 60 (CHSP60 groEL1).

A further object of the present invention is to provide a simple, rapid, less expensive, specific and more sensitive test for detecting or diagnosing not only HPV infections, but also most, if not all, HPV associated neoplasms.

It is a further object of the present invention to provide these peptides in a chemically pure form.

It is still another object of the present invention to provide novel antibody reactive protein sequences or peptides isolated, purified or derived from HPV genotypes 6, 11, 16, 18 31, 33, 45, 52 and 58.

In addition, it is an object of the present invention to provide novel antibody reactive protein sequences or peptides isolated from early and late coding regions of HPV linked to other protein sequences or peptides isolated from HPV E2, E4, H6, E7 oncoproteins and L1 capsid proteins, H-Ras, K-Ras, PTEN, or CHSP60 groEL1, by adding neutral, genetically coded amino acid residues as a media linker between the peptides and epitopes.

It is a further object of the present invention to provide a method for detecting or diagnosing cancer or cellular abnormalities comprising the steps of: reacting a sample of body fluid or tissue likely to contain IgG and IgA specific antibodies to one or more protein sequences or peptides isolated from the E2, E4, E6 and E7 early coding regions and late coding regions of L1 capsid proteins of HPV, and characterized by a linkage to another protein sequence or peptide isolated from the E2, E4, E6, and E7 early coding regions of HPV; forming an antibody-peptide complex comprising at least one of the isolated protein sequences or peptides and the sample antibodies; and detecting the antibody-peptide complex.

It is a further object of the present invention to provide a method for detecting or diagnosing cancer or cellular abnormalities through detection or diagnosis of HPV associated cell abnormalities.

It is also an object of the present invention to provide a method for detecting or diagnosing cancer or cellular abnormalities through detection or diagnosis of HPV associated precancerous or premalignant conditions.

Further objects of the invention will become apparent from the following description.

SUMMARY OF THE INVENTION

The embodiments of the present invention solve the problems and address the drawbacks of the approaches in the above description. An embodiment of the present invention includes novel peptides, the sequences of which were isolated from the early, late coding regions of the E2, E4, E6, and E7 oncoproteins and L1 capsid proteins of HPV 6, 11, 16, 18 31, 33, 45, 52 and 58. The peptides are used for a sensitive and specific diagnostic immunoassay.

The high binding peptides invented and derived from HPV, CHSP60 and tumor suppressor K-Ras, H-Ras and PTEN epitopes modified, provide a sensitive, straight forward and low-cost test for detecting antibodies to cancer-causing HPV, CHSP60, Ras and PTEN associated diseases. Such a test confirms HPV infection in a fashion that also identifies cervical and other HPV-related cancers or the likelihood of their presence.

An embodiment of the present invention includes isolated peptides, ranging in size, from about 10 amino acid residues to about 43 amino acid residues. The isolated peptides may be readily synthesized by chemical means and may be obtained at purities exceeding 95%. Pure peptides of the present invention may be used for diagnostic immunoassays of high specificity. Immunoassays employing the peptides isolated or derived from the E2, E4, E6, and E7 oncoproteins of HPV 6, 11, 16, 18 31, 33, 45, 52 and 58 and L1 capsid proteins may serve as reliable indicators that HPV associated malignancy or premalignant cell transformation has taken place.

A further embodiment of the present invention is a novel antibody reactive protein sequences or peptides isolated, purified or derived from HPV and L1 capsid proteins linked to other protein sequences or peptides isolated from HPV, H-Ras, K-Ras, PTEN, or CHSP60 groEL1, by adding neutral, genetically coded amino acid residues as a media linker between the peptides and epitopes.

A further embodiment of the present invention is an immunoassay method for detecting or diagnosing cancer or cellular abnormalities comprising the steps of: 1) taking a sample of body fluid or tissue likely to contain antibodies; 2) reacting the sample with one or more of the peptides of the present invention; and 3) assaying the reacted sample for the presence of an antibody-peptide reaction.

An additional embodiment of the present invention is a strip test. The strip test will show a colored line when disease is present. Some unique and highly desirable attributes of the strip test are its inexpensive nature and that no special laboratory facilities or highly trained clinicians are required for its use and test results are immediate. Further, a drop of blood or other body fluids, like mucous and possibly urine, may be used as samples to yield rapid visualization of HPV infection and consequent disease.

These and other embodiments of the present invention are further made apparent, in the remainder of the present document, to those of ordinary skill in the art.

BRIEF DESCRIPTION OF THE DRAWINGS

In order to more fully describe embodiments of the present invention, reference is made to the accompanying drawings. These drawings are not to be considered limitations in the scope of the invention, but are merely illustrative.

TABLE 1 refers to Absorbance values and diagnosis of dysplasia from subjects tested for cervical disease via Enzyme-Linked Immunosorbent Assay (ELISA), using peptides of the present invention.

TABLE 2 refers to Amino acid names, abbreviations and symbols.

DETAILED DESCRIPTION OF SPECIFIC EMBODIMENTS

The description above and below of the present document focus on one or more preferred embodiments of the present invention and also describe some exemplary optional features and/or alternative embodiments. The following more detailed description of the embodiments of the present invention is for the purpose of illustration and not limitation. It will be readily understood by those of ordinary skill in the art that the isolated protein sequences and methodologies of the present invention, as generally described, could be arranged and designed in a wide variety of different configurations without departing from the essential characteristics of the invention, as described. Such variations, modifications, and alternatives are also within the scope of the present invention. Section titles are terse and are for convenience only.

An embodiment of the present invention may include a predicted amino acid sequence of HPV oncoproteins, tumor suppressor proteins (K-Ras, H-Ras, and PTEN), and CHSP60 proteins, having epitopes that predict predominantly hydrophilic and hydrophobic portions of polypeptides to help identify solvent-exposed regions on the surface of the protein. A peptide's solubility is strongly influenced by the peptide's composition. Peptides can have a high content solubility in aqueous solution or be completely insoluble. The peptides with a high content of hydrophobic residues, such as Leu, Val, Ile, Met, Phe, and Trp, (Refer to TABLE 2) will either have limited solubility in aqueous solution or be completely insoluble. The peptides synthesized must be kept at a hydrophobic amino acid content below 50% and to make sure that there is at least one charged residue for every five amino acids.

In order to increase the polarity of the peptide, it may be useful to lengthen the sequence, select some polarity residues and add these polar amino acids into peptides to increase peptide polarity. Alternatively, the sequence may be shortened to eliminate hydrophobic residues and increase peptide polarity. The hydrophilic amino acids such as Arg, His and Lys have side chains with amino group with side chains fully protonated at pH 7.4. Addition of one negatively charged amino acid residue such as Asp, Glu or Tyr to the carboxyl (C-) terminus of the peptide, if the C- terminus is not amidated, may improve peptide solubility. Further addition of a polar residue such as Lys, Arg or His to the amino (N-) terminus, if the N- terminus is not a positively charged residue, may also improve peptide solubility thus increasing peptide affinity and binding capacity onto the microplate.

Peptides containing Trp, Met, and Cys are difficult to obtain in high purity, partly because these residues are susceptible to oxidation and alkylation. Met and Cys are the only sulfur-containing amino acids having a hydrophobic amino acid. Cys is one of two sulfur-containing amino acids and differs from Ser in a single atom. The sulfur of the thiol replaces the oxygen of the alcohol. The sulfur of Met, as with that of Cys, is prone to oxidation, yielding methionine sulfoxide. L-Isomer Norleucine (Nle) is an non-naturally occurring amino acid, and is a linear sidechain isomer of leucine that has hydrophobic residues. Nle is structurally similar to Met, but does not contain sulfur. Nle can be used as a replacement for Met. The replacement of Met with its non-naturally occurring amino acid such as Nle may decrease the oxidation of peptides containing Met. Ser may be used as a less reactive replacement for Cys. A change in the number of Cys, Met and Trp residues contained in individual peptides would not affect the biology and immunity of the peptides and epitopes.

A further embodiment of the present invention may include a modified amino acid sequence of HPV oncoprotein, tumor suppressor protein (K-Ras, H-Ras, and PTEN), or CHSP60 protein, linked by a neutral genetically coded amino acid sequence or universal spacer sequence to another modified amino acid sequence of HPV oncoprotein, tumor suppressor protein (K-Ras, H-Ras, and PTEN), or CHSP60 protein, comprising two specific and high binding epitope sequences which can be reacted with residues from both major histocompatibility complex (MHC) of high risk, low risk HPV early protein and Ras tumor suppressor proteins. Cell-mediated immune (CMI) responses to HPV E2, E4, E6 and E7 peptides include two specific and high binding epitope sequences. The modified peptide sequences may retain strong antigen epitope character of two different oncogenetic HPV types, which consist of more than 50% hydrophilic amino acids in each peptide. The modified peptide sequences may be recognized by specific antibodies of HPV from patient serum during the assay.

The neutral genetically coded amino acid sequence may function as a media linker for the modified peptides. Glycine (G) is a neutral, genetically coded amino acid. It is the only protein-forming amino acid without a center of chirality. L-Proline (P) is a neutral, genetically coded amino acid. The universal spacer sequence may comprise of a GPGPG, GPG or a GGPGG sequence. Multiple synthesized peptides may be linked by the GPGPG, GPG or GGPGG spacer sequence. The universal spacer sequence does not interfere with both sides of the epitope sequences nor do they affect the amino acid sequences function. The GPGPG and the GGPGG spacer sequence may eliminate the response against the junctional epitope, significantly decreasing the HLA-DR binding capacity of the junctional region.

Antibodies to the E2, E4, E6, and E7oncoproteins may be found in those individuals infected with HPV associated cell abnormalities. Antibodies complexed with HPV specific high risk oncogenetic peptides and with genital condyloma specific low risk non-oncogenetic peptides may be detected using ELISA and fast test strips technology. Such detection could be a particularly useful tool of diagnosing HPV infection associated with cervical invasive carcinoma. This technology is dramatically superior to extant tests because of its sensitivity and rapidity in consort with uncomplicated and economical use. Too few cells or improperly harvested ones are partly why PAP smears fail to properly detect disease. Such circumstances are highly improbable with the strip test, since it uses so little material to get legitimate results.

One hundred seventy-nine specific protein sequences or peptides ranging from 10 to 44 amino acid residues in length, may be isolated, purified or derived from the E2, E4, E6, and E7 oncoproteins of HPV 6, 11, 16, 18 31, 33, 45, 52 and 58, as defined herein below.

Sequence Identification number 1 (SEQ. ID. No. 1) was derived from the E7 region of HPV 17. Using the standard three letter acronym, SEQ. ID. No 1, is comprised of 26 residues made up of amino acids 28-39 and 11-26 of the HPV 16 E7 oncoprotein linked by a GPG spacer sequence, as follows, with the sequence beginning at the amino terminal residue and ending at the carboxyl terminal residue: (SEQ. ID. No. 1) Lys Leu Asn Asp Ser Ser Glu Glu Glu Asp Glu Ile Asp Gly Pro Gly Tyr Nle Leu Asp Leu Gln Pro Glu Thr Asp.

SEQ. ID. No. 2 was derived from the E7 region of HPV 16 and is comprised of 16 residues made up of amino acids 81-94 of the HPV16 E7 oncoprotein having Met replaced with Nle and Cys replaced with Ser, as follows, with the sequence beginning at the amino terminal residue end: (SEQ. ID. No. 2) Lys Leu Leu Nle Gly Thr Leu Gly Ile Val Ser Pro Ile Ser Ser Glu.

SEQ. ID. No. 3 was derived from the E7 regions of HPV 16 and 18, and is comprised of 31 residues made up of amino acids 75-83 of the HPV16 E7 oncoprotein linked by a GPG spacer sequence to amino acids 33-48 of the HPV 18 E7 oncoprotein, as follows, with the sequence beginning at the amino terminal residue end: (SEQ. ID. No. 3) Arg Asp Ile Arg Thr Leu Glu Asp Leu Leu Nle Gly Pro Gly Asp Ser Glu Glu Glu Asn Asp Glu Ile Gly Asp Val Asn His Gln His Glu.

SEQ. ID. No. 4 was derived from the E7 region of HPV 16 and 18, and is comprised of 32 residues made up of amino acids 28-39 of the HPV16 E7 oncoprotein linked by a GPG spacer sequence to amino acids 33-48 of the HPV 18 E7 oncoprotein, as follows, with the sequence beginning at the amino terminal residue end: (SEQ. ID. No. 4) Lys Leu Asn Asp Ser Ser Glu Glu Glu Asp Glu Ile Asp Gly Pro Gly Asp Ser Glu Glu Glu Asn Asp Glu Ile Gly Val Asn His Gln His Glu.

SEQ. ID. No. 5 was derived from the E6 and E7 regions of HPV 16, and is comprised of 36 residues made up of amino acids 28-39 of the HPV16 E7 oncoprotein linked by a GPG spacer sequence to amino acids 120-138 of the HPV 16 E6 oncoprotein, as follows, with the sequence beginning at the amino terminal residue end: (SEQ. ID. No. 5) Lys Leu Asn Asp Ser Ser Glu Glu Glu Asp Glu Ile Asp Gly Pro Gly Glu Glu Lys Gln Arg His Leu Asp Lys Lys Gln Arg Phe His Asn Ile Arg Gly Arg Asp.

SEQ. ID. No. 6 was derived from the E6 and E7 regions of HPV 18, and is comprised of 37 residues made up of amino acids 115-134 of the HPV18 E6 oncoprotein linked by a GPG spacer sequence to amino acids 33-48 of the HPV 18 E7 oncoprotein, as follows, with the sequence beginning at the amino terminal residue end: (SEQ. ID. No. 6) Lys Ala Glu Lys Leu Arg His Leu Asn Glu Lys Arg Arg Phe His Asn Ile Ala Gly Pro Gly Asp Ser Glu Glu Asn Asp Glu Ile Gly Asp Val Asn His Gln His Glu.

SEQ. ID. No. 7 was derived from the E6 region of HPV 16 and is comprised of 28 residues made up of amino acids 1-26 of the HPV16 E6 oncoprotein, having Met replaced with Nle and Cys replaced with Ser, as follows, with the sequence beginning at the amino terminal residue end: (SEQ. ID. No. 7) Lys Nle His Gln Lys Arg Thr Ala Nle Phe Gln Asp Pro Gln Glu Arg Pro Arg Lys Leu Pro Gln Leu Ser Thr Glu Leu Glu.

SEQ. ID. No. 8 was derived from the E7 region of HPV 18 and is comprised of 29 residues made up of amino acids 32-60 of the HPV18 E7 oncoprotein, as follows, with the sequence beginning at the amino terminal residue end: (SEQ. ID. No. 8) Lys Ser Asp Ser Glu Glu Asn Asp Glu Ile Gly Asp Val Asn His Gln His Leu Pro Ala Arg Arg Ala Glu Pro Gln Arg His Glu.

SEQ. ID. No. 9 was derived from the E2 region of HPV 18 and the L1 region of HPV 16/18 and is comprised of 34 residues made up of amino acids 328-345 of the HPV 18 E2 oncoprotein linked by a GPG spacer sequence to amino acids 418-427 of the HPV 16/18 L1 oncoprotein, and having Met replaced with Nle, as follows, with the sequence beginning at the amino terminal residue end: (SEQ. ID. No. 9) Arg Glu Lys Thr Gly Ile Leu Thr Val Thr Tyr His Ser Glu Thr Gln Arg Thr Lys Gly Pro Gly Tyr Ile His Ser Nle Asn Ser Thr Ile Leu Glu Asp.

SEQ. ID. No. 10 was derived from the E7 region of HPV 16 and is comprised of 33 residues made up of amino acids 43-77 of the HPV 16 E7 oncoprotein, having Cys replaced with Ser, as follows, with the sequence beginning at the amino terminal residue end: (SEQ. ID. No. 10) Lys Gly Gln Ala Glu Pro Asp Arg Ala His Tyr Asn Ile Val Thr Phe Ser Ser Lys Ser Asp Ser Thr Leu Ser Ser Thr His Val Asp Ile Arg Glu.

SEQ. ID. No. 11 was derived from the E7 region of HPV 16 and L1 region of HPV 16/18, and is comprised of 30 residues made up of amino acids 81-94 of the HPV 16 E7 oncoprotein linked by a GPG spacer sequence to amino acids 452-461 of the HPV 16 L1 oncoprotein and 418-427 of the HPV18 L1 oncoprotein, and having Met replaced with Nle and Cys replaced with Ser, as follows, with the sequence beginning at the amino terminal residue end: (SEQ. ID. No. 11) Lys Leu Leu Nle Gly Thr Leu Gly Ile Val Ser Pro Ile Ser Ser Gly Pro Gly Tyr Ile His Ser Nle Asn Ser Thr Ile Leu Glu Asp.

SEQ. ID. No. 12 was derived from the E7 regions of HPV 16 and HPV 18, and is comprised of 39 residues made up of amino acids 49-57 of the HPV 16 E7 oncoprotein linked by a GPG spacer sequence to amino acids 32-60 of the HPV 18 E7 oncoprotein, and having Cys replaced with Ser, as follows, with the sequence beginning at the amino terminal residue end: (SEQ. ID. No. 12) Arg Ala His Tyr Asn Ile Val Thr Phe Ser Gly Pro Gly Ser Glu Glu Glu Asn Asp Glu Ile Asp Gly Val Asn His Gln His Leu Pro Ala Arg Arg Ala Glu Pro Gln Arg Glu, SEQ. ID. No. 13 was derived from the E7 region of HPV 16 and is comprised of 35 residues made up of amino acids 3-35 of the HPV 16 E7 oncoprotein, having Met replaced with Nle, as follows, with the sequence beginning at the amino terminal residue end: (SEQ. ID. No. 13) Lys Gly Asp Thr Pro Thr Leu His Glu Tyr Nle Leu Asp Leu Gln Pro Glu Thr Thr Asp Leu Tyr Ser Tyr Glu Gln Leu Asn Asp Ser Ser Glu Glu Glu Asp.

SEQ. ID. No. 14 was derived from the L1 region of HPV 16/18 and E7 region of HPV 58, and is comprised of 31 residues made up of amino acids 452-461 of the HPV 16 L1 capsid proteins and amino acids 418-427of the HPV 18 L1 capsid proteins linked by a GPG spacer sequence to amino acids 77-92 of HPV58 E7 oncoprotein, and having Met replaced with Nle, as follows, with the sequence beginning at the amino terminal residue end: (SEQ. ID. No. 14) Asp Tyr Ile His Ser Nle Asn Ser Thr Ile Leu Gly Pro Gly Val Arg Thr Leu Gln Gln Leu Leu Nle Gly Thr Ser Thr Ile Val Ser Asp.

SEQ. ID. No. 15 was derived from the E7 regions of HPV 58 and HPV 16, and is comprised of 28 residues made up of amino acids 37-45 of the HPV58 E7 oncoprotein linked by a GPG spacer sequence to amino acids 81-94 of the HPV 16 E7 oncoprotein, and having Met replaced with Nle and Cys replaced with Ser, as follows, with the sequence beginning at the amino terminal residue end: (SEQ. ID. No. 15) Lys Ile Gly Leu Asp Gly Pro Asp Gly Gln Gly Pro Gly Leu Leu Nle Gly Thr Leu Gly Ile Val Ser Pro Ile Ser Ser Asp.

SEQ. ID. No. 16 was derived from the E6 region of HPV 58 and E7 region of HPV 16, and is comprised of 44 residues made up of amino acids 36-60 of the HPV 58 E6 oncoprotein linked by a GPG spacer sequence to amino acids 81-94 of the HPV 16 E7 oncoprotein, and having Met replaced with Nle and Cys replaced with Ser as follows, with the sequence beginning at the amino terminal residue end: (SEQ. ID. No. 16) Lys Leu Gln Arg Ser Glu Val Tyr Asp Phe Val Phe Ala Asp Leu Arg Ile Val Tyr Arg Asp Gly Asn Pro Phe Ala Gly Pro Gly Leu Leu Nle Gly Thr Leu Gly Ile Val Ser Pro Ile Ser Ser Glu.

SEQ. ID. No. 17 was derived from the E6 regions of HPV 58 and HPV 16, and is comprised of 40 residues made up of amino acids 36-60 of the HPV 58 E6 oncoprotein linked by a GPG spacer sequence to amino acids 19-27 of the HPV 16 E6 oncoprotein, as follows, with the sequence beginning at the amino terminal residue end: (SEQ. ID. No. 17) Glu Leu Gln Arg Ser Glu Val Tyr Asp Phe Val Phe Ala Asp Leu Arg Ile Val Tyr Arg Asp Gly Asn Pro Phe Ala Gly Pro Gly Lys Leu Pro Gln Leu Ser Thr Glu Leu Gln Asp.

SEQ. ID. No. 18 was derived from the E7 region of HPV 16 and E6 region of HPV 58, and is comprised of 32 residues made up of amino acids 86-94 of the HPV 16 E7 oncoprotein linked by a GPG spacer sequence to amino acids 19-27 of the HPV 58 E6 oncoprotein, and having Cys replaced with Ser, as follows, with the sequence beginning at the amino terminal residue end: (SEQ. ID. No. 18) Arg Glu Leu Gly Ile Val Ser Pro Ile Ser Ser Gly Pro Gly Leu Arg Leu Leu Ser Lys Ile Ser Glu Tyr Arg His Tyr Asn Tyr Ser Leu Tyr.

SEQ. ID. No. 19 was derived from the E6 region of HPV 58 and E7 region of HPV 16, and is comprised of 36 residues made up of amino acids 19-27 of the HPV 58 E6 oncoprotein linked by a GPG spacer sequence to amino acids 81-94 of the HPV 16 E7 oncoprotein, and having Cys replaced with Ser, as follows, with the sequence beginning at the amino terminal residue end: (SEQ. ID. No. 19) Lys Leu Arg Leu Leu Ser Lys Ile Ser Glu Tyr Arg His Asn Tyr Ser Leu Tyr Gly Pro Gly Leu Leu Nle Gly Thr Leu Gly Ile Val Ser Pro Ile Ser Ser Glu.

SEQ. ID. No. 20 was derived from the E7 regions of HPV 16 and HPV 58/16, and is comprised of 34 residues made up of amino acids 28-39 of the HPV 16 E7 oncoprotein linked by a GPG spacer sequence to amino acids 67-84 of the HPV 58 E6 and amino acids 81-91 of the HPV16 E6 oncoproteins, as follows, with the sequence beginning at the amino terminal residue end: (SEQ. ID. No. 20) Lys Glu Leu Asn Asp Ser Ser Glu Glu Glu Asp Glu Ile Asp Gly Pro Gly Leu Arg Leu Leu Ser Lys Ile Ser Glu Tyr Arg His Asn Tyr Ser Leu Tyr.

SEQ. ID. No. 21 was derived from the E6 regions of HPV 16 and HPV 52, and is comprised of 32 residues made up of amino acids 17-26 of the HPV 52 E6 oncoprotein linked by a GPG spacer sequence to amino acids 42-53 of the HPV 58 E6 oncoprotein, and having Cys replaced with Ser, as follows, with the sequence beginning at the amino terminal residue end: (SEQ. ID. No. 21) Arg Lys Leu Pro Gln Leu Ser Thr Glu Leu Gly Pro Gly Val Tyr Lys Phe Leu Phe Thr Asp Leu Arg Ile Val Tyr Arg Asp Asn Asn Pro Tyr.

SEQ. ID. No. 22 was derived from the E6 regions of HPV 16 and HPV 52 and E7 region of HPV 58, and is comprised of 42 residues made up of amino acids 19-27 of the HPV 16 E6 oncoprotein linked by a GPG spacer sequence to amino acids 25-34 of the HPV 52 E6 oncoprotein, further linked by a GPG spacer sequence to amino acids 77-92 of the HPV58 E7 oncoprotein, and having Met replaced with Nle and Cys replaced with Ser, as follows, with the sequence beginning at the amino terminal residue end: (SEQ. ID. No. 22) Lys Leu Pro Gln Leu Ser Thr Glu Leu Gln Gly Pro Gly Ile Arg Leu Gln Ser Val Gln Ser Lys Gly Pro Gly Val Arg Thr Leu Gln Gln Leu Leu Nle Gly Thr Ser Thr Ile Val Ser Asp.

SEQ. ID. No. 23 was derived from the E7 regions of HPV 16 and HPV 58, and is comprised of 35 residues made up of amino acids 81-94 of the HPV 16 E7 oncoprotein linked by a GPG spacer sequence to amino acids 77-92 of the HPV 58 E7 oncoprotein, and having Met replaced with Nle and Cys replaced with Ser, as follows, with the sequence beginning at the amino terminal residue end: (SEQ. ID. No. 23) Lys Leu Leu Nle Gly Thr Leu Gly Ile Val Ser Prop Ile Ser Ser Gly Pro Gly Val Arg Thr Leu Gln Gln Leu Leu Nle Gly Thr Ser Thr Ile Val Ser Glu.

SEQ. ID. No. 24 was derived from the E6 regions of HPV 16 and HPV 52, and is comprised of 25 residues made up of amino acids 58-66 of the HPV 16 E6 oncoprotein linked by a GPG spacer sequence to amino acids 25-34 of the HPV 52 E6 oncoprotein, as follows, with the sequence beginning at the amino terminal residue end: (SEQ. ID. No. 24) Lys Ile Val Tyr Arg Asp Gly Asn Pro Tyr Gly Gly Pro Gly Gly Ile Arg Leu Gln Ser Val Gln Ser Lys Asp.

SEQ. ID. No. 25 was derived from the E6 region of HPV 52 and E7 region of HPV 58, and is comprised of 30 residues made up of amino acids 25-34 of the HPV 52 E6 oncoprotein linked by a GPG spacer sequence to amino acids 77-91 of the HPV 58 E7 oncoprotein, and having Met replaced with Nle, as follows, with the sequence beginning at the amino terminal residue end: (SEQ. ID. No. 25) Lys Ile Arg Leu Gln Ser Val Gln Ser Lys Gly Pro Gly Val Arg Thr Leu Gln Gln Leu Leu Nle Gly Thr Ser Thr Ile Val Ser Glu.

SEQ. ID. No. 26 was derived from the E6 region of HPV 16 and E7 region of HPV 52, and is comprised of 38 residues made up of amino acids 59-67 of the HPV 16 E6 oncoprotein linked by a GPG spacer sequence to amino acids 1-24 of the HPV 52 E7 oncoprotein, and having Met replaced with Nle, as follows, with the sequence beginning at the amino terminal residue end: (SEQ. ID. No. 26) Lys Asn Val Tyr Arg Asp Gly Asn Pro Tyr Ala Gly Pro Gly Nle Arg Gly Asp Lys Ala Thr Ile Lys Asp Tyr Ile Leu Asp Leu Gln Pro Glu Thr Thr Asp Leu His Glu.

SEQ. ID. No. 27 was derived from the E7 regions of HPV 52 and HPV 16, and is comprised of 36 residues made up of amino acids 1-19 of the HPV 52 E7 oncoprotein linked by a GPG spacer sequence to amino acids 28-39 of the HPV 16 E7 oncoprotein, as follows, with the sequence beginning at the amino terminal residue end: (SEQ. ID. No. 27) Lys Glu Nle Arg Gly Asp Lys Ala Thr Ile Lys Asp Tyr Ile Leu Asp Leu Gln Pro Glu Thr Thr Gly Pro Gly Leu Asn Asp Ser Ser Glu Glu Glu Asp Glu Ile Asp.

SEQ. ID. No. 28 was derived from the E7 regions of HPV 58 and HPV 52, and is comprised of 31 residues made up of amino acids 77-91 of the HPV 58 E7 oncoprotein linked by a GPG spacer sequence to amino acids 78-86 of the HPV 52 E7 oncoprotein, and having Met replaced with Nle and Cys replaced with Ser, as follows, with the sequence beginning at the amino terminal residue end: (SEQ. ID. No. 28) Lys Val Arg Thr Leu Gln Gln Leu Leu Nle Gly Thr Ser Thr Ile Val Ser Gly Pro Gly Leu Arg Thr Leu Gln Gln Nle Leu Leu Asn Glu.

SEQ. ID. No. 29 was derived from the E6 and E2 region of HPV 16 and is comprised of 23 residues made up of amino acids starting at 82-/93- of the HPV 16 E6/E2 oncoprotein having a GPG spacer sequence, and having and Cys replaced with Ser, as follows, with the sequence beginning at the amino terminal residue end: (SEQ. ID. No. 29) Lys Tyr Arg His Tyr Ser Tyr Ser Lue Tyr Gly Pro Gly Thr Lue Gln Asp Val Ser Lue Glu Val Asp.

SEQ. ID. No. 30 was derived from the E7 region of HPV 16 and is comprised of 25 residues made up of amino acids starting at 86-/E2 265- of the HPV 16 E7 oncoprotein having a GGPGG spacer sequence, and having and Cys replaced with Ser, as follows, with the sequence beginning at the amino terminal residue end: (SEQ. ID. No. 30) His Lue Gly Ile Val Ser Pro Ile Ser Ser Gly Gly Pro Gly Gly Leu His Arg Asp Ser Val Asp Ser Ala Glu.

SEQ. ID. No. 31 was derived from the E2 region of HPV 16 and is comprised of 12 residues made up of amino acids starting at 334- of the HPV 16 E2 oncoprotein, as follows, with the sequence beginning at the amino terminal residue end: (SEQ. ID. No. 31) His Thr Leu Thr Tyr Asp Ser Glu Trp Gln Arg Asp.

SEQ. ID. No. 32 was derived from the E2 region of HPV 16 and is comprised of 11 residues made up of amino acids starting at 256- of the HPV 16 E2 oncoprotein, as follows, with the sequence beginning at the amino terminal residue end: (SEQ. ID. No. 32) Lys Leu His Arg Asp Ser Val Asp Ser Ala Glu.

SEQ. ID. No. 33 was derived from the E2 region of HPV 16 and is comprised of 23 residues made up of amino acids at positions 256-/35- of the HPV 16 E2 oncoprotein having a GPG spacer sequence, as follows, with the sequence beginning at the amino terminal residue end: (SEQ. ID. No. 33) Lys Leu His Arg Asp Ser Val Asp Ser Ala Gly Pro Gly Nle Arg Leu Glu Cys Ala Ile Tyr Tyr Glu.

SEQ. ID. No. 34 was derived from the E2 region of HPV 16 and is comprised of 25 residues made up of amino acids starting at 310-/93- of the HPV 16 E2 oncoprotein having a GGPGG spacer sequence, as follows, with the sequence beginning at the amino terminal residue end: (SEQ. ID. No. 34) Lys Thr Leu Tyr Thr Ala Val Ser Ser Thr Gly Gly Pro Gly Gly Thr Leu Gln Asp Val Ser Leu Glu Val Glu.

SEQ. ID. No. 35 was derived from the E2 regions of HPV 16/18 and is comprised of 25 residues made up of amino acids starting at 310-/7- of the HPV 16/18 E2 oncoprotein having a GGPGG spacer sequence, as follows, with the sequence beginning at the amino terminal residue end: (SEQ. ID. No. 35) Lys Thr Leu Tyr Thr Ala Val Ser Ser Thr Gly Gly Pro Gly Gly Thr Leu Ser Glu Arg Leu Ser Ser Val Glu.

SEQ. ID. No. 36 was derived from the E2 region of HPV 16/18 and is comprised of 25 residues made up of amino acids starting at 93-/7- of the HPV 16/18 E2 oncoprotein having a GGPGG spacer sequence, as follows, with the sequence beginning at the amino terminal residue end: (SEQ. ID. No. 36) Lys Thr Leu Gln Asp Val Ser Leu Glu Val Gly Gly Pro Gly Gly Thr Leu Ser Glu Arg Leu Ser Ser Val Glu.

SEQ. ID. No. 37 was derived from the E2 and E7 region of HPV 16 and is comprised of 24 residues made up of amino acids starting at 93-/11- of the HPV 16 E2/E7 oncoprotein having a GGPGG spacer sequence, and having Met replaced with Nle, as follows, with the sequence beginning at the amino terminal residue end: (SEQ. ID. No. 37) Lys Thr Leu Gln Asp Val Ser Leu Val Gly Gly Pro Gly Gly Tyr Nle Leu Asp Leu Gln Pro Glu Thr Asp.

SEQ. ID. No. 38 was derived from the E2 and E7 region of HPV 16 and is comprised of 25 residues made up of amino acids starting at 310-/7- of the HPV 16 E2/E7 oncoprotein having Met replaced with Nle, as follows, with the sequence beginning at the amino terminal residue end: (SEQ. ID. No. 38) Lys Thr Leu Tyr Thr Ala Val Ser Ser Thr Gly Gly Pro Gly Gly Thr Leu His Glu Tyr Nle Leu Asp Leu Arg.

SEQ. ID. No. 39 was derived from the E2 and E7 region of HPV 16 and is comprised of 26 residues made up of amino acids starting at 93-/7- of the HPV 16 E2/E7 oncoprotein having a GGPGG spacer sequence, as follows, with the sequence beginning at the amino terminal residue end: (SEQ. ID. No. 39) Lys Thr Leu Gln Asp Val Ser Leu Glu Val Gly Gly Pro Gly Gly Thr Leu His Glu Tyr Nle Leu Asp Leu Arg Glu.

SEQ. ID. No. 40 was derived from the E2 region of HPV 18 and is comprised of 11 residues made up of amino acids starting at 135- of the HPV 18 E2 oncoprotein having Met replaced with Nle, as follows, with the sequence beginning at the amino terminal residue end: (SEQ. ID. No. 40) Lys Glu Val Ala Trp Ser Val Tyr Tyr Nle Asp.

SEQ. ID. No. 41 was derived from the E2 region of HPV 18 and is comprised of 13 residues made up of amino acids starting at 355- of the HPV 18 E2 oncoprotein having Met replaced with Nle, as follows, with the sequence beginning at the amino terminal residue end: (SEQ. ID. No. 41) Arg Val Gln Ile Leu Leu Val Gly Tyr Nle Thr Asn Glu.

SEQ. ID. No. 42 was derived from the E2 region of HPV 18 and is comprised of 12 residues made up of amino acids starting at 7- of the HPV 18 E2 oncoprotein, as follows, with the sequence beginning at the amino terminal residue end: (SEQ. ID. No. 42) Lys Thr Leu Ser Glu Arg Leu Ser Ser Val Arg Glu.

SEQ. ID. No. 43 was derived from the E7 and E2 region of HPV 18 and is comprised of 24 residues made up of amino acids starting at 7-/7- of the HPV 18 E7/E2 oncoprotein having a GGPGG spacer sequence, as follows, with the sequence beginning at the amino terminal residue end: (SEQ. ID. No. 43) Lys Thr Leu Gln Asp Ile Val Leu His Gly Gly Pro Gly Gly Thr Leu Ser Glu Arg Leu Ser Ser Val Glu.

SEQ. ID. No. 44 was derived from the E2 region of HPV 18/16 and is comprised of 25 residues made up of amino acids starting at 355-/256- of the HPV 18/16 E2 oncoprotein having a GGPGG spacer sequence, and having Met replaced with Nle, as follows, with the sequence beginning at the amino terminal residue end: (SEQ. ID. No. 44) Lys Val Gln Ile Leu Val Gly Tyr Nle Thr Gly Gly Pro Gly Gly Leu His Arg Asp Ser Val Asp Ser Gly Asp.

SEQ. ID. No. 45 was derived from the E2 region of HPV 18/16 and is comprised of 27 residues made up of amino acids starting at 7-/93- of the HPV 18/16 E2 oncoprotein having a GGPGG spacer sequence, as follows, with the sequence beginning at the amino terminal residue end: (SEQ. ID. No. 45) Lys Thr Leu Ser Glu Arg Leu Ser Ser Val Gly Gly Pro Gly Gly Lys Thr Leu Gln Asp Val Ser Leu Glu Val Arg Asp.

SEQ. ID. No. 46 was derived from the E7 region of HPV 16/18 and is comprised of 25 residues made up of amino acids starting at 7-/7- of the HPV 16/18 E7 oncoprotein having a GGPGG spacer sequence, and having Met replaced with Nle, as follows, with the sequence beginning at the amino terminal residue end: (SEQ. ID. No. 46) Arg Thr Leu His Glu Tyr Nle Leu Asp Leu Gly Gly Pro Gly Gly Thr Leu Gln Asp Ile Val Leu His Leu Glu.

SEQ. ID. No. 47 was derived from the E7 region of HPV 16/18 and is comprised of 25 residues made up of amino acids starting at 7-/86- of the HPV 16/18 E7 oncoprotein having a GGPGG spacer sequence, and having Met replaced with Nle, as follows, with the sequence beginning at the amino terminal residue end: (SEQ. ID. No. 47) Lys Thr Leu His Glu Tyr Nle Leu Asp Leu Gly Gly Pro Gly Gly Phe Gln Gln Leu Phe Leu Asn Thr Leu Glu.

SEQ. ID. No. 48 was derived from the E6 region of HPV 16/18 and is comprised of 23 residues made up of amino acids starting at 18-/13- of the HPV 16/18 E6 oncoprotein having a GGPGG spacer sequence, and having and Cys replaced with Ser, as follows, with the sequence beginning at the amino terminal residue end: (SEQ. ID. No.48) Lys Leu Pro Gln Ser Thr Glu Leu Gly Gly Pro Gly Gly Lys Leu Pro Asp Leu Ser Thr Glu Leu Asp.

SEQ. ID. No. 49 was derived from the E6 region of HPV 16/18 and is comprised of 23 residues made up of amino acids starting at 79-/13- of the HPV 16/18 E6 oncoprotein having a GGPGG spacer sequence, and having and Cys replaced with Ser, as follows, with the sequence beginning at the amino terminal residue end: (SEQ. ID. No. 49) Lys Ile Ser Glu Tyr Arg His Tyr Ser Gly Gly Pro Gly Gly Lys Pro Asp Leu Ser Thr Glu Leu Glu.

SEQ. ID. No. 50 was derived from the E4 region of HPV 16/18 and is comprised of 24 residues made up of amino acids starting at 17-/44- of the HPV 16/18 E4 oncoprotein having a GGPGG spacer sequence, as follows, with the sequence beginning at the amino terminal residue end: (SEQ. ID. No. 50) Lys Leu Leu Gly Ser Thr Trp Pro Thr Gly Gly Pro Gly Gly Arg Leu Leu His Asp Leu Asp Thr Val Glu.

SEQ. ID. No. 51 was derived from the E7 and E6 region of HPV 16 and is comprised of 25 residues made up of amino acids starting at 7-/18- of the HPV 16 E7/E6 oncoprotein having a GGPGG spacer sequence, and having and Cys replaced with Ser, as follows, with the sequence beginning at the amino terminal residue end: (SEQ. ID. No. 51) Lys Thr Leu His Glu Tyr Nle Leu Asp Leu Gly Gly Pro Gly Gly Lys Leu Pro Gln Leu Ser Thr Glu Leu Glu.

SEQ. ID. No. 52 was derived from the E6 and E2 region of HPV 16 and is comprised of 24 residues made up of amino acids starting at 18-/93- of the HPV 16 E6/E2 oncoprotein having a GGPGG spacer sequence, as follows, with the sequence beginning at the amino terminal residue end: (SEQ. ID. No. 52) Lys Leu Pro Gln Leu Ser Thr Glu Leu Gly Gly Pro Gly Gly Thr Leu Gln Asp Val Ser Leu Glu Val Glu.

SEQ. ID. No. 53 was derived from the E6 and E4 region of HPV 16 and is comprised of 24 residues made up of amino acids starting at 18-/17- of the HPV 16 E6/E4 oncoprotein having a GGPGG spacer sequence, as follows, with the sequence beginning at the amino terminal residue end: (SEQ. ID. No. 53) Lys Leu Pro Gln Leu Ser Thr Glu Leu Gly Gly Pro Gly Gly Lys Leu Leu Gly Ser Thr Trp Pro Thr Glu.

SEQ. ID. No. 54 was derived from the E6 and E4 region of HPV 16 and is comprised of 24 residues made up of amino acids starting at 79-/17- of the HPV 16 E6/E4 oncoprotein having a GGPGG spacer sequence, as follows, with the sequence beginning at the amino terminal residue end: (SEQ. ID. No. 54) Lys Ile Ser Glu Tyr Arg His Tyr Ser Gly Gly Pro Gly Gly Lys Leu Leu Gly Ser Thr Trp Pro Thr Glu.

SEQ. ID. No. 55 was derived from the E2 and E7 region of HPV 18 and is comprised of 25 residues made up of amino acids starting at 7-/7- of the HPV 18 E2/E7 oncoprotein having a GGPGG spacer sequence, as follows, with the sequence beginning at the amino terminal residue end: (SEQ. ID. No. 55) Lys Thr Leu Ser Glu Arg Leu Ser Ser Val Gly Gly Pro Gly Gly Thr Leu Gln Asp Ile Val Leu His Leu Asp.

SEQ. ID. No. 56 was derived from the E6 and E4 region of HPV 18 and is comprised of 24 residues made up of amino acids starting at 13/44 of the HPV 18 E6/E4 oncoprotein having a GGPGG spacer sequence, as follows, with the sequence beginning at the amino terminal residue end: (SEQ. ID. No. 56) Lys Leu Pro Asp Leu Ser Thr Glu Leu Gly Gly Pro Gly Gly Arg Leu Leu His Asp Leu Asp Thr Val Glu.

SEQ. ID. No. 57 was derived from the E7 and E6 region of HPV 18 and is comprised of 25 residues made up of amino acids starting at 7-/13- of the HPV 18 E7/E6 oncoprotein having a GGPGG spacer sequence, as follows, with the sequence beginning at the amino terminal residue end: (SEQ. ID. No. 57) Lys Thr Leu Gln Asp Ile Val Leu His Leu Gly Gly Pro Gly Gly Lys Leu Pro Asp Leu Ser Thr Glu Leu Asp.

SEQ. ID. No. 58 was derived from the E2 and E6 region of HPV 18 and is comprised of 25 residues made up of amino acids starting at 7-/13- of the HPV 18 E2/E6 oncoprotein having a GGPGG spacer sequence, and having and Cys replaced with Ser, as follows, with the sequence beginning at the amino terminal residue end: (SEQ. ID. No. 58) Lys Thr Leu Ser Glu Arg Leu Ser Ser Val Gly Gly Pro Gly Gly Lys Leu Pro Asp Leu Ser Thr Glu Leu Asp.

SEQ. ID. No. 59 was derived from the E6 and E2 region of HPV 31 and is comprised of 24 residues made up of amino acids starting at 11-/317- of the HPV 31 E6/E2 oncoprotein having a GGPGG spacer sequence, as follows, with the sequence beginning at the amino terminal residue end: (SEQ. ID. No. 59) Lys Leu His Glu Leu Ser Ser Ala Leu Gly Gly Pro Gly Gly Gln Leu Tyr Glu Gln Val Ser Ser Thr Glu.

SEQ. ID. No. 60 was derived from the E6 and E7 region of HPV 31 and is comprised of 24 residues made up of amino acids starting at 11-/7- of the HPV 31 E6/E7 oncoprotein having a GGPGG spacer sequence, as follows, with the sequence beginning at the amino terminal residue end: (SEQ. ID. No. 60) Lys Leu His Glu Leu Ser Ser Ala Leu Gly Gly Pro Gly Gly Thr Leu Gln Asp Tyr Val Leu Asp Leu Glu.

SEQ. ID. No. 61 was derived from the E2 and E4 region of HPV 31 and is comprised of 25 residues made up of amino acids starting at 317-/7- of the HPV 31 E2/E4 oncoprotein having a GGPGG spacer sequence, as follows, with the sequence beginning at the amino terminal residue end: (SEQ. ID. No. 61) Lys Gln Leu Tyr Glu Gln Val Ser Ser Thr Gly Gly Pro Gly Gly Tyr Leu Ala Val Thr Lys Tyr Pro Leu Glu.

SEQ. ID. No. 62 was derived from the E2 and E4 region of HPV 31 and is comprised of 24 residues made up of amino acids starting at 260-/85- of the HPV 31 E2/E4 oncoprotein having a GGPGG spacer sequence, as follows, with the sequence beginning at the amino terminal residue end: (SEQ. ID. No. 62) Arg Leu Leu Arg Gly Asp Ser Val Asp Ser Gly Gly Pro Gly Gly Leu His Ala Gln Thr Lys Gln Gly Glu.

SEQ. ID. No. 63 was derived from the E2 and E4 region of HPV 31 and is comprised of 24 residues made up of amino acids starting at 260/3 of the HPV 31 E2/E4 oncoprotein having a GGPGG spacer sequence, as follows, with the sequence beginning at the amino terminal residue end: (SEQ. ID. No. 63) Arg Leu Leu Arg Gly Asp Ser Val Asp Ser Gly Gly Pro Gly Gly Leu Arg Leu Tyr Leu Ala Thr Lys Tyr.

SEQ. ID. No. 64 was derived from the E6 and E7 region of HPV 33 and is comprised of 25 residues made up of amino acids starting at 11-/82- of the HPV 33 E6/E7 oncoprotein having a GGPGG spacer sequence, and having Met replaced with Nle, as follows, with the sequence beginning at the amino terminal residue end: (SEQ. ID. No. 64) His Thr Leu His Asp Leu Ser Gln Ala Leu Gly Gly Pro Gly Gly Leu Leu Nle Gly Thr Val Asn Ile Val Glu.

SEQ. ID. No. 65 was derived from the E2 and E7 region of HPV 33 and is comprised of 25 residues made up of amino acids starting at 51-/34- of the HPV 33 E2/E7 oncoprotein having a GGPGG spacer sequence, and having Met replaced with Nle, as follows, with the sequence beginning at the amino terminal residue end: (SEQ. ID. No. 65) Arg Tyr Tyr Ile Val Thr Ser Ser His Thr Gly Gly Pro Gly Gly Leu Ile Arg Nle Glu Cys Ala Leu Leu Glu.

SEQ. ID. No. 66 was derived from the E2 and E7 region of HPV 33 and is comprised of 24 residues made up of amino acids starting at 242-/82- of the HPV 33 E2/E7 oncoprotein having a GGPGG spacer sequence, and having Met replaced with Nle, as follows, with the sequence beginning at the amino terminal residue end: (SEQ. ID. No. 66) Lys Leu Phe Ser Ala Asp Pro Ala Leu Gly Gly Pro Gly Gly Leu Leu Nle Gly Thr Val Ile Asn Val Glu.

SEQ. ID. No. 67 was derived from the E4 and E2 region of HPV 33 and is comprised of 24 residues made up of amino acids starting at 3-/34- of the HPV 33 E4/E2 oncoprotein having a GGPGG spacer sequence, and having Met replaced with Nle and Cys replaced with Ser, as follows, with the sequence beginning at the amino terminal residue end: (SEQ. ID. No. 67) Arg Leu Arg Leu Tyr Leu Ala Thr Lys Gly Gly Pro Gly Gly Leu Ile Arg Nle Glu Ser Ala Leu Leu Glu.

SEQ. ID. No. 68 was derived from the E4 and E2 region of HPV 33 and is comprised of 25 residues made up of amino acids starting at 7/242 of the HPV 33 E4/E2 oncoprotein having a GGPGG spacer sequence, as follows, with the sequence beginning at the amino terminal residue end: (SEQ. ID. No. 68) His Tyr Leu Ala Thr Lys Tyr Pro Leu Leu Gly Gly Pro Gly Gly Lys Leu Phe Ser Ala Asp Pro Ala Leu Glu.

SEQ. ID. No. 69 was derived from the E2 region of HPV 31/33 and is comprised of 25 residues made up of amino acids starting at 260-/34- of the HPV 31/33 E2 oncoprotein having a GGPGG spacer sequence, and having Met replaced with Nle and Cys replaced with Ser, as follows, with the sequence beginning at the amino terminal residue end: (SEQ. ID. No. 69) His Leu Leu Arg Gly Asp Ser Val Asp Ser Gly Gly Pro Gly Gly Leu Ile Arg Nle Glu Ser Ala Leu Leu Glu.

SEQ. ID. No. 70 was derived from the E2 region of HPV 31/33 and is comprised of 25 residues made up of amino acids starting at 317-/242- of the HPV 31/33 E2 oncoprotein having a GGPGG spacer sequence, and having Cys replaced with Ser, as follows, with the sequence beginning at the amino terminal residue end: (SEQ. ID. No. 70) Lys Gln Leu Tyr Lys Gln Val Ser Ser Thr Gly Gly Pro Gly Gly Lys Leu Phe Ser Ala Asp Pro Ala Leu Glu.

SEQ. ID. No. 71 was derived from the E6 region of HPV 31/33 and is comprised of 24 residues made up of amino acids starting at 260/34 of the HPV 31/33 E6 oncoprotein having a GGPGG spacer sequence, as follows, with the sequence beginning at the amino terminal residue end: (SEQ. ID. No. 71) Lys Leu Arg Leu Asn Ser Val Tyr Ser Lys Gly Gly Pro Gly Gly Leu Arg Phe Leu Ser Lys Ile Ser Glu.

SEQ. ID. No. 72 was derived from the E6 region of HPV 31/33 and is comprised of 23 residues made up of amino acids starting at 11-/11- of the HPV 31/33 E6 oncoprotein having a GGPGG spacer sequence, and having Cys replaced with Ser, as follows, with the sequence beginning at the amino terminal residue end: (SEQ. ID. No. 72) Lys Leu His Glu Leu Ser Ser Ala Leu Gly Gly Pro Gly Gly Thr Leu His Asp Leu Ser Gln Ala Leu.

SEQ. ID. No. 73 was derived from the E7 region of HPV 31/33 and is comprised of 25 residues made up of amino acids starting at 75-/51- of the HPV 31/33 E7 oncoprotein having a GGPGG spacer sequence, and having Met replaced with Nle, as follows, with the sequence beginning at the amino terminal residue end: (SEQ. ID. No. 73) His Ile Arg Ile Leu Gln Glu Leu Leu Nle Gly Gly Pro Gly Gly Tyr Tyr Ile Val Thr Ser Ser His Thr Asp.

SEQ. ID. No. 74 was derived from the E7 region of HPV 31/33 and is comprised of 25 residues made up of amino acids starting at 75-/75- of the HPV 31/33 E7 oncoprotein having a GGPGG spacer sequence, and having Met replaced with Nle, as follows, with the sequence beginning at the amino terminal residue end: (SEQ. ID. No. 74) His Tyr Val Leu Asp Leu Gln Pro Glu Ala Gly Gly Pro Gly Gly Leu Arg Thr Ile Gln Gln Leu Leu Nle Glu.

SEQ. ID. No. 75 was derived from the E7 region of HPV 31/33 and is comprised of 25 residues made up of amino acids starting at 7-/82- of the HPV 31/33 E7 oncoprotein having a GGPGG spacer sequence, and having Met replaced with Nle, as follows, with the sequence beginning at the amino terminal residue end: (SEQ. ID. No. 75) Arg Thr Leu Gln Asp Tyr Val Leu Asp Leu Gly Gly Pro Gly Gly Leu Leu Nle Gly Thr Val Asn Ile Val Glu.

SEQ. ID. No. 76 was derived from the E4 region of HPV 31/33 and is comprised of 25 residues made up of amino acids starting at 74/63 of the HPV 31/33 E4 oncoprotein, having a GGPGG spacer sequence, as follows, with the sequence beginning at the amino terminal residue end: (SEQ. ID. No. 76) Lys Trp Thr Val Ser Thr Val Gly Leu Ser Gly Gly Pro Gly Gly Val Leu Gln Leu Thr Ala Gln Thr Ser Glu.

SEQ. ID. No. 77 was derived from the E4 region of HPV 31/33 and is comprised of 24 residues made up of amino acids starting at 49-/-3- of the HPV 31/33 E4 oncoprotein having a GGPGG spacer sequence, as follows, with the sequence beginning at the amino terminal residue end: (SEQ. ID. No. 77) Lys Leu Leu Ser Asp Gln Glu Gln Ser Gln Gly Gly Pro Gly Gly Leu Arg Leu Tyr Leu Ala Thr Lys Asp.

SEQ. ID. No. 78 was derived from the E4 region of HPV 31/33 and is comprised of 25 residues made up of amino acids starting at 7/7 of the HPV 31/33 E4 oncoprotein having a GGPGG spacer sequence, as follows, with the sequence beginning at the amino terminal residue end: (SEQ. ID. No. 78) Lys Tyr Leu Ala Val Thr Lys Tyr Pro Leu Gly Gly Pro Gly Gly Tyr Leu Ala Thr Lys Tyr Pro Leu Leu Asp.

SEQ. ID. No. 79 was derived from the E7 and E6 region of HPV 52 and is comprised of 23 residues made up of amino acids starting at 85-/45- of the HPV 52 E7/E6 oncoprotein having a GGPGG spacer sequence, and having Met replaced with Nle, as follows, with the sequence beginning at the amino terminal residue end: (SEQ. ID. No. 79) Gln Nle Leu Leu Gly Thr Leu Gln Val Gly Gly Pro Gly Gly Leu Phe Thr Asp Leu Arg Ile Val Tyr.

SEQ. ID. No. 80 was derived from the E7 and E6 region of HPV 52 and is comprised of 24 residues made up of amino acids starting at 84-/45- of the HPV 52 E7/E6 oncoprotein having a GGPGG spacer sequence, as follows, with the sequence beginning at the amino terminal residue end: (SEQ. ID. No. 80) Lys Nle Leu Leu Gly Thr Leu Gln Val Val Gly Gly Pro Gly Gly Leu Phe Thr Asp Leu Arg Ile Val Tyr.

SEQ. ID. No. 81 was derived from the E6 region of HPV 52/58 and is comprised of 25 residues made up of amino acids starting at 45-/11- of the HPV 52/58 E6 oncoprotein having a GGPGG spacer sequence, as follows, with the sequence beginning at the amino terminal residue end: (SEQ. ID. No. 81) Lys Leu Phe Thr Asp Leu Arg Ile Val Tyr Gly Gly Pro Gly Gly Thr Leu His Asp Leu Ser Gln Ala Leu Glu.

SEQ. ID. No. 82 was derived from the E6 region of HPV 52/58 and is comprised of 25 residues made up of amino acids starting at 45-/95- of the HPV 52/58 E6 oncoprotein having a GGPGG spacer sequence, and having and Cys replaced with Ser, as follows, with the sequence beginning at the amino terminal residue end: (SEQ. ID. No. 82) Lys Leu Phe Thr Asp Leu Arg Ile Val Tyr Gly Gly Pro Gly Gly Ser Leu Asn Glu Ile Leu Ile Arg Ser Asp.

SEQ. ID. No. 83 was derived from the E7 region of HPV 52 and is comprised of 24 residues made up of amino acids starting at 10-/1- of the HPV 52 E7 oncoprotein having a GGPGG spacer sequence, and having Met replaced with Nle, as follows, with the sequence beginning at the amino terminal residue end: (SEQ. ID. No. 83) His Tyr Ile Leu Asp Leu Gln Pro Glu Thr Gly Gly Pro Gly Gly Nle Arg Glu Asp Lys Ala Thr Ile Lys.

SEQ. ID. No. 84 was derived from the E7 region of HPV 52 and is comprised of 24 residues made up of amino acids starting at 66-/1- of the HPV 52 E7 oncoprotein having a GGPGG spacer sequence, and having Met replaced with Nle, as follows, with the sequence beginning at the amino terminal residue end: (SEQ. ID. No. 84) His Leu Arg Leu Ser Ile His Ser Thr Ala Gly Gly Pro Gly Gly Nle Arg Gly Asp Lys Ala Thr Ile Lys.

SEQ. ID. No. 85 was derived from the E7 region of HPV 52/58 and is comprised of 24 residues made up of amino acids starting at 25-/1- of the HPV 52/58 E7 oncoprotein having a GGPGG spacer sequence, and having Met replaced with Nle, as follows, with the sequence beginning at the amino terminal residue end: (SEQ. ID. No. 85) Lys Ile Gly Leu Asp Gly Pro Asp Gly Gln Gly Gly Pro Gly Gly Nle Arg Gly Asp Lys Ala Thr Ile Lys.

SEQ. ID. No. 86 was derived from the E7 region of HPV 52/58 and is comprised of 33 residues made up of amino acids starting at 1-/36- of the HPV 52/58 E7 oncoprotein having a GGPGG spacer sequence, and having Met replaced with Nle, as follows, with the sequence beginning at the amino terminal residue end: (SEQ. ID. No. 86) Lys Nle Arg Gly Asp Lys Ala Thr Lys Nle Arg Gly Asp Lys Ala Thr Ile Lys Gly Gly Pro Gly Gly Ile Gly Leu Asp Gly Pro Asp Gly Gln Glu.

SEQ. ID. No. 87 was derived from the E7 region of HPV 52/58 and is comprised of 25 residues made up of amino acids starting at 1-/82- of the HPV 52/58 E7 oncoprotein having a GGPGG spacer sequence, and having Met replaced with Nle and Cys replaced with Ser, as follows, with the sequence beginning at the amino terminal residue end: (SEQ. ID. No. 87) Lys Nle Arg Gly Asp Lys Ala Thr Ile Lys Gly Gly Pro Gly Gly Leu Leu Nle Gly Thr Ser Thr Ile Val Glu.

SEQ. ID. No. 88 was derived from the E7 region of HPV 52/58 and is comprised of 25 residues made up of amino acids starting at 84-/82- of the HPV 52/58 E7 oncoprotein having a GGPGG spacer sequence, and having Met replaced with Nle and Cys replaced with Ser, as follows, with the sequence beginning at the amino terminal residue end: (SEQ. ID. No. 88) His Nle Leu Leu Gly Thr Leu Gln Val Val Gly Gly Pro Gly Gly Leu Leu Nle Gly Thr Ser Thr Ile Val Glu.

SEQ. ID. No. 89 was derived from the E2 region of HPV 52 and is comprised of 25 residues made up of amino acids starting at 358-/332- of the HPV 52 E2 oncoprotein having Met replaced with Nle, as follows, with the sequence beginning at the amino terminal residue end: (SEQ. ID. No. 89) Arg Val Gln Val Ile Gln Gly Val Nle Ser Gly Gly Pro Gly Gly Leu Gly Ile Val Thr Ile Thr Tyr Ser Glu.

SEQ. ID. No. 90 was derived from the E2 region of HPV 52 and is comprised of 25 residues made up of amino acids starting at 358-/170- of the HPV 52 E2 oncoprotein having a GGPGG spacer sequence, and having Met replaced with Nle, as follows, with the sequence beginning at the amino terminal residue end: (SEQ. ID. No. 90) Arg Val Gln Val Ile Gln Gly Val Nle Ser Gly Gly Pro Gly Gly Phe Ser Asn Asp Ala Lys Gln Tyr Ser Asp.

SEQ. ID. No. 91 was derived from the E2 region of HPV 52 and is comprised of 25 residues made up of amino acids starting at 255-/332- of the HPV 52 E2 oncoprotein having a GGPGG spacer sequence, as follows, with the sequence beginning at the amino terminal residue end: (SEQ. ID. No. 91) Lys Leu Arg Gly Gln Gln Ser Val Asp Ser Gly Gly Pro Gly Gly Leu Gly Ile Val Thr Ile Thr Tyr Ser Asp.

SEQ. ID. No. 92 was derived from the E2 region of HPV 52, 58 and is comprised of 25 residues made up of amino acids starting at 54-/41- of the HPV 52 E2 oncoprotein having a GGPGG spacer sequence, as follows, with the sequence beginning at the amino terminal residue end: (SEQ. ID. No. 92) Lys Asn Leu Leu Arg Gly Gln Gln Ser Val Gly Gly Pro Gly Gly Val Leu Phe Tyr Lys Ala Lys Glu Leu Glu.

SEQ. ID. No. 93 was derived from the E2 regions of HPV 52 and 58 and is comprised of 25 residues made up of amino acids starting at 255-/348- of the HPV 52/58 E2 oncoprotein having a GGPGG spacer sequence, and having Met replaced with Nle, as follows, with the sequence beginning at the amino terminal residue end: (SEQ. ID. No. 93) Lys Leu Arg Gly Gln Gln Ser Val Asp Ser Gly Gly Pro Gly Gly Val Gln Ile Ser Thr Gly Val Nle Ser Glu.

SEQ. ID. No. 94 was derived from the E2 regions of HPV 52 and 58 and is comprised of 25 residues made up of amino acids starting at 54-/93- of the HPV 52/58 E2 oncoprotein having a GGPGG spacer sequence, as follows, with the sequence beginning at the amino terminal residue end: (SEQ. ID. No. 94) Lys Asn Leu Leu Arg Gly Gln Gln Ser Val Gly Gly Pro Gly Gly Thr Leu Gln Gln Thr Ser Leu Glu Val Glu.

SEQ. ID. No. 95 was derived from the E4 region of HPV 58 and is comprised of 25 residues made up of amino acids starting at 7-/5- of the HPV 58 E4 oncoprotein having a GGPGG spacer sequence, as follows, with the sequence beginning at the amino terminal residue end: (SEQ. ID. No. 95) Lys Leu Val Ile Lys Tyr Pro Leu Leu Lys Gly Gly Pro Gly Gly Leu Tyr Leu Val Ile Lys Tyr Pro Leu Glu.

SEQ. ID. No. 96 was derived from the E4 region of HPV 58 and is comprised of 26 residues made up of amino acids starting at 7-/53- of the HPV 58 E4 oncoprotein having a GGPGG spacer sequence, as follows, with the sequence beginning at the amino terminal residue end: (SEQ. ID. No. 96) Lys Leu Val Ile Lys Tyr Pro Leu Leu Lys Gly Gly Pro Gly Gly Ser Ile Gln Thr Ala Pro Typ Thr Thr Val Glu.

SEQ. ID. No. 97 was derived from the E7 region of HPV 58 and is comprised of 24 residues made up of amino acids starting at 52-/36- of the HPV 58 E7 oncoprotein having a GGPGG spacer sequence, as follows, with the sequence beginning at the amino terminal residue end: (SEQ. ID. No. 97) His Tyr Tyr Ile Val Thr Ser Ser Tyr Thr Gly Gly Pro Gly Gly Ile Gly Leu Asp Gly Pro Asp Gly Gln.

SEQ. ID. No. 98 was derived from the E7 region of HPV 58 and is comprised of 25 residues made up of amino acids starting at 82-/10- of the HPV 58 E7 oncoprotein having a GGPGG spacer sequence, and having Met replaced with Nle, as follows, with the sequence beginning at the amino terminal residue end: (SEQ. ID. No. 98) Lys Leu Leu Nle Gly Thr Ser Thr Ile Val Gly Gly Pro Gly Gly Tyr Ley Leu Asp Leu His Pro Glu Pro Asp.

SEQ. ID. No. 99 was derived from the E6 region of HPV 58 and is comprised of 25 residues made up of amino acids starting at 49-/100- of the HPV 58 E6 oncoprotein having a GGPGG spacer sequence, and having Cys replaced with Ser, as follows, with the sequence beginning at the amino terminal residue end: (SEQ. ID. No. 99) Lys Leu Arg Ile Val Tyr Arg Asp Gly Asn Gly Gly Pro Gly Gly Ile Arg Ser Ile Ile Ser Gln Arg Pro Glu.

SEQ. ID. No. 100 was derived from the E6 region of HPV 58 and is comprised of 25 residues made up of amino acids starting at 100-/66- of the HPV 58 E6 oncoprotein having a GGPGG spacer sequence, and having Cys replaced with Ser, as follows, with the sequence beginning at the amino terminal residue end: (SEQ. ID. No. 100) Arg Ile Arg Ser Ile Ile Ser Gln Arg Pro Glu Gly Gly Pro Gly Gly Leu Arg Leu Leu Ser Lys Ile Ser Glu.

SEQ. ID. No. 101 was derived from the E6 region of HPV 58 and is comprised of 24 residues made up of amino acids starting at 49-/66- of the HPV 58 E6 oncoprotein having a GGPGG spacer sequence, as follows, with the sequence beginning at the amino terminal residue end: (SEQ. ID. No. 101) Lys Leu Arg Ile Val Tyr Arg Asp Gly Asn Gly Gly Pro Gly Gly Leu Arg Leu Leu Ser Lys Ile Ser Glu.

SEQ. ID. No. 102 was derived from the E2 region of HPV 58 and is comprised of 24 residues made up of amino acids starting at 348-/35- of the HPV 58 E2 oncoprotein having a GGPGG spacer sequence, and having Met replaced with Nle and Cys replaced with Ser, as follows, with the sequence beginning at the amino terminal residue end: (SEQ. ID. No. 102) Lys Val Gln Ile Ser Thr Gly Val Nle Ser Gly Gly Pro Gly Gly Ile Arg Nle Glu Ser Ala Ile Nle Tyr.

SEQ. ID. No. 103 was derived from the E2 region of HPV 58 and is comprised of 24 residues made up of amino acids starting at 348-/48- of the HPV 58 E2 oncoprotein having a GGPGG spacer sequence, and having Met replaced with Nle and Cys replaced with Ser, as follows, with the sequence beginning at the amino terminal residue end: (SEQ. ID. No. 103) Arg Val Gln Ile Ser Thr Gly Val Nle Ser Gly Gly Pro Gly Gly Nle Gly Ile Ser His Leu Ser His Gln.

SEQ. ID. No. 104 was derived from the E6 region of HPV 45 and is comprised of 25 residues made up of amino acids starting at 102-/54- of the HPV 45 E6 oncoprotein having a GGPGG spacer sequence, as follows, with the sequence beginning at the amino terminal residue end: (SEQ. ID. No. 104) Lys Ile Arg Ser Leu Arg Ser Gln Lys Pro Gly Gly Pro Gly Gly Val Tyr Arg Asp Ser Ile Ala Tyr Ala Asp.

SEQ. ID. No. 105 was derived from the E6 region of HPV 45 and is comprised of 24 residues made up of amino acids starting at 13-/24- of the HPV 45 E6 oncoprotein having a GGPGG spacer sequence, and having Cys replaced with Ser, as follows, with the sequence beginning at the amino terminal residue end: (SEQ. ID. No. 105) Lys Leu Pro Asp Leu Ser Thr Glu Leu Gly Gly Pro Gly Gly Ser Leu Gln Asp Val Ser Ile Ala Ser Glu.

SEQ. ID. No. 106 was derived from the E7 region of HPV 45 and is comprised of 25 residues made up of amino acids starting at 89-/83- of the HPV 45 E7 oncoprotein having a GGPGG spacer sequence, as follows, with the sequence beginning at the amino terminal residue end: (SEQ. ID. No. 106) Lys Leu Phe Leu Ser Thr Leu Ser Phe Val Gly Gly Pro Gly Gly Leu Arg Thr Leu Gln Gln Leu Phe Leu Glu.

SEQ. ID. No. 107 was derived from the E7 region of HPV 45 and is comprised of 24 residues made up of amino acids starting at 7-/91- of the HPV 45 E7 oncoprotein having a GGPGG spacer sequence, as follows, with the sequence beginning at the amino terminal residue end: (SEQ. ID. No. 107) Arg Thr Leu Gln Glu Ile Val Leu His Leu Gly Gly Pro Gly Gly Phe Leu Ser Thr Leu Ser Phe Val Ser.

SEQ. ID. No. 108 was derived from the E6 and E7 regions of HPV 45 and is comprised of 25 residues made up of amino acids starting at 83-/54- of the HPV 45 E7/E6 oncoprotein having a GGPGG spacer sequence, as follows, with the sequence beginning at the amino terminal residue end: (SEQ. ID. No. 108) Lys Leu Arg Thr Leu Gln Gln Leu Phe Leu Gly Gly Pro Gly Gly Val Tyr Arg Asp Ser Ile Ala Tyr Ala Asp.

SEQ. ID. No. 109 was derived from the E6 and E7 regions of HPV 45 and is comprised of 23 residues made up of amino acids starting at 7-/24- of the HPV 45 E7/E6 oncoprotein having a GGPGG spacer sequence, as follows, with the sequence beginning at the amino terminal residue end: (SEQ. ID. No. 109) Thr Leu Gln Glu Ile Val Leu His Leu Gly Gly Pro Gly Gly Ser Leu Gln Asp Val Ser Ile Ala Ser.

SEQ. ID. No. 110 was derived from the E2 region of HPV 45 and is comprised of 25 residues made up of amino acids starting at 218-/137- of the HPV 45 E2 oncoprotein having a GGPGG spacer sequence, as follows, with the sequence beginning at the amino terminal residue end: (SEQ. ID. No. 110) Lys Ile Val Arg Gln Leu Gln His Ala Ser Gly Gly Pro Gly Gly Val Val Trp Asp Ser Ile Tyr Tyr Ile Glu.

SEQ. ID. No. 111 was derived from the E2 region of HPV 45 and is comprised of 25 residues made up of amino acids starting at 138-/9- of the HPV 45 E2 oncoprotein having a GGPGG spacer sequence, as follows, with the sequence beginning at the amino terminal residue end: (SEQ. ID. No. 111) Lys Val Val Trp Asp Ser Ile Tyr Tyr Ile Gly Gly Pro Gly Gly Ser Leu Ser Glu Arg Leu Ser Ala Arg Glu.

SEQ. ID. No. 112 was derived from the E2 and E4 regions of HPV 45 and is comprised of 26 residues made up of amino acids starting at 14-/218- of the HPV 45 E4/E2 oncoprotein having a GGPGG spacer sequence, as follows, with the sequence beginning at the amino terminal residue end: (SEQ. ID. No. 112) Arg Leu Arg Leu Leu Asp Ser Tyr Asn Thr Gly Gly Pro Gly Gly Lys Ile Val Arg Gln Leu Gln His Ala Ser Asp.

SEQ. ID. No. 113 was derived from the E2 and E4 regions of HPV 45 and is comprised of 25 residues made up of amino acids starting at 138-/44- of the HPV 45 E2/E4 oncoprotein having a GGPGG spacer sequence, as follows, with the sequence beginning at the amino terminal residue end: (SEQ. ID. No. 113) Lys Val Val Trp Asp Ser Ile Tyr Tyr Ile Gly Gly Pro Gly Gly Arg Leu Leu Ser Asp Leu Asp Ser Val Glu.

SEQ. ID. No. 114 was derived from the E6 regions of HPV 31 and 45 and is comprised of 25 residues made up of amino acids starting at 260-/54- of the HPV 31/45 E6 oncoprotein having a GGPGG spacer sequence, as follows, with the sequence beginning at the amino terminal residue end: (SEQ. ID. No. 114) Lys Leu Arg Leu Asn Ser Val Tyr Ser Lys Gly Gly Pro Gly Gly Val Tyr Arg Asp Ser Ile Ala Tyr Ala Glu.

SEQ. ID. No. 115 was derived from the E6 regions of HPV 31 and 45 and is comprised of 23 residues made up of amino acids starting at 11-/24- of the HPV 31/45 E6 oncoprotein having a GGPGG spacer sequence, as follows, with the sequence beginning at the amino terminal residue end: (SEQ. ID. No. 115) Lys Leu His Glu Ser Ser Ala Leu Gly Gly Pro Gly Gly Ser Leu Gln Asp Val Ser Ile Ala Ser Glu.

SEQ. ID. No. 116 was derived from the E7 regions of HPV 31 and 45 and is comprised of 24 residues made up of amino acids starting at 25-/54- of the HPV 31/45 E7 oncoprotein having a GGPGG spacer sequence, as follows, with the sequence beginning at the amino terminal residue end: (SEQ. ID. No. 116) His Leu Arg Leu Asn Ser Val Ser Lys Gly Gly Pro Gly Gly Val Tyr Arg Asp Ser Ile Ala Tyr Ala Asp.

SEQ. ID. No. 117 was derived from the E7 regions of HPV 31 and 45 and is comprised of 25 residues made up of amino acids starting at 7-/7- of the HPV 31/45 E7 oncoprotein having a GGPGG spacer sequence, as follows, with the sequence beginning at the amino terminal residue end: (SEQ. ID. No. 117) His Thr Leu Gln Asp Tyr Val Leu Asp Leu Gly Gly Pro Gly Gly Thr Leu Gln Glu Ile Val Leu His Leu Asp.

SEQ. ID. No. 18 was derived from the E6 regions of HPV 16 and 58 and is comprised of 25 residues made up of amino acids starting at 105-/49- of the HPV 16/58 E6 oncoprotein having a GGPGG spacer sequence, as follows, with the sequence beginning at the amino terminal residue end: (SEQ. ID. No. 118) Lys Leu Leu Ile Arg Ser Ile Asn Ser Gln Gly Gly Pro Gly Gly Leu Arg Ile Val Tyr Arg Asp Gly Asn Glu.

SEQ. ID. No. 119 was derived from the E6 regions of HPV 16 and 58 and is comprised of 25 residues made up of amino acids starting at 107-/100- of the HPV 16/58 E6 oncoprotein having a GGPGG spacer sequence, as follows, with the sequence beginning at the amino terminal residue end: (SEQ. ID. No. 119) Lys Ile Arg Ser Ile Asn Ser Gln Lys Pro Gly Gly Pro Gly Gly Ile Arg Ser Ile Ile Ser Gln Arg Pro Glu.

SEQ. ID. No. 120 was derived from the E6 regions of HPV 16 and 58 and is comprised of 24 residues made up of amino acids starting at 59-/66- of the HPV 16/58 E6 oncoprotein having a GGPGG spacer sequence, as follows, with the sequence beginning at the amino terminal residue end: (SEQ. ID. No. 120) Lys Val Tyr Arg Asp Gly Asn Pro Tyr Ala Gly Gly Pro Gly Gly Leu Arg Leu Leu Ser Lys Ile Ser Glu.

SEQ. ID. No. 121 was derived from the E6 regions of HPV 16 and 58 and is comprised of 25 residues made up of amino acids starting at 59-/49- of the HPV 16/58 E6 oncoprotein having a GGPGG spacer sequence, as follows, with the sequence beginning at the amino terminal residue end: (SEQ. ID. No. 121) Lys Val Tyr Arg Asp Gly Asn Pro Tyr Ala Gln Gly Gly Pro Gly Gly Leu Arg Ile Val Tyr Arg Asp Gly Asn.

SEQ. ID. No. 122 was derived from the E6 regions of HPV 16 and 58 and is comprised of 24 residues made up of amino acids starting at 79-/11- of the HPV 16/58 E6 oncoprotein having a GGPGG spacer sequence, as follows, with the sequence beginning at the amino terminal residue end: (SEQ. ID. No. 122) Lys Ile Ser Glu Tyr Arg His Tyr Ser Gly Gly Pro Gly Gly Thr Leu His Asp Leu Ser Gln Ala Leu Glu.

SEQ. ID. No. 123 was derived from the E6 region of HPV 6 and is comprised of 25 residues made up of amino acids starting at 26-/54- of the HPV 6 E6 oncoprotein having a GGPGG spacer sequence, as follows, with the sequence beginning at the amino terminal residue end: (SEQ. ID. No. 123) His Leu Gln Ile Asn Ser Val Phe Ser Lys Gly Gly Pro Gly Gly Phe Arg Gly Gly Tyr Pro Tyr Ala Ala Glu.

SEQ. ID. No. 124 was derived from the E6 region of HPV 6 and is comprised of 25 residues made up of amino acids starting at 26-/21- of the HPV 6 E6 oncoprotein having a GGPGG spacer sequence, and having Met replaced with Nle and Cys replaced with Ser, as follows, with the sequence beginning at the amino terminal residue end: (SEQ. ID. No. 124) Arg Leu Gln Ile Asn Ser Val Phe Ser Lys Gly Gly Pro Gly Gly Asn Leu Ser Nle His Thr Leu Gln Ile Glu.

SEQ. ID. No. 125 was derived from the E7 region of HPV 6 and is comprised of 25 residues made up of amino acids starting at 10-/86- of the HPV 6 E7 oncoprotein having a GGPGG spacer sequence, as follows, with the sequence beginning at the amino terminal residue end: (SEQ. ID. No. 125) Arg Ile Val Leu Asp Leu Gln Pro Pro Asp Gly Gly Pro Gly Gly Leu Asn Ile Val Ser Pro Ile Ser Ala Glu.

SEQ. ID. No. 126 was derived from the E7 region of HPV 6 and is comprised of 25 residues made up of amino acids starting at 86-/81- of the HPV 6 E7 oncoprotein having a GGPGG spacer sequence, as follows, with the sequence beginning at the amino terminal residue end: (SEQ. ID. No. 126) Arg Leu Asn Ile Val Ser Pro Ile Ser Ala Gly Gly Pro Gly Gly Leu Leu Leu Gly Thr Leu Asn Ile Val Glu.

SEQ. ID. No. 127 was derived from the E7 region of HPV 6 and is comprised of 24 residues made up of amino acids starting at 81-122- of the HPV 6 E7 oncoprotein having a GGPGG spacer sequence, as follows, with the sequence beginning at the amino terminal residue end: (SEQ. ID. No. 127) Lys Leu Leu Leu Gly Thr Leu Asn Ile Val Gly Gly Pro Gly Gly Leu His Ser Tyr Glu Gln Leu Val Glu.

SEQ. ID. No. 128 was derived from the E2 region of HPV 6 and is comprised of 25 residues made up of amino acids starting at 301-/35- of the HPV 6 E2 oncoprotein having a GGPGG spacer sequence, as follows, with the sequence beginning at the amino terminal residue end: (SEQ. ID. No. 128) Arg Tyr Arg Leu Asn Asp Lys His Arg His Gly Gly Pro Gly Gly Ile Arg His Glu Ser Val Leu Leu Tyr Asp.

SEQ. ID. No. 129 was derived from the E2 region of HPV 6 and is comprised of 24 residues made up of amino acids starting at 242-/118- of the HPV 6 E2 oncoprotein having a GGPGG spacer sequence, as follows, with the sequence beginning at the amino terminal residue end: (SEQ. ID. No. 129) His Val Gln Gln Ser Pro Ser Asn Ala Leu Gly Gly Pro Gly Gly Val Lys Phe Asp Gly Ser Ala Asn Asn.

SEQ. ID. No. 130 was derived from the E2 region of HPV 6 and is comprised of 25 residues made up of amino acids starting at 138-/131- of the HPV 6 E2 oncoprotein having a GGPGG spacer sequence, as follows, with the sequence beginning at the amino terminal residue end: (SEQ. ID. No. 130) Lys Tyr Val Gln Asp Thr Asp Ser Trp Val Gly Gly Pro Gly Gly Tyr Val Val Trp Thr Asp Val Tyr Val Glu.

SEQ. ID. No. 131 was derived from the E4 region of HPV 6 and is comprised of 25 residues made up of amino acids starting at 15-/22- of the HPV 6 E4 oncoprotein having a GGPGG spacer sequence, as follows, with the sequence beginning at the amino terminal residue end: (SEQ. ID. No. 131) Lys Tyr Val Leu Leu His Leu Tyr Leu Ala Gly Gly Pro Gly Gly Leu Ala Leu His Lys Lys Tyr Pro Phe Glu.

SEQ. ID. No. 132 was derived from the E4 region of HPV 6 and is comprised of 25 residues made up of amino acids starting at 9-/17- of the HPV 6 E4 oncoprotein having a GGPGG spacer sequence, and having Met replaced with Nle, as follows, with the sequence beginning at the amino terminal residue end: (SEQ. ID. No. 132) Lys Tyr Val Nle Ala Ala Gln Leu Tyr Val Gly Gly Pro Gly Gly Val Leu Leu His Leu Tyr Leu Ala Leu Asp.

SEQ. ID. No. 133 was derived from the E6 region of HPV 11 and is comprised of 25 residues made up of amino acids starting at 26-/28- of the HPV 11 E6 oncoprotein having a GPGPG spacer sequence, as follows, with the sequence beginning at the amino terminal residue end: (SEQ. ID. No. 133) Lys Leu Gln Ile Asn Ser Val Phe Ser Arg Gly Pro Gly Pro Gly Ile Gln Ser Val Phe Ser Arg Asn Ala Glu.

SEQ. ID. No. 134 was derived from the E6 region of HPV 11 and is comprised of 26 residues made up of amino acids starting at 26-/75- of the HPV 11 E6 oncoprotein having a GPGPG spacer sequence, and having Cys replaced with Ser, as follows, with the sequence beginning at the amino terminal residue end: (SEQ. ID. No. 134) Lys Thr Leu Gln Ile Gln Ser Val Phe Ser Arg Gly Pro Gly Pro Gly Asn Gln Tyr Arg His Phe Asn Tyr Ala Asp.

SEQ. ID. No. 135 was derived from the E6 regions of HPV 6 and 11 and is comprised of 25 residues made up of amino acids starting at 26-/26- of the HPV 6/11 E6 oncoprotein having a GPGPG spacer sequence, and having Cys replaced with Ser, as follows, with the sequence beginning at the amino terminal residue end: (SEQ. ID. No. 135) Lys Leu Gln Ile Asn Ser Val Phe Ser Arg Gly Pro Gly Pro Gly Leu Gln Ile Gln Ser Val Phe Ser Lys Asp.

SEQ. ID. No. 136 was derived from the E7 region of HPV 11 and is comprised of 26 residues made up of amino acids starting at 26-/26- of the HPV 11 E7 oncoprotein having a GPGPG spacer sequence, and having Cys replaced with Ser, as follows, with the sequence beginning at the amino terminal residue end: (SEQ. ID. No. 136) His Leu Asn Ile Val Ser Pro Ile Ser Ala Gly Pro Gly Pro Gly Tyr Gln Ile Leu Thr Ser Ser Ser Gly Ser Asp.

SEQ. ID. No. 137 was derived from the E7 region of HPV 11 and is comprised of 25 residues made up of amino acids starting at 81-/77- of the HPV 11 E7 oncoprotein having a GPGPG spacer sequence, as follows, with the sequence beginning at the amino terminal residue end: (SEQ. ID. No. 137) Arg Leu Leu Leu Gly Thr Leu Asn Ile Val Gly Pro Gly Pro Gly Gln Leu Gln Asp Leu Leu Leu Gly Thr Glu.

SEQ. ID. No. 138 was derived from the E7 regions of HPV 6 and 11 and is comprised of 25 residues made up of amino acids starting at 10-/86- of the HPV 11/6 E7 oncoprotein having a GPGPG spacer sequence, as follows, with the sequence beginning at the amino terminal residue end: (SEQ. ID. No. 138) His Ile Val Leu Asp Leu Gln Pro Pro Asp Gly Pro Gly Pro Gly Leu Asn Ile Val Ser Pro Ile Ser Ala Glu.

SEQ. ID. No. 139 was derived from the E7 regions of HPV 6 and 11 and is comprised of 24 residues made up of amino acids starting at 86-/10- of the HPV 11/6 E7 oncoprotein having a GGPGG spacer sequence, as follows, with the sequence beginning at the amino terminal residue end: (SEQ. ID. No. 139) Lys Leu Asn Ile Val Ser Pro Ile Ser Ala Gly Gly Pro Gly Gly Ile Val Leu Asp Leu Gln Pro Pro Asp.

SEQ. ID. No. 140 was derived from the E7 regions of HPV 6 and 11 and is comprised of 24 residues made up of amino acids starting at 82-/23- of the HPV 11/6 E7 oncoprotein having a GGPGG spacer sequence, as follows, with the sequence beginning at the amino terminal residue end: (SEQ. ID. No. 140) His Leu Leu Leu Gly Thr Leu Asn Ile Val Gly Gly Pro Gly Gly Leu His Ser Tyr Glu Gln Leu Glu Asp.

SEQ. ID. No. 141 was derived from the E2 region of HPV 11 and is comprised of 25 residues made up of amino acids starting at 300-/35- of the HPV 11 E2 oncoprotein having a GGPGG spacer sequence, as follows, with the sequence beginning at the amino terminal residue end: (SEQ. ID. No. 141) Lys Tyr Arg Leu Asn Asp Lys Tyr Lys His Gly Gly Pro Gly Gly Ile Arg Leu Glu Ser Val Leu Leu His Glu.

SEQ. ID. No. 142 was derived from the E2 region of HPV 11 and is comprised of 25 residues made up of amino acids starting at 118-/300- of the HPV 11 E2 oncoprotein having a GGPGG spacer sequence, as follows, with the sequence beginning at the amino terminal residue end: (SEQ. ID. No. 142) Arg Val Lys Phe Asp Gly Ser Glu Asp Asn Gly Gly Pro Gly Gly Lys Tyr Arg Leu Asn Asp Lys Tyr Lys Glu.

SEQ. ID. No. 143 was derived from the E2 region of HPV 11 and is comprised of 25 residues made up of amino acids starting at 35-/167- of the HPV 11 E2 oncoprotein having a GGPGG spacer sequence, as follows, with the sequence beginning at the amino terminal residue end: (SEQ. ID. No. 143) Lys Ile Arg Leu Glu Ser Val Leu Leu His Gly Gly Pro Gly Gly Tyr Val Asn Phe Asn Lys Glu Ala Gln Asp.

SEQ. ID. No. 144 was derived from the E2 region of HPV 11 and is comprised of 25 residues made up of amino acids starting at 94-/315- of the HPV 11 E2 oncoprotein having a GGPGG spacer sequence, and having Cys replaced with Ser, as follows, with the sequence beginning at the amino terminal residue end: (SEQ. ID. No. 144) His Tyr Val Gln Asp Thr Asp Ser Trp Val Gly Gly Pro Gly Gly Lys Leu Gly Phe Nle Ser Nle His Leu Glu.

SEQ. ID. No. 145 was derived from the E2 region of HPV 6 and 11 and is comprised of 25 residues made up of amino acids starting at 118-/118- of the HPV 11/6 E2 oncoprotein having a GGPGG spacer sequence, as follows, with the sequence beginning at the amino terminal residue end: (SEQ. ID. No. 145) Arg Val Lys Phe Asp Gly Ser Glu Asp Asn Gly Gly Pro Gly Gly Val Lys Phe Asp Gly Ser Ala Asn Asn Asp.

SEQ. ID. No. 146 was derived from the E2 region of HPV 6 and 11 and is comprised of 26 residues made up of amino acids starting at 138-/94- of the HPV 11/6 E2 oncoprotein having a GGPGG spacer sequence, as follows, with the sequence beginning at the amino terminal residue end: (SEQ. ID. No. 146) His Tyr Leu Asp Asn Asp Ser Trp Val Gly Gly Pro Gly Gly Lys Leu Gly Tyr Val Gln Asp Thr Asp Ser Trp Glu.

SEQ. ID. No. 147 was derived from the E4 region of HPV 11 and is comprised of 25 residues made up of amino acids starting at 15-/1- of the HPV 11 E4 oncoprotein having a GGPGG spacer sequence, as follows, with the sequence beginning at the amino terminal residue end: (SEQ. ID. No. 147) His Tyr Val Leu Leu His Leu Tyr Leu Ala Gly Gly Pro Gly Gly Val Val Pro Ile Ile Gly Lys Tyr Val Asp.

SEQ. ID. No. 148 was derived from the E4 region of HPV 11 and is comprised of 25 residues made up of amino acids starting at 1-/31- of the HPV 11 E4 oncoprotein having a GGPGG spacer sequence, as follows, with the sequence beginning at the amino terminal residue end: (SEQ. ID. No. 148) His Val Val Pro Ile Ile Gly Lys Tyr Val Gly Gly Pro Gly Gly Leu Asn Leu Leu His Thr Pro Pro His Asp.

SEQ. ID. No. 149 was derived from the E4 region of HPV 11 and is comprised of 25 residues made up of amino acids starting at 24-/17- of the HPV 11 E4 oncoprotein having a GGPGG spacer sequence, as follows, with the sequence beginning at the amino terminal residue end: (SEQ. ID. No. 149) Lys Ala Leu Tyr Glu Lys Tyr Pro Leu Leu Gly Gly Pro Gly Gly Val Leu Leu His Leu Tyr Leu Ala Leu Glu.

SEQ. ID. No. 150 was derived from the E4 regions of HPV 6 and 11 and is comprised of 25 residues made up of amino acids starting at 15-/22- of the HPV 11/6 E4 oncoprotein having a GGPGG spacer sequence, as follows, with the sequence beginning at the amino terminal residue end: (SEQ. ID. No. 150) Lys Tyr Val Leu Leu His Leu Tyr Leu Ala Gly Gly Pro Gly Gly Leu Ala Leu His Lys Lys Tyr Pro Phe Asp.

SEQ. ID. No. 151 was derived from the E4 regions of HPV 6 and 11 and is comprised of 25 residues made up of amino acids starting at 24-/9- of the HPV 11/6 E4 oncoprotein having a GGPGG spacer sequence, and having Met replaced with Nle, as follows, with the sequence beginning at the amino terminal residue end: (SEQ. ID. No. 151) Lys Ala Leu Tyr Glu Lys Tyr Pro Leu Leu Gly Gly Pro Gly Gly Tyr Val Nle Ala Ala Gln Leu Tyr Val Glu.

SEQ. ID. No. 152 was derived from the H-Ras protein and the E4 region of HPV 16 and is comprised of 25 residues made up of amino acids starting at 43-/72- of the HPV 16 E4 oncoprotein linked by a GGPGG spacer sequence to the H-Ras protein, as follows, with the sequence beginning at the amino terminal residue end: (SEQ. ID. No. 152) Lys Val Val Ile Asp Gly Glu Thr Ser Leu Gly Gly Pro Gly Gly Leu Gln Ser Ser Leu His Leu Thr Ala Glu.

SEQ. ID. No. 153 was derived from the H-Ras protein and the E4 region of HPV 16 and is comprised of 25 residues made up of amino acids starting at 81-/1- of the HPV 16 E4 oncoprotein linked by a GGPGG spacer sequence to the H-Ras protein, as follows, with the sequence beginning at the amino terminal residue end: (SEQ. ID. No. 153) Lys Phe Ala Ile Asn Asn Thr Lys Ser Phe Gly Gly Pro Gly Gly Tyr Val Leu His Leu Ser Leu Ala Ala Asp.

SEQ. ID. No. 154 was derived from the H-Ras protein and the E4 region of HPV 16 and is comprised of 26 residues made up of amino acids starting at 79- of the HPV 16 E4 oncoprotein linked by a GGPGG spacer sequence to amino acids starting at 20- of the H-Ras protein, as follows, with the sequence beginning at the amino terminal residue end: (SEQ. ID. No. 154) Lys Ile Gln Leu Ile Gln Asn His Phe Val Gly Gly Pro Gly Gly Lys Ile Ser Glu Tyr Arg His Tyr Ser Arg Glu.

SEQ. ID. No. 155 was derived from the H-Ras protein and the E4 region of HPV 33 and is comprised of 27 residues made up of amino acids starting at 43- of the H-Ras protein linked by a GGPGG spacer sequence to amino acids starting at 63- of the HPV 33 E4 oncoprotein, and having Cys replaced with Ser, as follows, with the sequence beginning at the amino terminal residue end: (SEQ. ID. No. 155) Lys Val Val Ile Asp Gly Glu Thr Ser Leu Gly Gln Gly Gly Pro Gly Gly Val Leu Gln Leu Thr Ala Gln Thr Ser Glu.

SEQ. ID. No. 156 was derived from the H-Ras protein and the E4 region of HPV 33 and is comprised of 25 residues made up of amino acids starting at 43- of the H-Ras protein linked by a GGPGG spacer sequence to amino acids starting at 7- of the HPV 33 E4 oncoprotein, and having Cys replaced with Ser, as follows, with the sequence beginning at the amino terminal residue end: (SEQ. ID. No. 156) Lys Val Val Ile Asp Gly Glu Thr Ser Leu Gly Gly Pro Gly Gly Tyr Leu Ala Thr Lys Tyr Pro Leu Leu Glu.

SEQ. ID. No. 157 was derived from the H-Ras protein and the E4 region of HPV 33 and is comprised of 23 residues made up of amino acids starting at 21-/7- of the HPV 33 E4 oncoprotein linked by a GGPGG spacer sequence to the H-Ras protein, as follows, with the sequence beginning at the amino terminal residue end: (SEQ. ID. No. 157) His Ile Gln Leu Ile Asn His Phe Val Gly Gly Pro Gly Gly Leu Ala Thr Lys Tyr Pro Leu Leu Asp.

SEQ. ID. No. 158 was derived from the H-Ras protein and the E4 region of HPV 58 and is comprised of 25 residues made up of amino acids starting at 81- of the of the H-Ras protein and amino acids starting at 7- of the HPV 58 E4 oncoprotein linked by a GGPGG spacer sequence to the H-Ras protein, as follows, with the sequence beginning at the amino terminal residue end: (SEQ. ID. No. 158) Lys Phe Leu Ser His Asp Thr Asp Leu Ser Gly Gly Pro Gly Gly Leu Val Ile Lys Tyr Pro Leu Leu Lys Asp.

SEQ. ID. No. 159 was derived from the H-Ras protein and the E4 region of HPV 45 and is comprised of 25 residues made up of amino acids starting at 43-/218- of the HPV 45 E4 oncoprotein linked by a GGPGG spacer sequence to the H-Ras protein, and having Cys replaced with Ser, as follows, with the sequence beginning at the amino terminal residue end: (SEQ. ID. No. 159) Lys Val Val Ile Asp Gly Glu Thr Ser Leu Gly Gly Pro Gly Gly Ile Val Arg Gln Leu Gln His Ala Ser Glu.

SEQ. ID. No. 160 was derived from the H-Ras protein and the E4 region of HPV 45 and is comprised of 25 residues made up of amino acids starting at 81-/44- of the HPV 45 E4 oncoprotein and linked by a GGPGG spacer sequence to the H-Ras protein, as follows, with the sequence beginning at the amino terminal residue end: (SEQ. ID. No. 160) Lys Phe Ala Ile Asn Asn Thr Lys Ser Phe Gly Gly Pro Gly Gly Arg Leu Leu Ser Asp Leu Asp Ser Val Glu.

SEQ. ID. No. 161 was derived from the H-Ras protein and the E4 region of HPV 45 and is comprised of 25 residues made up of amino acids starting at 8-/14- of the HPV 45 E4 oncoprotein linked by a GGPGG spacer sequence to the H-Ras protein, as follows, with the sequence beginning at the amino terminal residue end: (SEQ. ID. No. 161) Lys Val Gly Ala Gly Gly Val Gly Lys Ser Gly Gly Pro Gly Gly Leu Arg Leu Leu Asp Ser Tyr Asn Thr Glu.

SEQ. ID. No. 162 was derived from the H-Ras protein and the E4 region of HPV 45 and is comprised of 25 residues made up of amino acids starting at 21-/44- of the HPV 45 E4 oncoprotein linked by a GGPGG spacer sequence to the H-Ras protein, as follows, with the sequence beginning at the amino terminal residue end: (SEQ. ID. No. 162) Arg Ile Gln Leu Ile Gln Asn His Phe Val Gly Gly Pro Gly Gly Arg Leu Leu Ser Asp Leu Asp Ser Val Glu.

SEQ. ID. No. 163 was derived from the H-Ras protein and the E2 region of HPV 31 and is comprised of 25 residues made up of amino acids starting at 52-/260- of the HPV 31 E2 oncoprotein linked by a GGPGG spacer sequence to the H-Ras protein, as follows, with the sequence beginning at the amino terminal residue end: (SEQ. ID. No. 163) Lys Leu Asp Ile Leu Asp Thr Ala Gly Gln Gly Gly Pro Gly Gly Leu Leu Arg Gly Asp Ser Val Asp Ser Glu.

SEQ. ID. No. 164 was derived from the K-Ras protein and the E2 region of HPV 16 and is comprised of 25 residues made up of amino acids starting at 170-/35- of the HPV 16 E2 oncoprotein linked by a GGPGG spacer sequence to the K-Ras protein, and having Met replaced with Nle, as follows, with the sequence beginning at the amino terminal residue end: (SEQ. ID. No. 164) Lys Phe Leu Ser His Asp Thr Asp Leu Ser Gly Gly Pro Gly Gly Nle Arg Leu Glu Ser Ala Ile Tyr Tyr Glu.

SEQ. ID. No. 165 was derived from the K-Ras protein and the E2 region of HPV 16 and is comprised of 25 residues made up of amino acids starting at 93- of the HPV 16 E2 oncoprotein linked by a GGPGG spacer sequence to amino acids starting at 21- of the K-Ras protein, as follows, with the sequence beginning at the amino terminal residue end: (SEQ. ID. No. 165) His Ile Gln Leu Ile Gln Asn His Phe Val Gly Gly Pro Gly Gly Thr Leu Gln Asp Val Ser Leu Glu Val Glu.

SEQ. ID. No. 166 was derived from the K-Ras protein and the E5 region of HPV 16 and is comprised of 25 residues made up of amino acids starting at 170-/65- of the HPV 16 E5 oncoprotein linked by a GGPGG spacer sequence to the K-Ras protein, as follows, with the sequence beginning at the amino terminal residue end: (SEQ. ID. No. 166) Lys Phe Leu Ser His Asp Thr Asp Leu Ser Gly Gly Pro Gly Gly Phe Val Tyr Ile Pro Leu Phe Leu Ile Glu.

SEQ. ID. No. 167 was derived from the K-Ras protein and the E5 region of HPV 16 and is comprised of 25 residues made up of amino acids starting at 65- of the HPV 16 E5 oncoprotein linked by a GGPGG spacer sequence to amino acids starting at 18- of the K-Ras protein, as follows, with the sequence beginning at the amino terminal residue end: (SEQ. ID. No. 167) Arg Ser Leu Ala Ser Thr Ala Asp Thr Ile Gly Gly Pro Gly Gly Phe Val Tyr Ile Pro Leu Phe Leu Ile Glu.

SEQ. ID. No. 168 was derived from the K-Ras protein and the E4 region of HPV 18 and is comprised of 25 residues made up of amino acids starting at 163-/14- of the HPV 18 E4 oncoprotein linked by a GGPGG spacer sequence to the K-Ras protein, as follows, with the sequence beginning at the amino terminal residue end: (SEQ. ID. No. 168) Lys Leu Pro Gly Asp Thr Asp Leu Phe Leu Gly Gly Pro Gly Gly Leu Ser Leu Leu Asn Ser Tyr Ser Thr Asp.

SEQ. ID. No. 169 was derived from the K-Ras protein and the E4 region of HPV 18 and is comprised of 25 residues made up of amino acids starting at 189-/44- of the HPV 18 E4 oncoprotein linked by a GGPGG spacer sequence to the K-Ras protein, as follows, with the sequence beginning at the amino terminal residue end: (SEQ. ID. No. 169) Lys Thr Leu Gly Asp Thr Asp Ser Asn Thr Gly Gly Pro Gly Gly Arg Leu Leu His Asp Leu Asp Thr Val Glu.

SEQ. ID. No. 170 was derived from the CHSP60 protein and is comprised of 25 residues made up of amino acids starting at 364-/419- of the CHSP60 protein having a GGPGG spacer sequence, as follows, with the sequence beginning at the amino terminal residue end: (SEQ. ID. No. 169) Lys Leu Gln Glu Arg Leu Ala Lys Leu Glu Gly Gly Pro Gly Gly Ile Arg Ser Ile Pro Thr Leu Glu Ala Asp.

SEQ. ID. No. 171 was derived from the CHSP60 protein and is comprised of 23 residues made up of amino acids starting at 37-/219- of the CHSP60 protein having a GPG spacer sequence, as follows, with the sequence beginning at the amino terminal residue end: (SEQ. ID. No. 171) Lys Val Val Ile Asp Lys Ser Phe Gly Ser Gly Pro Gly Val Leu Ile Tyr Asp Lys Lys Ile Ser Glu.

SEQ. ID. No. 172 was derived from the CHSP60 protein and is comprised of 24 residues made up of amino acids starting at 364-/220- of the CHSP60 protein having a GGPGG spacer sequence, as follows, with the sequence beginning at the amino terminal residue end: (SEQ. ID. No. 172) Lys Leu Gln Glu Arg Leu Ala Lys Leu Gly Gly Pro Gly Gly Leu Ile Tyr Asp Lys Lys Ile Ser Gly Asp.

SEQ. ID. No. 173 was derived from the CHSP60 protein and is comprised of 25 residues made up of amino acids starting at 446-/5- of the CHSP60 protein having a GGPGG spacer sequence, and having Met replaced with Nle, as follows, with the sequence beginning at the amino terminal residue end: (SEQ. ID. No. 173) Lys Ile Ile Phe Gln Gln Val Nle Ser Arg Gly Gly Pro Gly Gly Asn Ile Lys Tyr Asn Glu Glu Ala Arg Asp.

SEQ. ID. No. 174 was derived from the PTEN protein and is comprised of 25 residues made up of amino acids starting at 138-147/375-383 of the PTEN protein having a GPGPG spacer sequence, as follows, with the sequence beginning at the amino terminal residue end: (SEQ. ID. No. 174) Arg Tyr Leu Leu His Arg Gly Lys Phe Leu Gly Pro Gly Pro Gly Tyr Arg Tyr Ser Asp Thr Thr Asp Ser Glu.

SEQ. ID. No. 175 was derived from the PTEN protein and is comprised of 23 residues made up of amino acids starting at 7-16/173-181 of the PTEN protein having a GPG spacer sequence, as follows, with the sequence beginning at the amino terminal residue end: (SEQ. ID. No. 175) Asp Ile Val Ser Arg Asn Lys Arg Arg Tyr Gly Pro Gly Tyr Val Tyr Tyr Tyr Ser Tyr Leu Leu Glu.

SEQ. ID. No. 176 was derived from the PTEN protein and is comprised of 22 residues made up of amino acids starting at 111-119/187-195 of the PTEN protein having a GPG spacer sequence, as follows, with the sequence beginning at the amino terminal residue end: (SEQ. ID. No. 176) Lys Typ Leu Ser Glu Asp Asp Asn His Val Gly Pro Gly Tyr Arg Pro Val Ala Leu Leu Arg Asp.

SEQ. ID. No. 177 was derived from the CHSP60 protein and the E7 region of HPV 18 and is comprised of 31 residues made up of amino acids starting at 364- of the CHSP60 protein linked by a GGPGG spacer sequence to amino acids 33-48 of the HPV 18 E7 oncoprotein, as follows, with the sequence beginning at the amino terminal residue end: (SEQ. ID. No. 177) Lys Leu Gln Glu Arg Leu Ala Lys Leu Gly Gly Pro Gly Gly Asp Ser Glu Glu Glu Asn Asp Glu Ile Gly Asp Val Asn His Gln His Asp.

SEQ. ID. No. 178 was derived from the CHSP60 protein and the E7 region of HPV 16 and is comprised of 29 residues made up of amino acids starting at 364- of the CHSP60 protein linked by a GGPGG spacer sequence to amino acids 81-94 of the HPV 16 E7 oncoprotein, and having Met replaced with Nle, as follows, with the sequence beginning at the amino terminal residue end: (SEQ. ID. No. 178) Lys Leu Gln Glu Arg Leu Ala Lys Leu Gly Gly Pro Gly Gly Leu Leu Nle Gly Thr Leu Gly Ile Val Ser Pro Ile Ser Ser Glu.

SEQ. ID. No. 179 was derived from the CHSP60 protein and the E6 region of HPV 16 and is comprised of 40 residues made up of amino acids starting at 364- of the CHSP60 protein linked by a GPG spacer sequence to amino acids 1-26 of the HPV 16 E6 oncoprotein, and having Met replaced with Nle and Cys replaced with Ser, as follows, with the sequence beginning at the amino terminal residue end: (SEQ. ID. No. 179) Lys Leu Gln Glu Arg Leu Ala Lys Leu Gly Pro Gly Lys Nle His Gln Lys Arg Thr Ala Nle Phe Gln Asp Pro Gln Glu Arg Pro Arg Lys Leu Pro Gln Leu Ser Thr Glu Leu Asp.

SEQ. ID. No. 180 was derived from the CHSP60 protein and the E7 region of HPV 16 and is comprised of 25 residues made up of amino acids starting at 364- of the CHSP60 protein linked by a GGPGG spacer sequence to amino acids 28-39 of the HPV 16 E7 oncoprotein, as follows, with the sequence beginning at the amino terminal residue end: (SEQ. ID. No. 180) Lys Leu Gln Glu Arg Leu Ala Lys Gly Gly Pro Gly Gly Leu Asn Asp Ser Ser Glu Glu Glu Asp Glu Ile Asp.

SEQ. ID. No. 181 was derived from the CHSP60 protein, the E7 region of HPV 58, and the E7 region HPV 16 and is comprised of 40 residues made up of amino acids starting at 446- of the CHSP60 protein linked by a GPG spacer sequence to amino acids 37-45 of the HPV 58 E7 oncoprotein, further linked by another GPG spacer sequence to amino acids 82-95 of the HPV 16 E7 oncoprotein, and having Met replaced with Nle and Cys replaced with Ser, as follows, with the sequence beginning at the amino terminal residue end: (SEQ. ID. No. 181) Lys Ile Ile Phe Gln Gln Val Nle Ser Arg Gly Pro Gly Ile Gly Leu Asp Gly Pro Asp Gly Gln Gly Pro Gly Leu Leu Nle Gly Thr Leu Gly Ile Val Ser Pro Ile Ser Ser Glu.

SEQ. ID. No. 182 was derived from the CHSP60 protein and the E7 region of HPV 58 and is comprised of 30 residues made up of amino acids starting at 419-427 of the CHSP60 protein linked by a GPG spacer sequence to amino acids 77-92 of the HPV 58 E7 oncoprotein, and having Met replaced with Nle and Cys replaced with Ser, as follows, with the sequence beginning at the amino terminal residue end: (SEQ. ID. No. 182) Lys Ile Arg Ser Ile Pro Thr Leu Glu Ala Gly Pro Gly Val Arg Thr Leu Gln Gln Leu Leu Nle Gly Thr Ser Thr Ile Val Ser Asp.

The following example will illustrate the practice of the present invention in further detail. It will be readily understood by those skilled in the art that the following methods, formulations, and compositions of novel peptides from the early, late coding regions of E2, E4, E6, and E7 oncoproteins of HPV 6, 11, 16, 18 31, 33, 45, 52 and 58 of the present invention, as generally described and illustrated in the following Examples, are to be viewed as exemplary of the principles of the present invention, and not as restrictive to a particular structure or process for implementing those principles. Thus, the following more detailed description of the presently preferred embodiments of the methods, formulations, and compositions of the present invention, as represented in Example 1, is not intended to limit the scope of the invention, as claimed, but is merely representative of presently preferred embodiments of the invention.

EXAMPLE 1

1. Synthesis of the Amino Acid Sequences or Peptides

While the peptides of the invention may be obtained by a variety of prior art methods, including but not limited to recombinant sources, chemical synthesis is the preferred method as it facilitates the accumulation of a sizable quantity of peptide in a substantially pure form, 95 to 99% by weight in the present case. The synthesis of peptides may be done on a 0.25 scale using (9-fluorenyl) methoxycarbonyl (FMOC)-protected L-amino acids, with super acid-labile 2-chlorotrityl resin (Novabiochem, Nottingham, UK) as a solid support. Resin preloaded into a reaction vessel may be washed with dimethyl formamide and then drained completely. A volume of 10 ml of 20% piperidine in dimethyl formamide may be added to this resin. The mixture may then be shaken for 5 minutes and drained. Another 10 ml of 20% piperidine in dimethyl formamide may be added, and the mixture shaken for 30 minutes. After draining, the resin may be washed with dimethyl formamide four times, and then once with dichloromethane. The resin beads may be considered appropriately prepared if they turn blue using the standard ninhydrin test.

For each amino acid, a coupling solution may be added to the resin in the appropriate order, with the coupling reaction repeated until all amino acids are in place along the peptide. The coupling solution may be prepared comprising: 1 mmol Fmoc Amino acid of choice; 2.1 ml 0.45 M 1H-(Benzotriazole-1-Yl)-1,1,3,3-tetramethyluronium-hexafluoro-phosphate/hydrobenzotriazole [1 mmol]; and 348 µl of N,N-diisopropylethylamine [2 mmol]. The mixture may be shaken for a minimum of 30 minutes. The reaction vessel may then be drained, and the resin washed four times with dimethylformamide, with the final wash done with dichloromethane. A standard ninhydrin test may be performed to ascertain coupling of the amino acids.

The completed peptide may be cleaved from the resin by reacting the mixture for two hours with a solution of 5% $H_2O$, 5% phenol, 3% thioanisole, 3% ethanedithiol, 3% triisopropylsilane, and 81% trifluoroacetic acid. After the completed peptide is cleaved from the resin, the resin mixture may be filtered with cold methyl-tbutyl-ether. The precipitated peptide may then be washed twice with cold methyl-tbutyl-ether and dried under gaseous nitrogen. The molecular weight of the peptide may be checked by Matrix-Assisted laser Desorption Time-of Flight Mass Spectrometry, and the purity by High Performance Liquid Chromatography using a C18, 300 Å column. The synthesized peptide sequences may be at a 99% level of purity, but it is emphasized that lesser levels may still be considered appropriate for assay purposes.

2. Storage of the Amino Acid Peptides

The manufactured amino acid sequences or peptides may be stored at −20° C. The working solution of the peptides may be suspended in PBS at pH 7.2 to a concentration of 1 mg/ml, and may be stored in sealed vials at −20° C.

3. Coating Peptides of the Amino Acids onto the High Binding Titer Plates

The synthesized amino acid sequences may be bound to titer plates using REACTI-BIND™ Maleic Anhydride Activated Polystyrene plates (Pierce, Rockford, Ill.). Each amino acid sequence may be diluted to 12.5 µg/ml with coating buffer (PBS pH 7.2 or 50 mM sodium bicarbonate buffer, pH 9.4). To each titer well, 100 µl (1.25 µg) of the diluted sequence solution may be added. The plate may then be incubated for four hours at room temperature with shaking, and may be kept at 4° C. overnight. The plate may then be emptied and the residual liquid tapped onto a clean paper towel. Each well may be washed with 200 µl PBS, pH 7.2 at least once. Each time the plate is emptied the residual liquid may be tapped onto a clean paper towel. Next, a 200 µl blocking solution of 4% fat-free dry milk in PBS, pH 7.2 may be added to each well. After the blocking solution is left in the well for about 2-3 minutes, the titer plate may then be emptied by inversion. This step may be repeated several times. The titer plates may then be dried at room temperature and stored at 4° C. for up to four months.

4. Samples Collection

The following protocol is for the collection of cervical mucus to test for the presence of IgA antibody against HPV peptides. First, a 2 cm aspirette may be inserted into the Uterine OS cervix. The aspirette is a symmetrical tube, with 1 cm graded increments and a Teflon plunger. Next, about 100-200 µl of the collected cervical mucus may be measured and dispensed into an Eppendorff test tube and immediately put on ice. The sample may be immediately frozen at −70° C.

The following protocol is for the collection of cellular material from cervical smears for HPV DNA detection and genotyping. Cells may first be obtained from cervical endo- and exo-cervical smears with a cytobrush. The smears may be collected in PBS containing Merthiolate. Next, the pellets may be washed once with PBS and resuspended in 0.2-0.5 ml of 10 mM Tris-HCL, pH 7.5. The samples may then be frozen at −70° C. For a polymerase chain reaction (PCR) assay, a 10 µl aliquot suspension may be taken and boiled for 10 minutes. The sample may then be kept on ice, and centrifuged at 3,000 g for 1 minute before use in a HPV PCR.

The following protocol is for collection of sera material from human blood samples for detecting IgG antibodies against HPV peptides. First, venous blood may be obtained by prescribed phlebotomy methods using a "red top" tube with a 21 or 22-gauge double-pointed needle. About 7-9 ml of blood may be taken from the subject. After allowing 15-20 minutes at room temperature for clot formation of the sample to occur, the blood may be centrifuged at 2,500 g for 15 minutes. Serum may be separated by aspiration from the clotted cells, using a disposable pipette and dispensing 0.25-ml aliquots into Eppendorf tubes. Samples may be stored at −80° C.

5. Immunoassay of the ELISA

Peptides may be resuspended in PBS, pH 7.4 (0.01 M phosphate, 0.15 M NaCl, pH 7.4) to a concentration of 1 mg/ml. The peptide solution may then be diluted to a concentration of 12.5 µg/ml with PBS, pH 7.4. A 100 µl volume of diluted peptide solution (containing 1.25 µl of peptide) may then be added to each well of the Reacti-Bind Maleic Anhydride Activated 96-well Polystyrene plates. The plate may then be incubated on a microplate shaker for 3-4 hours at room temperature, followed by incubation at 4° C. overnight.

HPV peptide-coated plates may be washed in PBS-0.1% Tween-20, several times and then blocked with 10% goat serum in PBS, pH 7.4 blocking solution, [Life Technologies] or 4% fat-free dry milk in PBS for 1 hour. Alternatively, peptide-coated plates may be blocked by washing the plates three times with SuperBlock solution [Pierce] at room temperature for 3-5 minutes per each wash. If the plates are not immediately used, the plates may be covered with a plastic sealer and stored at 4° C. The plates may be washed several times with PBS-0.05% Tween-20 wash solution, [J. T. Baker, Phillipsburg, N.J.] in an automatic plate washer (Skanwasher 300; Skatron, Lier, Norway) before using.

Patient or normal control serum may be diluted 1:40 and mucus may be diluted 1:10 with 10% Superblock and 0.05% Tween-20 in PBS, pH 7.4 dilution buffer. A 400 µl volume of diluted sample may be made for each serum sample, if three HPV peptides are tested in a 96-well plate. The plates may be washed three times with PBS-0.05% Tween-20 wash solution before using. A 100 µl sample of diluted serum may be added to each well that has been coated with a different peptide and blocked by a blocking solution. Blank controls may be prepared by adding PBS containing no serum to wells and incubated in the assay plate for 1 hour at room temperature with occasionally shaking. Multiple pipettes may be used to rinse each well six times with 300 µl of PBS wash buffer, pH 7.4 containing 0.01% Tween-20. Each rinse may last for 3 minutes after which the plate is emptied and the residual liquid tapped onto a paper towel.

A 100 µl volume of HRP-Mouse-anti-Human IgG or anti-IgA diluted 1:12,000 with PBS-BSA fetal calf serum (FCS) (PBS at pH 7.4 containing 3% BSA and 0.5% FCS) dilution buffer may be added to each well including the blank wells. The assay plate may be incubated for 1 hour at room temperature with occasional shaking. Each well may be rinsed with 300 µl of wash buffer six times for 3 minutes each time using a multiple channel pipette. After each rinse, the plate may be emptied and the residual liquid tapped on a paper towel. A 100 µl volume of 1-Step Tubro TMB-ELISA 3,3',5,5' tetramethylbenzidine (TMB) which is a substrate for Horseradish Peroxides, may be added to each well including blank wells using the multiple Channel pipetteman, to protect the sample from light because it is light sensitive.

The samples may be incubated for 15-30 minutes at room temperature or until a visually obvious enough green-blue color develops. The blue color may be measured at 652 nm. However, a 100 µl stop solution of 1-2 M $H_2SO_4$ acid may be added into each well including blank wells to create a yellow color.

6. Visualization/Interpretation of Completed ELISA Tests

The reactions may be detected in 45 min by absorbance readings at 450 nm with an automated plate reader. An OD450 (optical waverland) reading at 450 nm >0.3~1.0 may indicate that HPV antibodies are present. An OD450 nm reading of a negative control may be in the range of 0.05-0.08. However, different negative controls may yield different OD range readings, depending on the negative control used. TABLE 1 refers to absorbance values and diagnosis of dysplasia from subjects tested for cervical disease via Enzyme-Linked Immunosorbent Assay (ELISA), using peptides of the present invention.

Throughout the description and drawings, example embodiments are given with reference to specific configurations. It will be appreciated by those of ordinary skill in the art that the present invention can be embodied in other specific forms. Those of ordinary skill in the art would be able to practice such other embodiments without undue experimentation. The scope of the present invention, for the purpose of the present patent document, is not limited merely to the specific example embodiments of the foregoing description, but rather is indicated by the appended claims. All changes that come within the meaning and range of equivalents within the claims are intended to be considered as being embraced within the spirit and scope of the claims.

What is claimed is:

1. An isolated protein sequence or peptide from HPV for detecting or diagnosing cancer or cellular abnormalities, said isolated protein sequence or peptide selected from: an E6 region of HPV 58 and an E7 region of HPV 16 as set forth in SEQ. ID. No.: 19.

* * * * *